(12) United States Patent
Bougher, III et al.

(10) Patent No.: US 10,941,175 B2
(45) Date of Patent: *Mar. 9, 2021

(54) PYRROLOPYRIMIDINE NUCLEOSIDES AND ANALOGS THEREOF

(71) Applicants: Chimerix, Inc., Durham, NC (US); The Regents of the University of Michigan, Ann Arbor, MI (US)

(72) Inventors: John Henry Bougher, III, Durham, NC (US); Ramamurty V S Changalvala, Durham, NC (US); Aaron Leigh Downey, Durham, NC (US); John C. Drach, Ann Arbor, MI (US); Ernest Randall Lanier, Jr., Durham, NC (US); Andrew Louis McIver, Durham, NC (US); Bradley David Robertson, Durham, NC (US); Dean Wallace Selleseth, Durham, NC (US); Phiroze Behram Sethna, Durham, NC (US); Leroy Townsend, Ann Arbor, MI (US); Roy W. Ware, Durham, NC (US)

(73) Assignees: Chimerix, Inc., Durham, NC (US); The Regents of the University of Michigan, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/533,194

(22) Filed: Aug. 6, 2019

(65) Prior Publication Data
US 2020/0199167 A1    Jun. 25, 2020

Related U.S. Application Data

(63) Continuation of application No. 15/599,056, filed on May 18, 2017, now Pat. No. 10,407,457, which is a continuation of application No. 15/358,938, filed on Nov. 22, 2016, now Pat. No. 9,701,706, which is a continuation of application No. 15/231,528, filed on Aug. 8, 2016, now Pat. No. 9,708,359.

(60) Provisional application No. 62/202,010, filed on Aug. 6, 2015.

(30) Foreign Application Priority Data

Apr. 15, 2016  (GB) .................................... 1606645

(51) Int. Cl.
| | | |
|---|---|---|
| A01N 43/04 | (2006.01) |
| A61K 31/70 | (2006.01) |
| C07H 19/14 | (2006.01) |
| C07D 239/70 | (2006.01) |
| C07H 19/16 | (2006.01) |
| A61K 31/7052 | (2006.01) |
| A61K 31/706 | (2006.01) |
| A61K 31/7064 | (2006.01) |

(52) U.S. Cl.
CPC ........... C07H 19/14 (2013.01); C07D 239/70 (2013.01); C07H 19/16 (2013.01); *A61K 31/706* (2013.01); *A61K 31/7052* (2013.01); *A61K 31/7064* (2013.01)

(58) Field of Classification Search
None
See application file for complete search history.

(56) References Cited

U.S. PATENT DOCUMENTS

| | | |
|---|---|---|
| 3,423,398 A | 1/1969 | Rao et al. |
| 4,140,851 A | 2/1979 | Townsend |
| 4,892,865 A | 1/1990 | Townsend et al. |
| 5,177,064 A | 1/1993 | Bodor |
| 5,403,843 A | 4/1995 | Akimoto et al. |
| 5,502,187 A | 3/1996 | Ayer et al. |

(Continued)

FOREIGN PATENT DOCUMENTS

| | | |
|---|---|---|
| CN | 1923171 | 3/2007 |
| CN | 1923173 | 3/2007 |

(Continued)

OTHER PUBLICATIONS

Cuellar. "HIV-Infection-Associated Inflammatory Musculoskeletal Disorders," *Disease Clinics of North America* (1998) vol. 24 No. 2, pp. 403-421.

(Continued)

*Primary Examiner* — Patrick T Lewis
(74) *Attorney, Agent, or Firm* — Cooley LLP; Ivor R. Elrifi; Heidi A. Erlacher

(57) ABSTRACT

The present disclosure provides pyrrolopyrimidine nucleoside analogs of the Formula I, Formula IA, Formula IB, or Formula II and phospholipid conjugates and pharmaceutical compositions thereof wherein $R_c$ and A are defined herein. Also presented are methods of treating and/or preventing viral infection and/or viral infection-associated disease or disorder with one or more compounds of Formula I, Formula IA, Formula IB, or Formula II.

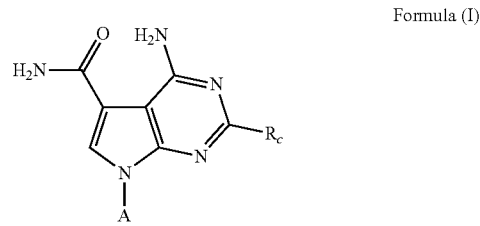

Formula (I)

16 Claims, 16 Drawing Sheets
Specification includes a Sequence Listing.

(56) References Cited

U.S. PATENT DOCUMENTS

| | | | |
|---|---|---|---|
| 5,506,347 A | 4/1996 | Erion et al. |
| 5,554,608 A | 9/1996 | Ahluwalia et al. |
| 5,646,128 A | 7/1997 | Firestein et al. |
| 5,656,745 A | 8/1997 | Bischofberger et al. |
| 5,674,998 A | 10/1997 | Boyer et al. |
| 5,721,356 A | 2/1998 | Ugarkar et al. |
| 5,726,302 A | 3/1998 | Ugarkar et al. |
| 5,763,167 A | 6/1998 | Conrad |
| 5,763,596 A | 6/1998 | Boyer et al. |
| 5,789,394 A | 8/1998 | Nguyen-Ba et al. |
| 5,798,340 A | 8/1998 | Bischofberger et al. |
| 5,834,469 A | 11/1998 | Elliott et al. |
| 5,955,446 A | 9/1999 | Budowsky |
| 6,051,578 A | 4/2000 | Chen |
| 6,419,934 B1 | 7/2002 | Tobinick |
| 6,455,508 B1 | 9/2002 | Ramasamy |
| 6,468,991 B1 | 10/2002 | Budowsky et al. |
| 6,664,266 B2 | 12/2003 | He et al. |
| 6,670,468 B1 | 12/2003 | Cuenoud et al. |
| 6,777,395 B2 | 8/2004 | Bhat et al. |
| 6,777,404 B2 | 8/2004 | Hamanaka et al. |
| 6,831,069 B2 | 12/2004 | Tam et al. |
| 7,115,741 B2 | 10/2006 | Levy |
| 7,230,007 B2 | 6/2007 | Carry et al. |
| 7,323,453 B2 | 1/2008 | Olsen et al. |
| 7,358,262 B2 | 4/2008 | Stockwell |
| 7,361,671 B2 | 4/2008 | Van Zandt et al. |
| 7,553,826 B2 | 6/2009 | Boyer et al. |
| 7,608,600 B2 | 10/2009 | Storer et al. |
| 7,615,554 B2 | 11/2009 | Becklin et al. |
| 7,629,328 B2 | 12/2009 | Roberts et al. |
| 7,648,987 B2 | 1/2010 | Crew et al. |
| 7,687,500 B2 | 3/2010 | Howell et al. |
| 7,964,580 B2 | 6/2011 | Sofia et al. |
| 8,124,602 B2 | 2/2012 | Breault et al. |
| 8,124,745 B2 | 2/2012 | Allerson et al. |
| 8,173,621 B2 | 5/2012 | Du et al. |
| 8,207,136 B2 | 6/2012 | Gartel et al. |
| 8,278,282 B2 | 10/2012 | Yin et al. |
| 8,404,683 B2 | 3/2013 | Lacrampe et al. |
| 8,415,095 B2 | 4/2013 | Cupo et al. |
| 8,475,804 B2 | 7/2013 | Johansen et al. |
| 8,487,004 B2 | 7/2013 | Chen et al. |
| 8,575,119 B2 | 11/2013 | Wang et al. |
| 8,609,627 B2 | 12/2013 | Cho et al. |
| 8,642,602 B2 | 2/2014 | Mann et al. |
| 8,642,660 B2 | 2/2014 | Goldfarb |
| 8,674,085 B2 | 3/2014 | Sommadossi et al. |
| 8,697,713 B2 | 4/2014 | Jaekel et al. |
| 8,748,601 B2 | 6/2014 | Taunton et al. |
| 8,815,879 B2 | 8/2014 | Kasina et al. |
| 9,085,599 B2 | 7/2015 | Or et al. |
| 2001/0041673 A1 | 11/2001 | Fossa |
| 2002/0127593 A1 | 9/2002 | Reich et al. |
| 2002/0169140 A1 | 11/2002 | Prendergast |
| 2004/0006002 A1 | 1/2004 | Sommadosi et al. |
| 2004/0014108 A1 | 1/2004 | Eldrup et al. |
| 2004/0175384 A1 | 9/2004 | Mohapatra et al. |
| 2004/0259934 A1 | 12/2004 | Johansson et al. |
| 2005/0158741 A1 | 7/2005 | Mulligan et al. |
| 2005/0203151 A1 | 9/2005 | Malecha et al. |
| 2005/0282769 A1 | 12/2005 | Klimko et al. |
| 2006/0234962 A1 | 10/2006 | Olsen et al. |
| 2006/0264389 A1 | 11/2006 | Bhat et al. |
| 2007/0015771 A1 | 1/2007 | Matteucci |
| 2007/0161644 A1 | 7/2007 | Stockwell |
| 2007/0265222 A1 | 11/2007 | Maccoss et al. |
| 2007/0299091 A1 | 12/2007 | Gmeiner et al. |
| 2008/0153903 A1 | 6/2008 | Fleenor et al. |
| 2008/0255038 A1 | 10/2008 | Hopkins et al. |
| 2009/0318380 A1 | 12/2009 | Sofia et al. |
| 2010/0144655 A1 | 6/2010 | Chen et al. |
| 2010/0184650 A1 | 7/2010 | Jensen et al. |
| 2010/0297079 A1 | 11/2010 | Almond et al. |
| 2011/0218210 A1 | 9/2011 | Refaeli et al. |
| 2012/0010164 A1 | 1/2012 | Surnma et al. |
| 2012/0014911 A1 | 1/2012 | Fuchs et al. |
| 2012/0190680 A1 | 7/2012 | Bakthavatchalam et al. |
| 2012/0208750 A1 | 8/2012 | Kahn et al. |
| 2012/0238600 A1 | 9/2012 | Choi-Sledeski et al. |
| 2012/0245186 A1 | 9/2012 | Blackman et al. |
| 2013/0011393 A1 | 1/2013 | Lancaster et al. |
| 2013/0018010 A1 | 1/2013 | Zhao et al. |
| 2013/0137708 A1 | 5/2013 | Garske et al. |
| 2013/0281686 A1 | 10/2013 | Cho et al. |
| 2014/0213779 A1 | 7/2014 | Dixon et al. |
| 2015/0018301 A1 | 1/2015 | Lee et al. |
| 2015/0057243 A1 | 2/2015 | Zhou et al. |
| 2015/0087627 A1 | 3/2015 | Ren et al. |

FOREIGN PATENT DOCUMENTS

| | | |
|---|---|---|
| CN | 102286048 | 12/2011 |
| JP | S 61189225 | 8/1986 |
| JP | 2003321472 | 11/2003 |
| JP | 2007124252 | 5/2007 |
| KR | 2001086627 | 2/2000 |
| WO | WO 9205200 | 4/1992 |
| WO | WO 9217185 | 10/1992 |
| WO | WO 9418215 | 8/1994 |
| WO | WO 2003/020222 | 3/2003 |
| WO | WO 2003/051899 | 6/2003 |
| WO | WO 03/055896 A2 | 7/2003 |
| WO | WO 2003/061576 | 7/2003 |
| WO | WO 2003/075010 | 9/2003 |
| WO | WO 2004/028481 | 4/2004 |
| WO | WO 2005/020885 | 3/2005 |
| WO | WO 2007/024944 | 3/2007 |
| WO | WO 2008/021981 | 2/2008 |
| WO | WO 2008/132155 | 11/2008 |
| WO | WO 2009/067409 | 5/2009 |
| WO | WO 2009/105234 | 8/2009 |
| WO | WO 2009/108551 | 9/2009 |
| WO | WO 2010/015637 | 2/2010 |
| WO | WO 2011/079103 | 6/2011 |
| WO | WO 2011/106997 | 9/2011 |
| WO | WO 2012/041965 | 4/2012 |
| WO | WO 2012/153142 | 11/2012 |
| WO | WO 2013/071415 | 5/2013 |
| WO | WO 2014/060431 | 4/2014 |
| WO | WO 2014/177585 | 11/2014 |

OTHER PUBLICATIONS

Naus, Petr et al., "Synthesis, Cytostatic, Antimicrobial, and Anti-HCV Activity of 6-Substituted 7-(Het)aryl-7-deazapurine Ribonucleosides", *Journal of Medicinal Chemistry*, vol. 57, No. 3, (2014), pp. 1097-1110.

Porcari, Anthony R. et al.., "Synthesis and Antiviral Activity of 2-Substituted Analogs of Triciribine", *Nucleosides, Nucleotides and Nucleic Acids*, vol. 22, No. 12, (2003), pp. 2171-2193.

SEQUENCE LISTING

```
<160> NUMBER OF SEQ ID NOS: 13

<210> SEQ ID NO 1
<211> LENGTH: 20
<212> TYPE: DNA
<213> ORGANISM: Human herpesvirus 4

<400> SEQUENCE: 1
cccaggagtc ccagtagtca                                               20

<210> SEQ ID NO 2
<211> LENGTH: 20
<212> TYPE: DNA
<213> ORGANISM: Human herpesvirus 4

<400> SEQUENCE: 2
cagttcctcg ccttaggttg                                               20

<210> SEQ ID NO 3
<211> LENGTH: 20
<212> TYPE: DNA
<213> ORGANISM: Human herpesvirus 6

<400> SEQUENCE: 3
ccttgatcat tcgaccgttt                                               20

<210> SEQ ID NO 4
<211> LENGTH: 20
<212> TYPE: DNA
<213> ORGANISM: Human herpesvirus 6

<400> SEQUENCE: 4
tgggattggg attagagctg                                               20

<210> SEQ ID NO 5
<211> LENGTH: 23
<212> TYPE: DNA
<213> ORGANISM: Human herpesvirus 8

<400> SEQUENCE: 5
ttccccagat acacgacaga atc                                           23
```

```
<210> SEQ ID NO 6
<211> LENGTH: 17
<212> TYPE: DNA
<213> ORGANISM: human herpesvirus 8

<400> SEQUENCE: 6
cggagcgcag gctacct                                                    17

<210> SEQ ID NO 7
<211> LENGTH: 17
<212> TYPE: DNA
<213> ORGANISM: Human herpesvirus 8

<400> SEQUENCE: 7
cctacgtgtt cgtcgac                                                    17

<210> SEQ ID NO 8
<211> LENGTH: 21
<212> TYPE: DNA
<213> ORGANISM: BK virus

<400> SEQUENCE: 8
agtggatggg cagcctatgt a                                               21

<210> SEQ ID NO 9
<211> LENGTH: 20
<212> TYPE: DNA
<213> ORGANISM: BK virus

<400> SEQUENCE: 9
tcatatctgg gtcccctgga                                                 20

<210> SEQ ID NO 10
<211> LENGTH: 33
<212> TYPE: DNA
<213> ORGANISM: BK virus

<400> SEQUENCE: 10
aggtagaaga ggttagggtg tttgatggca cag                                  33

<210> SEQ ID NO 11
<211> LENGTH: 21
<212> TYPE: DNA
<213> ORGANISM: JC virus

<400> SEQUENCE: 11
ctggtcatgt ggatgctgtc a                                               21

<210> SEQ ID NO 12
<211> LENGTH: 21
<212> TYPE: DNA
<213> ORGANISM: JC virus

<400> SEQUENCE: 12
gccagcaggc tgttgatact g                                               21

<210> SEQ ID NO 13
<211> LENGTH: 17
<212> TYPE: DNA
<213> ORGANISM: JC virus

<400> SEQUENCE: 13
ccctttgttt ggctgct                                                    17
```

PYRROLOPYRIMIDINE NUCLEOSIDES AND ANALOGS THEREOF

RELATED APPLICATIONS

This application is a continuation of U.S. Ser. No. 15/599,056, filed May 18, 2017 (now allowed), which is a continuation of U.S. Ser. No. 15/358,938, filed Nov. 22, 2016 (now U.S. Pat. No. 9,701,706 issued on Jul. 11, 2017), which is a continuation of U.S. Ser. No. 15/231,528, filed Aug. 8, 2016 (now U.S. Pat. No. 9,708,359 issued on Jul. 18, 2017), which claims priority to and the benefit of U.S. Provisional Application No. 62/202,010, filed Aug. 6, 2015, and to U.K. Application No. 1606645.8, filed Apr. 15, 2016, the entire contents of each of which are incorporated by reference herein in their entireties.

GOVERNMENT INTEREST

This invention was made with government support under Grant Number 5 Ul9-AI-03 1 718 (National Cooperative Drug Discovery Group for Opportunistic Infections: New Inhibitors and New Targets to Develop HCMV Drugs), awarded by the National Institute of Allergy and Infectious Diseases. The government has certain rights in the invention.

INCORPORATION BY REFERENCE OF SEQUENCE LISTING

The contents of the text file named "CHIM-830_C02US_ST25.txt", which was created on May 4, 2017 and is 2.18 KB in size, are hereby incorporated by reference in their entireties.

TECHNICAL FIELD

This application relates to pyrrolopyrimidine nucleoside analogs and phospholipid conjugates thereof and methods of synthesis thereof. The pyrrolopyrimidine nucleoside analogs and their phospholipid conjugates can be used as antiviral agents for treating viral infections. This application also relates to pharmaceutical compositions comprising pyrrolopyrimidine nucleoside analogs and phospholipid conjugates thereof.

BACKGROUND

Viral infections can have serious adverse effects on individuals and society as a whole. In addition to fatal viral infections such as ebola, even non-fatal infections can have serious societal and economic consequences. For example, human noroviruses (NV) are the most common cause of epidemic acute gastroenteritis worldwide with an estimated 19-21 million cases each year in the United States including 56,000-71,000 hospitalizations and 570-800 deaths (Hall et al., *Emerg. Infect. Dis.* 2013 August; 19(8):1198-205).

Accordingly, development of an effective antiviral treatment effective against viruses is important to improve the health of infected individuals and as a public health measure to prevent outbreaks of other pathogenic viruses.

SUMMARY

The present disclosure provides pyrrolopyrimidine nucleoside analogs and phospholipid conjugates thereof. Also included are pharmaceutical compositions comprising the same and methods of synthesis thereof.

The present disclosure also provides methods of treating and/or preventing viral infection and/or viral infection-associated disease or disorder with one or more compounds of the present embodiments. The disclosure addresses the need for new therapies that can be used to treat and/or prevent viral-induced disease using novel antivirals and delivery vehicles.

In one aspect, the present disclosure relates to compounds of Formula I:

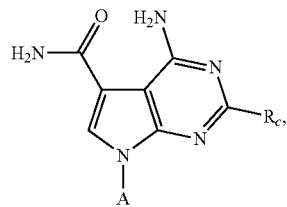

(Formula I)

and pharmaceutically acceptable salts, solvates, enantiomers, diastereomers, racemates and mixtures thereof, wherein:

A is:

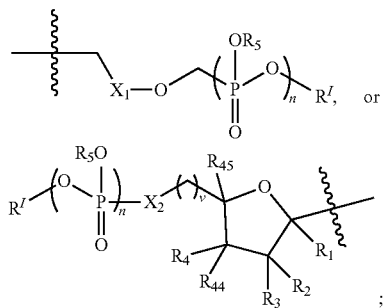

$X_1$ is $CR_{11}R_{12}$ or $OCH_2CH_2$ with the oxygen atom distal to the $R^I$ moiety in A, in which $R_{11}$ and $R_{12}$ are independently hydrogen or substituted or unsubstituted $C_1$-$C_4$ alkyl;

$X_2$ is absent, —O—, —C(O)O—, or —OCH$_2$— with the oxygen atom distal to the $R^I$ moiety in A;

each $R^I$ independently is hydrogen, substituted or unsubstituted $C_1$-$C_6$ alkyl,

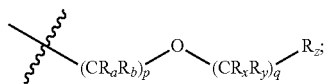

or $R^I$ is an amino acid residue bound via the carbonyl group of $X_2$;

v is 0 or 1;

n is 0, 1, 2, or 3 and when $X_2$ is —C(O)O—, n is 0;

p is 2, 3, 4, 5, 6, 7, 8, 9, 10, or 11;

q is 1, 2, 3, 4, 5, 6, 7, 8, 9, 10, 11, 12, 13, 14, 15, 16, 17, or 18;

$R_z$ is hydrogen, halogen, $C_1$-$C_4$ alkylthio, $C_1$-$C_4$ alkoxy, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted heteroaryl, substituted or unsubstituted cycloalkyl, substituted or unsubstituted cycloalkenyl; or substituted or unsubstituted non-aromatic heterocyclic ring;

$R_a$, $R_b$, $R_x$, and $R_y$ are each independently selected from the group consisting of hydrogen, halogen, OH, SH, substituted or unsubstituted $C_1$-$C_6$ alkoxy, substituted or unsubstituted aryloxy, substituted or unsubstituted $C_1$-$C_6$ alkylthio, substituted or unsubstituted arylthio, substituted or unsubstituted —O-carbonylalkyl, substituted or unsubstituted —O— carbonylaryl, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted aryl, substituted or unsubstituted heteroaryl, substituted or unsubstituted cycloalkyl, and substituted or unsubstituted cycloaklenyl;

alternatively any $R_a$ or $R_b$ in $(CR_aR_b)_p$ is taken with another $R_a$ or $R_b$, together with the atoms to which they are attached and any intervening atoms therebetween to form a carbon-carbon double or triple bond, a $C_6$-$C_{10}$ aryl, 5- to 10-membered heteroaryl, $C_3$-$C_{10}$ cycloalkyl, $C_4$-$C_{10}$ cycloalkenyl, or 5- to 10-membered non-aromatic heterocyclic ring structure; or any $R_x$ or $R_y$ in $(CR_xR_y)_q$ is taken with another $R_x$ or $R_y$, together with the atoms to which they are attached and any intervening atoms therebetween to form a carbon-carbon double or triple bond, a $C_6$-$C_{10}$ aryl, 5- to 10-membered heteroaryl, $C_3$-$C_{10}$ cycloalkyl, $C_4$-$C_{10}$ cycloalkenyl, or 5- to 10-membered non-aromatic heterocyclic ring structure; or any $CR_aR_b$ or $CR_xR_y$ is replaced by oxygen, sulfur, sulfinyl (SO) or sulfonyl ($SO_2$);

$R_1$ and $R_{45}$ are each independently hydrogen, halogen, substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_4$-$C_8$ cycloalkenyl, substituted or unsubstituted $C_2$-$C_6$ alkynyl, substituted or unsubstituted $C_8$-$C_{12}$ cycloalkynyl, azido, —OH, substituted or unsubstituted $C_1$-$C_6$ alkoxy, substituted or unsubstituted amino, —SH, or substituted or unsubstituted $C_1$-$C_6$ alkylthio;

each of $R_2$, $R_3$, $R_4$ and $R_{44}$ independently is hydrogen, halogen, substituted or unsubstituted $C_1$-$C_6$ alkyl, $N_3$, OH, substituted or unsubstituted $C_1$-$C_6$ alkoxy, substituted or unsubstituted amino, SH, or substituted or unsubstituted $C_1$-$C_6$ alkylthio; alternatively $R_3$ and one of $R_4$ and $R_{44}$ together with the atoms to which they are attached form a carbon-carbon double bond;

$R_5$ is hydrogen, $R^I$, $M^+$, substituted or unsubstituted aryl, substituted or unsubstituted aralkyl, substituted or unsubstituted $C_1$-$C_6$ alkyl, substituted or unsubstituted $C_1$-$C_6$ heteroalkyl, substituted or unsubstituted cycloalkyl, substituted or unsubstituted non-aromatic heterocyclic ring, or substituted or unsubstituted heteroaryl; wherein $M^+$ is a cation and wherein $R_5$ is not an amino acid; and $R_c$ is substituted or unsubstituted $C_1$-$C_6$ alkyl, substituted or unsubstituted $C_3$-$C_6$ cycloalkyl, substituted or unsubstituted $C_2$-$C_6$ alkenyl, substituted or unsubstituted $C_4$-$C_8$ cycloalkenyl, substituted or unsubstituted $C_2$-$C_6$ alkynyl, substituted or unsubstituted $C_8$-$C_{12}$ cycloalkynyl, or substituted or unsubstituted aryl.

In another aspect the present disclosure relates to compounds of Formula IA:

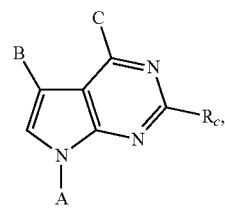

(IA)

and pharmaceutically acceptable salts, solvates, enantiomers, diastereomers, racemates or mixtures thereof, wherein:

A is:

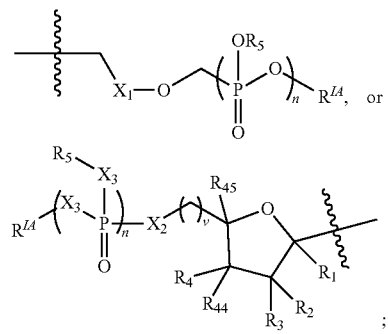

$X_1$ is —$CR_{11}R_{12}$— or —$OCH_2CH_2$— wherein the oxygen atom is distal to the $R^{IA}$ moiety in A;

$R_{11}$ and $R_{12}$ are independently hydrogen or $C_1$-$C_4$ alkyl, wherein the alkyl is optionally substituted with one or more halogen, —OH, —SH, or —$NH_2$;

$X_2$ is absent, —O—, —C(O)O—, or —$OCH_2$— wherein the oxygen atom is distal to the $R^{IA}$ moiety in A;

$X_3$ is independently —O— or —NH—;

B is independently —C(O)$NH_2$, aryl, or heteroaryl;

C is independently —OR, —NHR, or —N=CHN(R)$_2$;

each $R^{IA}$ is independently is hydrogen or —$C_1$-$C_6$ alkyl, wherein the alkyl is optionally substituted with one or more —OH, —SH, or —$NH_2$, oxo, $R_a$, or —$OR_a$;

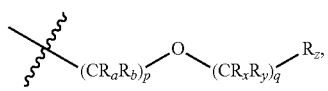

or $R^{IA}$, is an amino acid residue bound via the carbonyl group, v is 0 or 1;
n is 0, 1, 2, or 3 and when $X_2$ is —C(O)O—, n is 0;
p is 2, 3, 4, 5, 6, 7, 8, 9, 10, or 11;
q is 1, 2, 3, 4, 5, 6, 7, 8, 9, 10, 11, 12, 13, 14, 15, 16, 17, or 18;

$R_z$ is hydrogen, halogen, —$C_1$-$C_4$ alkylthio, —$C_1$-$C_4$ alkoxy, —$C_1$-$C_4$ alkyl, —$C_2$-$C_4$ alkenyl, —$C_2$-$C_4$ alkynyl, aryl, heteroaryl, —$C_3$-$C_8$ cycloalkyl, —$C_4$-$C_8$ cycloalkenyl, or 3- to 5-membered nonaromatic heterocycle, wherein each alkylthio, alkoxy, alkyl, alkenyl, alkynyl, aryl, heteroaryl, cycloalkyl, cycloalkenyl, or heterocycle is optionally substituted with one or more halogen, —OH, —SH, or —$NH_2$;

$R_a$, $R_b$, $R_x$, and $R_y$ are each independently selected from the group consisting of hydrogen, halogen, —OH, —SH, —C$_1$-C$_6$ alkoxy, aryloxy, —C$_1$-C$_6$ alkylthio, arylthio, —OC(O)C$_1$-C$_6$, alkyl, —OC(O)aryl, —C$_1$-C$_6$ alkyl, —C$_2$-C$_6$ alkenyl, —C$_2$-C$_6$ alkynyl, aryl, heteroaryl, —C$_3$-C$_8$ cycloalkyl, and —C$_4$-C$_8$ cycloaklenyl, wherein each alkoxy, aryloxy, alkylthio, arylthio, alkyl, aryl, alkenyl, alkynyl, heteroaryl, cycloalkyl, or cycloalkenyl is optionally substituted with one or more halogen, —OR$_{11}$, —SR$_{11}$, or —NR$_{11}$R$_{12}$;

or any two R$_a$ or R$_b$, together with the atom to which they are both attached, can combine to form a C$_3$-C$_8$ spirocycloalkyl or 3- to 8-membered spiroheterocycle;

or any two R$_a$ or R$_b$, when on adjacent atoms, can combine to form a cis- or trans-carbon-carbon double bond or a carbon-carbon triple bond;

or any two R$_a$ or R$_b$, when on adjacent atoms, can combine to form an oxo, aryl, heteroaryl, —C$_3$-C$_{10}$cycloalkyl, —C$_4$-C$_{10}$cycloalkenyl, or 5- to 10-membered ring heterocycle;

or any CR$_a$R$_b$ can be replaced by —O—, —S—, —S(O)—, or —SO$_2$—;

or any two R$_x$ or R$_y$, together with the atom to which they are both attached, can combine to form a —C$_3$-C$_8$ spirocycloalkyl or 3- to 8-membered spiroheterocycle;

or any two R$_x$ or R$_y$, when on adjacent atoms, can combine to form a cis- or trans-carbon-carbon double bond or a carbon-carbon triple bond;

or any two R$_x$ or R$_y$, when on adjacent atoms, can combine to form an oxo, aryl, heteroaryl, —C$_3$-C$_{10}$cycloalkyl, —C$_4$-C$_{10}$cycloalkenyl, or 5- to 10-membered ring heterocycle;

or any CR$_x$R$_y$ can be replaced by —O—, —S—, —S(O)—, or —SO$_2$—;

R$_1$ and R$_{45}$ are each independently hydrogen, halogen, —N$_3$, —OH, —NH$_2$, —SH, —C$_1$-C$_6$ alkyl, —C$_3$-C$_6$ cycloalkyl, —C$_2$-C$_6$ alkenyl, —C$_4$-C$_8$ cycloalkenyl, —C$_2$-C$_6$ alkynyl, —C$_8$-C$_{12}$ cycloalkynyl, —C$_1$-C$_6$ alkoxy, or —C$_1$-C$_6$ alkylthio wherein each alkyl, cycloalkyl, alkenyl, cycloalkenyl, alkynyl, cycloalkynyl, alkoxy or alkylthio is independently substituted with one or more halogen, —N$_3$, —OH, —NH$_2$, or —SH;

R$_2$, R$_3$, R$_4$ and R$_{44}$ are each independently hydrogen, halogen, —N$_3$, —OH, —NH$_2$, —SH, —C$_1$-C$_6$ alkyl, —C$_1$-C$_6$ alkoxy, or —C$_1$-C$_6$ alkylthio, wherein each alkyl, alkoxy, or alkylthio is optionally substituted with one or more halogen, oxo, —N$_3$, —OH, —NH$_2$, or —SH;

or R$_3$ and one of R$_4$ and R$_{44}$, together with the atoms to which they are attached, can form a carbon-carbon double bond;

or R$_3$ and one of R$_4$ and R$_{44}$, together with the atoms to which they are attached, can combine to form a 4- to 8-membered cycloalkyl or heterocycle optionally substituted with C$_1$-C$_6$ alkyl;

R$_5$ is independently hydrogen, —R$^{IA}$, M$^+$, aryl, aralkyl, —C$_1$-C$_6$ alkyl, —C$_1$-C$_6$ heteroalkyl, cycloalkyl, non-aromatic heterocyclic ring, or heteroaryl, wherein M$^+$ is a cation and wherein each aryl, aralkyl, alkyl, heteroalkyl, cycloalkyl, heterocycle, or heteroaryl is optionally substituted with one or more halogen, —N$_3$, —OH, —NH$_2$, or —SH, and wherein R$_5$ is not an amino acid; and R$_{11}$ and R$_{12}$ are each independently, at each occurrence, hydrogen, halogen, —OH, —SH, —C$_1$-C$_6$ alkoxy, aryloxy, —C$_1$-C$_6$ alkylthio, arylthio, —OC(O)C$_1$-C$_6$ alkyl, —OC(O) aryl, —C$_1$-C$_6$ alkyl, —C$_2$-C$_6$ alkenyl, —C$_2$-C$_6$ alkynyl, aryl, heteroaryl, —C$_3$-C$_8$ cycloalkyl, and —C$_4$-C$_8$ cycloaklenyl, wherein each alkyl, aryl, alkenyl, alkynyl, heteroaryl, cycloalky and cycloalkenyl is optionally substituted with one or more halogen, —N$_3$, —OH, —NH$_2$, or —SH;

R$_c$ is —C$_1$-C$_6$ alkyl, —C$_3$-C$_6$ cycloalkyl, —C$_1$-C$_6$ alkenyl, —C$_4$-C$_8$ cycloalkenyl, —C$_2$-C$_6$ alkynyl, —C$_8$-C$_{12}$ cycloalkynyl, or aryl, wherein each alkyl, cycloalkyl, alkenyl, cycloalkenyl, or aryl is optionally substituted with one or more halogen, —N$_3$, —OH, —NH$_2$, or —SH; wherein any of the nitrogen atoms in the fused pyrimidine ring can be oxidized.

In another aspect the present disclosure relates to compounds of Formula II:

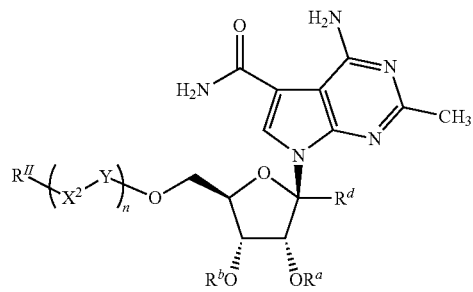

(II)

and pharmaceutically acceptable salts, solvates, enantiomers, diastereomers, racemates or mixtures thereof, wherein:

Y is —C(O)—, or

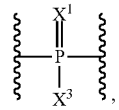

wherein X$^1$ is independently O, NH, or S, X$^2$ is independently a bond, —O—, —S—, or —NH—, and X$^3$ is independently —OR, —NHR$^H$, or —SR$^H$;

each R$^H$ is independently —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, R$^1$, —OR$^1$, —NR$^1$NR$^2$, —SR$^1$, —OC(O)R$^1$, —C(O)OR$^1$, —NHC(O)OR$^1$, or —NHC(O)R$^1$;

R$^a$ and R$^b$ are each independently, at each occurrence, —H, —C$_1$-C$_{20}$alkyl, —C$_2$-C$_{20}$alkenyl, —C$_2$-C$_{20}$ alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —OR$^1$, —NR$^1$R$^2$, —SR$^1$, —OC(O)R$^1$, —C(O)OR$^1$—NHC(O)OR$^1$, or —NHC(O)R$^1$;

R$^1$ and R$^2$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —R$^3$, —R$^4$, —OR$^3$, —NR$^3$R$^4$, —SR$^3$, —OC(O)R$^3$, —C(O)OR$^3$, —NHC(O)OR$^3$, or —NHC(O)R$^3$;

R$^3$ and R$^4$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —NH$_2$, —SH, —OC(O)H, —C(O)OH, —NHC(O)OH, or —NHC(O)H;

R$^a$ is independently —H or -D; and n is independently 0, 1, 2 or 3.

In another aspect, the present disclosure relates to a pharmaceutical composition comprising a compound of Formula I, Formula IA, Formula IB, or Formula II, or a pharmaceutically acceptable salt, solvate, enantiomer, diastereomer, racemate or mixture thereof, and a pharmaceutically acceptable carrier. In some embodiments the present disclosure relates to a pharmaceutical composition comprising compound 1, or a pharmaceutically acceptable salt, solvate, enantiomer, diastereomer, racemate or mixture thereof, and a pharmaceutically acceptable carrier. In some embodiments, the pharmaceutical composition can be used to treat a viral infection (e.g., norovirus).

In another aspect, the present disclosure provides a method of treating a viral infection or a viral-infection associated disease or disorder, wherein the method comprises administering to a subject in need thereof an effective amount of a compound described herein (e.g., a compound of Formula I, Formula IA, Formula IB, or Formula II), or a pharmaceutically acceptable salt, solvate, enantiomer, diastereomer, racemate or mixture thereof. In some embodiments the compound is compound 1, or a pharmaceutically acceptable salt, solvate, enantiomer, diastereomer, racemate or mixture thereof. In some embodiments, the virus is norovirus.

In another aspect, the present disclosure also relates to a pharmaceutical formulation of the compounds disclosed herein, or a pharmaceutically acceptable salt, solvate, enantiomer, diastereomer, racemate or mixture thereof, for use in a method for treating or preventing a viral infection or viral infection associated disease or disorder, e.g., a double stranded DNA (dsDNA) or a single stranded RNA (ssRNA) viral infection. In some embodiments the compound is compound 1. In some embodiments, the virus is norovirus.

In another aspect, the present disclosure also relates to use of a compound or a pharmaceutical formulation disclosed herein, or a pharmaceutically acceptable salt, solvate, enantiomer, diastereomer, racemate or mixture thereof, in the manufacture of a medicament for treating or preventing a viral infection and/or viral infection associated disease or disorder, e.g., an ssRNA viral infection. The pharmaceutical formulation can comprise a compound of Formula I, Formula IA, Formula IB, or Formula II, or a pharmaceutically acceptable salt, solvate, enantiomer, diastereomer, racemate or mixture thereof. In some embodiments the compound is compound 1, or a pharmaceutically acceptable salt, solvate, enantiomer, diastereomer, racemate or mixture thereof. In some embodiments, the virus is norovirus.

The present disclosure also relates to methods for treating or preventing a viral infection and/or viral infection associated disease or disorder, e.g., an ssRNA viral infection. The method can comprise administering to a subject in need thereof a compound of Formula I, Formula IA, Formula IB, or Formula II. In some embodiments the compound is compound 1. In some embodiments, the virus is norovirus.

The present disclosure also relates to a compound described herein, or a pharmaceutically acceptable salt, solvate, enantiomer, diastereomer, racemate or mixture thereof, for use in treating or preventing a viral infection or a viral infection-associated disease or disorder. The compound can be a compound of Formula I, Formula IA, Formula IB, or Formula II. In some embodiments the compound is compound 1, or a pharmaceutically acceptable salt, solvate, enantiomer, diastereomer, racemate or mixture thereof. In some embodiments, the virus is norovirus.

Unless otherwise defined, all technical and scientific terms used herein have the same meaning as commonly understood by one of ordinary skill in the art to which this disclosure belongs. In the case of conflict, the present specification, including definitions, will control. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents, and other references mentioned herein are incorporated by reference. The references cited herein are not admitted to be prior art to the claimed disclosure. In addition, the materials, methods, and examples are illustrative only and are not intended to be limiting.

Other features and advantages of the present disclosure will be apparent from the following detailed description and claims.

DETAILED DESCRIPTION

Figure 1A:
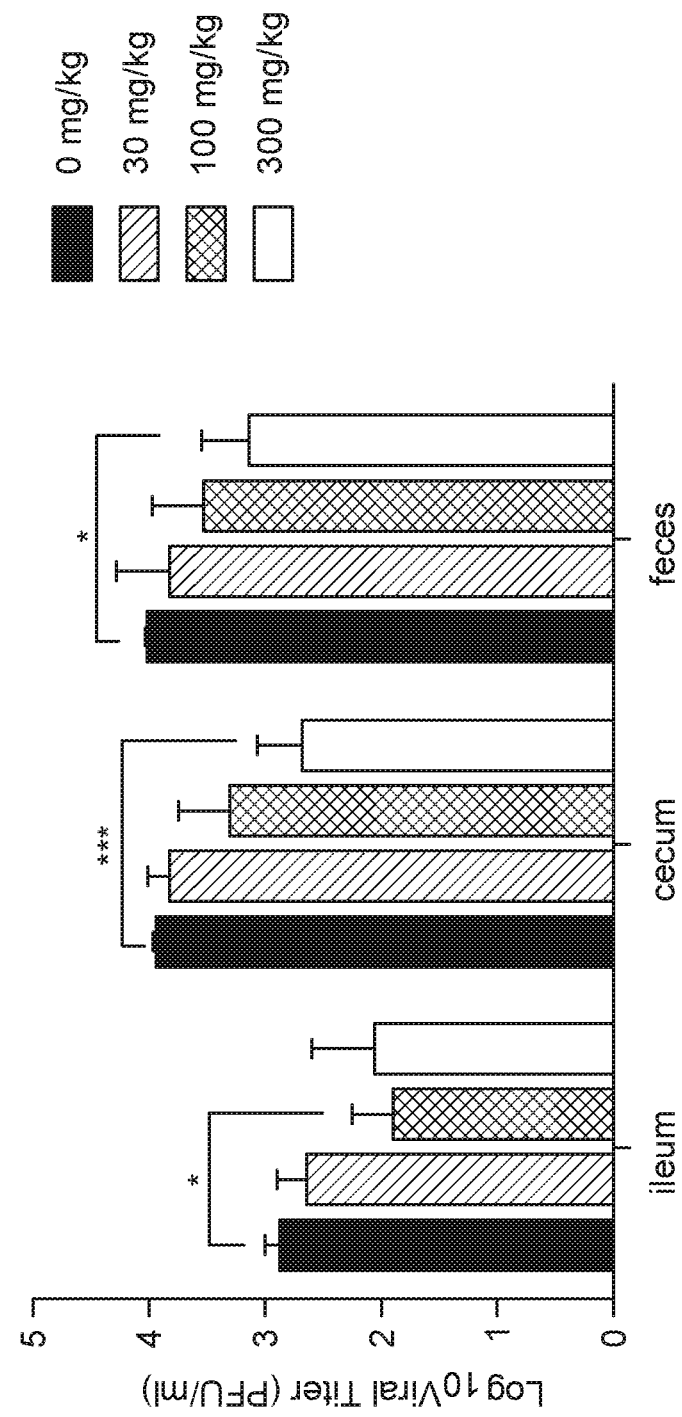
FIG. 1A shows murine norovirus titer (plaque forming units per mL) in tissue and feces harvested 3 days post-infection as part of Study No. 1.

Nucleoside phosphonates (e.g., ribonucleoside derivatives) represent a target class of antivirals to inhibit viruses which rely on viral encoded enzymes using ribonucleotides or deoxyribonucleotides as substrates, such as certain viral polymerases for many RNA viruses and/or viral helicases for RNA (e.g., ssRNA) or DNA viruses. However, without wishing to be bound by theory, one block to efficacy for this class of antivirals is the requirement for biochemical modification of the administered agent inside target cells to form the active antiviral nucleoside triphosphate. In some embodiments, if a nucleoside is delivered, three phosphorylation steps are required to form the triphosphate. Delivery of nucleoside phosphonates effectively bypasses the first phosphorylation, but can exacerbate problems of delivering clinically useful amounts of the charged drug across the lipid bilayers surrounding cells.

Without wishing to be bound by theory, lipid conjugation can be used to disguise oral drugs, including nucleoside phosphonates, as natural compounds that are readily absorbed by the body. Specifically, in some embodiments, nucleoside phosphonates can be modified to resemble partially metabolized (monoacyl) phospholipids. In some embodiments, in contrast to normal diacylphospholipids, monoacyl lipid-modified nucleosides can readily penetrate the enterocytes lining the lumen of the gut, enter the circulating blood and/or lymph and, unlike standard drugs, remain intact. Consequently, the lipid moiety can do more than deliver the nucleoside to the plasma; it can facilitate efficient uptake into the target cells. The lipid can be cleaved in the cytoplasmic compartment of the target cells and in the case of nucleoside analog conjugates, can yield the corresponding monophosphate. Overall, this strategy can lead to greatly increased levels of the active antiviral at the site of viral replication.

The present disclosure provides compounds, pharmaceutical compositions, and methods of synthesizing and using the compounds for treating or preventing a viral infection or viral infection associated disease or disorder, e.g., an ssRNA viral infection.

In some embodiments, the compounds of the present disclosure have improved efficacy/toxicity ratio compared to compounds in the art used similarly.

Definitions

Certain compounds of the present disclosure and definitions of specific functional groups are also described in more detail below.

It will be appreciated that the compounds, as described herein, may be substituted with any number of substituents or functional moieties. In general, the term "substituted" whether preceded by the term "optionally" or not, and substituents contained in formulas disclosed herein, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this disclosure, heteroatoms such as nitrogen may have hydrogen substituents and/or any permissible substituents of organic compounds described herein which satisfy the valencies of the heteroatoms. The nitrogen and sulfur heteroatoms may optionally be oxidized, and the nitrogen heteroatom may optionally be quaternized. Examples of substituents on the moieties disclosed herein (e.g., alkyl, alkenyl, alkynyl, alkoxy, aryl, heteroaryl, cycloalkyl, cycloalkenyl, non-aromatic heterocycle groups) include, but are not limited to, alkenyl, alkynyl, halogen, haloalkyl, alkoxy, alkylthio, alkylsulfinyl, alkylsulfonyl, heteroaryl, aryl, cycloalkyl, cycloalkenyl, non-aromatic heterocycle, hydroxyl, carbamoyl, oxo, amino, nitro, azido, —SH, and —CN.

The present disclosure is intended to include all isotopes of atoms occurring in the present compounds. Isotopes include those atoms having the same atomic number but different mass numbers. In particular one, some, or all hydrogens may be deuterium. Radioactive isotopes may be used, for instance for structural analysis or to facilitate tracing the fate of the compounds or their metabolic products after administration. By way of general example and without limitation, isotopes of hydrogen include deuterium and tritium and isotopes of carbon include C-13 and C-14. For example, compounds of Formula I include those wherein $R_1$ is H or D; $R_2$ and $R_3$ are independently H, D, OH, OD, $CH_3$, or $CD_3$; and/or $R_4$ is H, D, $CH_3$, or $CD_3$.

The term "independently" is used herein to indicate that the variable, such as atom or functional group, which is independently applied, varies independently from application to application. For example, where more than one substituent or atom (carbon or heteroatom, such as oxygen (O), sulfur (S), or nitrogen (N)) occurs, each substituent or atom is independent of another substituent or atom and such substituents or atom can also alternate.

The term "alkyl", as used herein, refers to saturated, straight-chain or branched hydrocarbon radicals containing, in certain embodiments, between one and twenty, including between one and ten, or between one and six, carbon atoms. Branched means that one or more lower $C_1$-$C_6$ alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl. Examples of $C_1$-$C_6$ alkyl radicals include, but are not limited to, methyl, ethyl, propyl, isopropyl, butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals. Examples of $C_1$-$C_{20}$ alkyl radicals include but are not limited to hexadecamethyl, hexadecaethyl, hexadecopropyl, octadecamethyl, octadecaethyl, octadecapropyl and the like.

The term "alkenyl", as used herein, denotes a monovalent straight or branched group derived from a hydrocarbon moiety containing, in certain embodiments, from two to six, or two to eight, or two to twenty carbon atoms having at least one carbon-carbon double bond. The double bond may or may not be the point of attachment to another group. Examples of $C_2$-$C_8$ alkenyl groups include, but are not limited to, for example, ethenyl, propenyl, butenyl, 1-methyl-2-buten-1-yl, heptenyl, octenyl and the like. As defined herein, "akenyl" groups include both cis- and trans-isomers.

The term "alkynyl", as used herein, denotes a monovalent straight or branched group derived from a hydrocarbon moiety containing, in certain embodiments, from two to six, or two to eight, or two to twenty carbon atoms having at least one carbon-carbon triple bond. The triple bond may or may not be the point of attachment to another group. Examples of $C_2$-$C_8$ alkynyl groups include, but are not limited to, for example, ethynyl, propynyl, butynyl and the like.

The term "alkoxy" refers to an —O-alkyl radical.

The term "thioalkyl" or "alkylthio" refers to an —S-alkyl radical. In some embodiments, thio group can be replaced by a sulfinyl (SO) or sulfonyl ($SO_2$).

The terms "hal", "halo", or "halogen", as used herein, refer to an atom selected from fluorine, chlorine, bromine and iodine.

The terms "haloalkyl", "haloalkenyl", or "haloalkynyl", as used herein refer to an alkyl, alkenyl or alkynyl that is substituted with one or more halogens or halo groups. Examples of haloalkyl include but are not limited to $CF_3$, $CH_2CF_3$, $CCl_3$.

The term "aryl", as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like. The term aryl includes indoline.

The term "cycloalkyl", as used herein, denotes a monovalent group derived from a monocyclic or polycyclic saturated carbocyclic ring compound. Examples of $C_3$-$C_8$-cycloalkyl (3- to 8-membered cycloalkyl) include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl and the like.

The term "cycloalkenyl", as used herein, denotes a monovalent group derived from a monocyclic or polycyclic partially unsaturated (i.e., non-aromatic) carbocyclic ring compound. In other words, it refers to a monovalent group derived from a monocyclic or polycyclic carbocyclic ring compound having at least one carbon-carbon double bond. Examples of such groups include, but are not limited to, cyclopropenyl, cyclobutenyl, cyclopentenyl, cyclohexenyl, cycloheptenyl, cyclooctenyl, and the like.

The term "cycloalkynyl," as used herein, denotes a monovalent group derived from a monocyclic or polycyclic partially unsaturated (i.e., non-aromatic) carbocyclic compound having at least one carbon-carbon triple bond. Examples include cyclooctyne.

The term "heteroaryl", as used herein, refers to a mono- or poly-cyclic (e.g., hi-, or tri-cyclic or more) fused or non-fused, radical or ring system having at least one aromatic ring, having from five to ten ring atoms of which at least one ring atom is selected from S, O, P, and N. In other words, heteroaryl is aryl where containing at least one heteroatom. Examples of heteroaryl include but are not limited to pyridinyl, furanyl, thiazolyl, imidazolyl, indolyl, benzofuranyl, and the like.

The term "5- or 6-membered heteroaryl", is taken to mean a ring having five to twelve ring atoms of which at least one ring atom is selected from S, O, P, and N. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "non-aromatic heterocyclic" ring or "non-aromatic heterocycle," as used herein, refers to a saturated or unsaturated monocyclic or polycyclic, fused or non-fused system, where, for example, at least one ring contains between one and four heteroatoms independently selected from oxygen, sulfur, phosphorous and nitrogen. The nitrogen and sulfur heteroatoms may optionally be oxidized, and the nitrogen heteroatom may optionally be quaternized. Representative non-aromatic heterocyclic groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

As used herein, the term "oxo" is understood to describe a carbonyl group (i.e., C(O)).

As described herein, compounds of the disclosure may optionally be substituted with one or more substituents, such as those illustrated generally above, or as exemplified by particular classes, subclasses, and species of the disclosure. It will be appreciated that the phrase "optionally substituted" is used interchangeably with the phrase "substituted or unsubstituted." In general, the term "substituted," whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituents selected from a specified group, the substituent may be either the same or different at every position.

The term "protected" as described herein, refers to functional groups or compounds of the present disclosure having a protecting group used in synthesis to temporarily mask the characteristic chemistry of a functional group (such as hydroxyl, amino, carboxyl, etc.) because it interferes with another reaction. After completion of the reaction, these protecting groups are removed by common methods, or protected compounds are used as prodrugs or as the compounds of the disclosure.

The term "prodrug" or "pharmaceutically acceptable prodrugs", as used herein refers to compounds that are rapidly transformed in vivo to yield the parent compound, for example by hydrolysis in blood (T. Higuchi and V. Stella, *Pro-drugs as Novel Delivery Systems*, Vol. 14 of the ACS. Symposium Series; Edward B. Roche, ed., *Bioreversible Carriers in Drug Design*, American Pharmaceutical Association and Pergamon Press, 1987, both of which are incorporated herein by reference).

The term "pharmaceutical" or "pharmaceutically acceptable" when used herein as an adjective, means substantially non-toxic and substantially non-deleterious to the recipient. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

By "pharmaceutical formulation" it is further meant that the carrier, solvent, excipient(s) and salt must be compatible with the active ingredient of the formulation (e.g. a compound of the disclosure). It is understood by those of ordinary skill in this art that the terms "pharmaceutical formulation" and "pharmaceutical composition" are generally interchangeable, and they are so used for the purposes of this application and include preparations suitable for administration to mammals, e.g., humans.

A "pharmaceutical composition" as used herein relates to a formulation containing a compound of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds such as by producing any undesirable biological effect or otherwise interacting in a deleterious manner with any other component(s) of the pharmaceutical composition, its use is contemplated to be within the scope of this disclosure. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. "Pharmaceutically acceptable excipient or carrier" also relates to an excipient or carrier that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The compounds disclosed herein include the compounds themselves, as well as their salts, their solvates, and their prodrugs, if applicable. A salt, for example, can be formed between an anion and a positively charged group (e.g., protonated amino) on a compound of this disclosure. Suitable anions include chloride, bromide, iodide, sulfate, hi sulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluroacetate). The term "pharmaceutically acceptable anion" refers to an anion suitable for forming a pharmaceutically acceptable salt. Likewise, a salt can also be formed between a cation and a negatively charged group (e.g., carboxylate) on a compound of this disclosure. Suitable cations include sodium ion, potassium ion, magnesium ion, calcium ion, and an ammonium cation such as tetramethylammonium ion. The compounds of this disclosure also include those salts containing quaternary nitrogen atoms. Examples of prodrugs include esters and other pharmaceutically acceptable derivatives, which, upon administration to a subject, are capable of providing active compounds of this disclosure.

Additionally, physiologically acceptable, i.e. pharmaceutically compatible, salts can be salts of the compounds disclosed herein with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid.

Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine.

As used herein, "pharmaceutically acceptable salts" can refer to derivatives of the compounds of the present disclosure wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxy ethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, sub acetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts can include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, or an alkaline earth metal ion, e.g., an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The compounds of the present disclosure can also be prepared as prodrugs. In certain embodiments, one or more compounds of the present disclosure are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry* A Biochemical Approach, Oxford University Press, New York, pages 388-392).

Additionally, the compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

Some of the compounds of the present disclosure may exist in unsolvated as well as solvated forms such as, for example, hydrates.

"Solvate" means a solvent addition form that contains either a stoichiometric or non-stoichiometric amounts of solvent. Some compounds can have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the disclosure.

The disclosure also includes metabolites of the compounds described herein. Metabolites from chemical compounds, whether inherent or pharmaceutical, are formed as part of the natural biochemical process of degrading and eliminating the compounds. The rate of degradation of a compound is an important determinant of the duration and intensity of its action. Profiling metabolites of pharmaceutical compounds, drug metabolism, is an important part of drug discovery, leading to an understanding of any undesirable side effects.

As used herein, the term "treat," "treating," or "treatment" means decreasing the symptoms, markers, and/or any negative effects of a condition in any appreciable degree in a patient who currently has the condition. In some embodiments, treatment may be administered to a subject who exhibits only early signs of the condition for the purpose of decreasing the risk of developing the disease, disorder, and/or condition.

As used herein, the term "prevent," "prevention," or "preventing" refers to any method to partially or completely prevent or delay the onset of one or more symptoms or features of a disease, disorder, and/or condition. Prevention treatment may be administered to a subject who does not exhibit signs of a disease, disorder, and/or condition.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. As used herein, "therapeutically effective amount" can also mean that amount necessary to make a clinically observed improvement in the patient. In some embodiments, the composition is formulated such that it comprises an amount that would not cause one or more unwanted side effects. An effective amount of a pharmaceutical agent can also mean that which provides an objectively identifiable improvement as noted by the clinician or other qualified observer. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, "subject" means a human or animal (in the case of an animal, more typically a mammal). In one aspect, the subject is a human. In one aspect, the subject is a male. In one aspect, the subject is a female.

The compounds of the present disclosure can also be prepared as esters, for example, pharmaceutically acceptable esters. For example, a carboxylic acid function group in a compound can be converted to its corresponding ester, e.g., a methyl, ethyl or other ester. Also, an alcohol or hydroxyl group in a compound can be converted to its corresponding ester, e.g., acetate, propionate, or other esters.

The present disclosure includes new compounds generally represented by Formula I, Formula IA, Formula IB, or Formula II, or pharmaceutically acceptable salts thereof, and methods for preparation and uses thereof.

Throughout the description, where compositions are described as having, including, or comprising specific components, it is contemplated that compositions also consist essentially of, or consist of, the recited components.

Compounds

In one aspect, the present disclosure relates to compounds of Formula I:

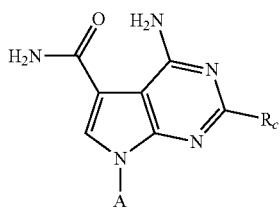
(I)

and pharmaceutically acceptable enantiomers, diastereomers, racemates, mixtures, solvates or salts thereof, wherein $R_c$ and A are as defined above.

In one or more embodiments of Formula I, Formula IA or Formula IB, A is selected from A1 through A14, wherein R can be $R^I$ $R^{IA}$, or $R^{IB}$:

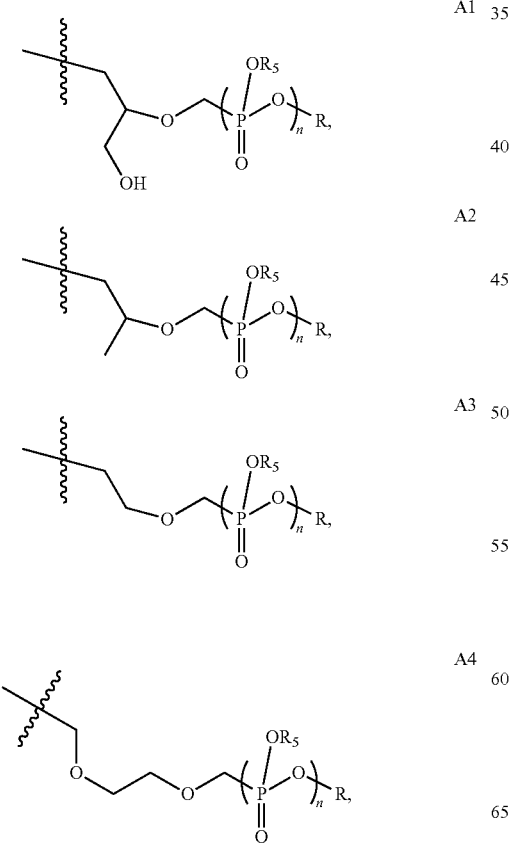

A1

A2

A3

A4

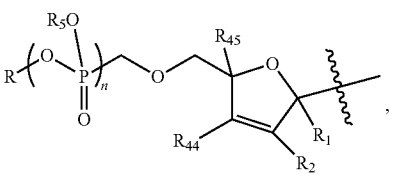
A5

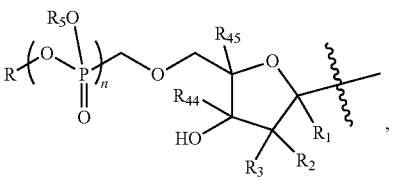
A6

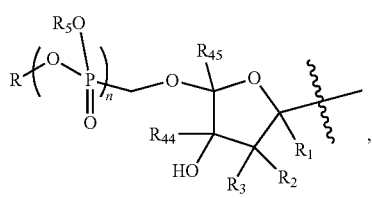
A7

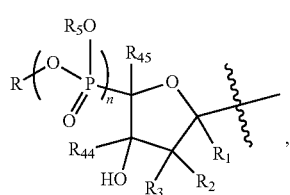
A8

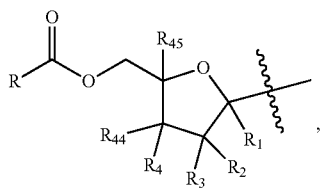
A9

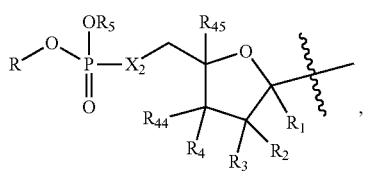
A10

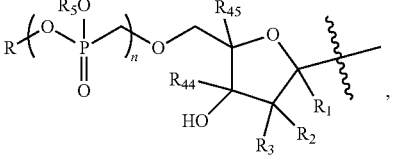
A11

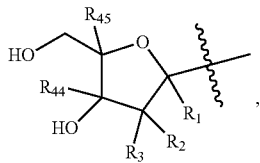
A12

-continued

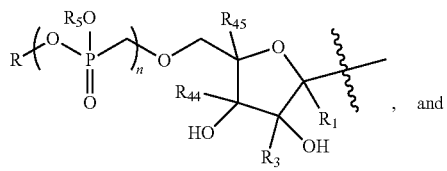, and A13

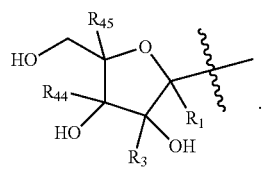 A14

In one or more embodiments of Formula I, Formula IA or Formula IB, A is selected from A1 through A14, wherein R can be $R^I$ $R^{IA}$, or $R^{IB}$:

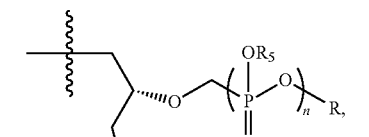,

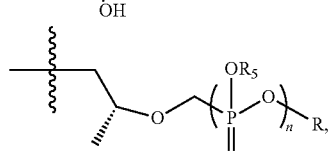,

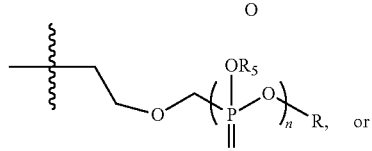, or

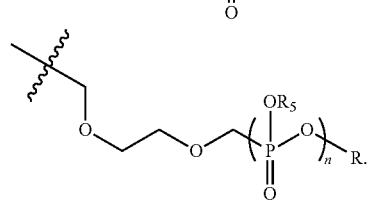.

In one or more embodiments of Formula I, Formula IA or Formula IB, A is selected from A1 through A14, wherein R can be $R^I$ $R^{IA}$, or $R^{IB}$:

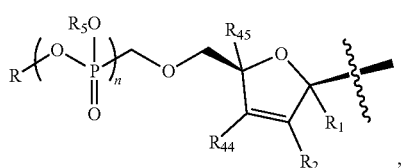,

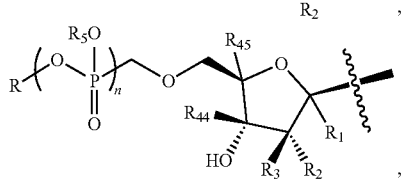,

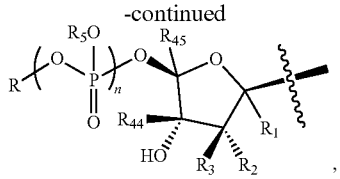,

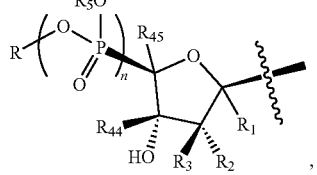,

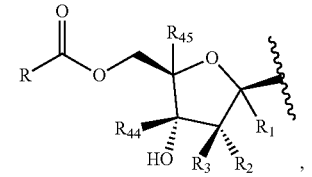,

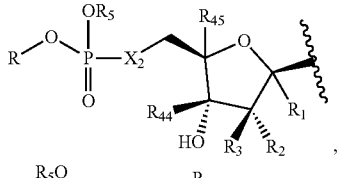,

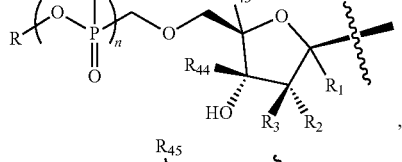,

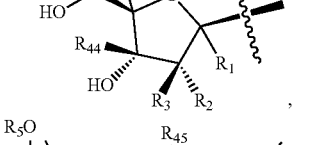,

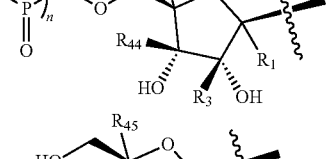,

, and

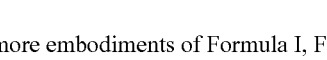,

In one or more embodiments of Formula I, Formula IA or Formula IB, A is

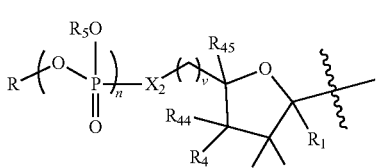, wherein R can be $R^I$ or $R^{IA}$.

In one or more embodiments of Formula I, Formula IA or Formula IB, A is

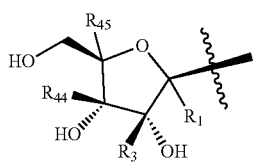

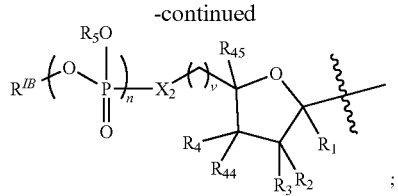

wherein R can be $R^I$ or $R^{IA}$.

In one or more embodiments, compounds of Formula I can have one or more of the following features. $R_4$ is H, substituted or unsubstituted $C_1$-$C_6$, alkyl, $NH_2$, OH, or SH. $R_4$ can be $C_1$-$C_6$ alkyl optionally substituted with one or more halogens. $R_4$ can be methyl, $CH_2X$, $CHX_2$ or $CX_3$, wherein X is halogen. $R_4$ can be pentyl. $R_1$ can be hydrogen, $R_2$ and $R_3$ can each independently be hydrogen, $CH_3$, $CH_2X$, $CHX_2$, $CX_3$, $N_3$, OH, or $NH_2$, wherein X is halogen. $R_5$ can be H, M, $C_1$-$C_6$ alkyl, phenyl, or benzyl. $M^+$ can be $Na^+$, $Li^+$, $K^+$, $Ca^{2+}$, $Mg^{2+}$, or $NR_gR_dR_eR_f^+$, wherein $R_g$, $R_d$, $R_e$ and $R_f$ are each independently hydrogen or $C_{1-5}$ alkyl. $R^I$ can be H. When $X_2$ is absent, v can be 0. $R_1$ can be hydrogen. $R_{45}$ can be hydrogen. $R_c$ can be $C_1$-$C_6$ alkyl, e.g., methyl.

In one or more embodiments, of the compounds of Formula I, or Formula IA, $R_1$ is —H. In one or more embodiments, $R_2$ is —OH. In one or more embodiments, $R_4$ is —OH. In one or more embodiments, $R_2$ and $R_4$ are each —OH. In one or more embodiments, $R_3$ is —H. In one or more embodiments, $R_{44}$ is —H. In one or more embodiments, $R_3$ and $R_{44}$ are each —H. In one or more embodiments, $R^{IA}$ is —H. In one or more embodiments $R_c$ is —$CH_3$. In one or more embodiments, v is 1, $X_2$ is —O—, n is 0, and $R^I$ is —H. In one or more embodiments, v is 1, $X_2$ is —O—, n is 0, and $R^{IA}$ is —H.

In one or more embodiments of the compounds of Formula II, $R^a$ and $R^b$ are both —H. In one or more embodiments, $R^c$ is —H. In one or more embodiments, n is 0. In one or more embodiments, $R^{II}$ is —H. In one or more embodiments, $R^a$, $R^b$, and $R^c$ are —H. In one or more embodiments, $R^a$, $R^b$, and $R^c$ are —H and n is 0. In one or more embodiments, $R^a$, $R^b$, and $R^c$ are —H. In one or more embodiments, $R^a$, $R^b$, and $R^c$ are —H, n is 0 and $R^{II}$ is —H.

In one or more embodiments, the present disclosure provides a compound of Formula IB:

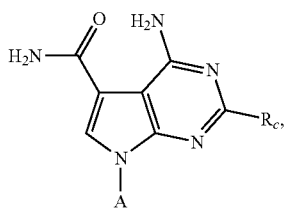

(Formula IB)

and pharmaceutically acceptable salts, solvates, enantiomers, diastereomers, racemates or mixtures thereof, wherein:

A is:

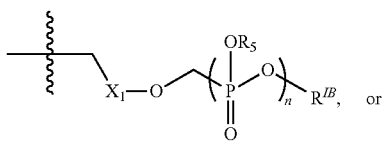

$X_1$ is —$CR_{11}R_{12}$— or —$OCH_2CH_2$— wherein the oxygen atom is distal to the $R^{IB}$ moiety in A;

$R_{11}$ and $R_{12}$ are independently hydrogen or $C_1$-$C_4$ alkyl, wherein the alkyl is optionally substituted with one or more halogen, —OH, —SH, or —$NH_2$;

$X_2$ is absent, —O—, —C(O)O, or —$OCH_2$— wherein the oxygen atom is distal to the $R^{IB}$ moiety in A;

each $RI^B$ independently is hydrogen, —$C_1$-$C_6$ alkyl,

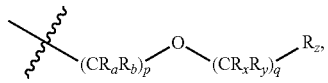

or $R^{IB}$ is an amino acid residue bound via the carbonyl group, wherein the alkyl is optionally substituted with one or more halogen, —OH, —SH, or —$NH_2$;

v is 0 or 1;

n is 0, 1, 2, or 3 and when $X_2$ is —C(O)O, n is 0;

p is 2, 3, 4, 5, 6, 7, 8, 9, 10, or 11;

q is 1, 2, 3, 4, 5, 6, 7, 8, 9, 10, 11, 12, 13, 14, 15, 16, 17, or 18;

$R_z$ is hydrogen, halogen, —$C_1$-$C_4$ alkylthio, —$C_1$-$C_4$ alkoxy, —$C_1$-$C_4$ alkyl, —$C_2$-$C_4$ alkenyl, —$C_2$-$C_4$ alkynyl, aryl, heteroaryl, —$C_3$-$C_8$ cycloalkyl, —$C_4$-$C_8$ cycloalkenyl, or 3- to 5-membered nonaromatic heterocycle, wherein each alkylthio, alkoxy, alkyl, alkenyl, alkynyl, aryl, heteroaryl, cycloalkyl, cycloalkenyl, or heterocycle is optionally substituted with one or more halogen, —OH, —SH, or —$NH_2$;

$R_a$, $R_b$, $R_x$, and $R_y$ are each independently selected from the group consisting of hydrogen, halogen, —OH, —SH, —$C_1$-$C_6$ alkoxy, aryloxy, —$C_1$-$C_6$ alkylthio, arylthio, —OC(O)$C_1$-$C_6$ alkyl, —OC(O)aryl, —$C_1$-$C_6$ alkyl, —$C_2$-$C_6$ alkenyl, —$C_2$-$C_6$ alkynyl, aryl, heteroaryl, —$C_3$-$C_8$ cycloalkyl, and —$C_4$-$C_8$ cycloalkenyl, wherein each alkoxy, aryloxy, alkylthio, arylthio, alkyl, aryl, alkenyl, alkynyl, heteroaryl, cycloalkyl, or cycloalkenyl is optionally substituted with one or more halogen, —OH, —SH, or —$NH_2$;

or any two $R_a$ or $R_b$, together with the atom to which they are both attached, can combine to form a $C_3$-$C_8$ spirocycloalkyl or 3- to 8-membered spiroheterocycle;

or any two $R_a$ or $R_b$, when on adjacent atoms, can combine to form a cis- or trans-carbon-carbon double bond or a carbon-carbon triple bond;

or any two $R_a$ or $R_b$, when on adjacent atoms, can combine to form an aryl, heteroaryl, —$C_3$-$C_{10}$cycloalkyl, —$C_4$-$C_{10}$cycloalkenyl, or 5- to 10-membered ring heterocycle;

or any $CR_aR_b$ can be replaced by —O—, —S—, —S(O)—, or —$SO_2$—;

or any two $R_x$ or $R_y$, together with the atom to which they are both attached, can combine to form a —$C_3$-$C_8$ spirocycloalkyl or 3- to 8-membered spiroheterocycle;

or any two $R_x$ or $R_y$, when on adjacent atoms, can combine to form a cis- or trans-carbon-carbon double bond or a carbon-carbon triple bond;

or any two $R_x$ or $R_y$, when on adjacent atoms, can combine to form an aryl, heteroaryl, —$C_3$-$C_{10}$cycloalkyl, —$C_4$-$C_{10}$cycloalkenyl, or 5- to 10-membered ring heterocycle;

or any $CR_xR_y$ can be replaced by —O—, —S—, —S(O)—, or —$SO_2$—;

$R_1$ and $R_{45}$ are each independently hydrogen, halogen, —$N_3$, —OH, —$NH_2$, —SH, —$C_1$-$C_6$ alkyl, —$C_3$-$C_6$ cycloalkyl, —$C_1$-$C_6$ alkenyl, —$C_4$-$C_8$ cycloalkenyl, —$C_1$-$C_6$ alkynyl, —$C_8$-$C_{12}$ cycloalkynyl, —$C_1$-$C_6$ alkoxy, or —$C_1$-$C_6$ alkylthio wherein each alkyl, cycloalkyl, alkenyl, cycloalkenyl, alkynyl, cycloalkynyl, alkoxy or alkylthio is indepdendently substituted with one or more halogen, —$N_3$, —OH, —$NH_2$, or —SH;

$R_2$, $R_3$, $R_4$ and $R_{44}$ are each independently hydrogen, halogen, —$N_3$, —OH, —$NH_2$, —SH, —$C_1$-$C_6$ alkyl, —$C_1$-$C_6$ alkoxy, or —$C_1$-$C_6$ alkylthio, wherein each alkyl, alkoxy, or alkylthio is optionally substituted with one or more halogen, —$N_3$, —OH, —$NH_2$, or —SH;

or $R_3$ and one of $R_4$ and $R_{44}$, together with the atoms to which they are attached can form a carbon-carbon double bond;

$R_5$ is independently hydrogen, —$R^{IB}$, $M^+$, aryl, aralkyl, —$C_1$-$C_6$, alkyl, —$C_1$-$C_6$ heteroalkyl, cycloalkyl, non-aromatic heterocyclic ring, or heteroaryl, wherein $M^+$ is a cation and wherein each aryl, aralkyl, alkyl, heteroalkyl, cycloalkyl, heterocycle, or heteroaryl is optionally substituted with one or more halogen, —$N_3$, —OH, —$NH_2$, or —SH, and wherein $R_5$ is not an amino acid; and $R_c$ is —$C_1$-$C_6$ alkyl, —$C_3$-$C_6$ cycloalkyl, —$C_1$-$C_6$ alkenyl, —$C_4$-$C_8$ cycloalkenyl, —$C_1$-$C_6$ alkynyl, —$C_8$-$C_{12}$ cycloalkynyl, or aryl, wherein each alkyl, cycloalkyl, alkenyl, cycloalkenyl, or aryl is optionally substituted with one or more halogen, —$N_3$, —OH, —$NH_2$, or —SH.

In one or more embodiments, $R^I$, $R^{IA}$, $R^B$, or $R^{II}$ is selected from:

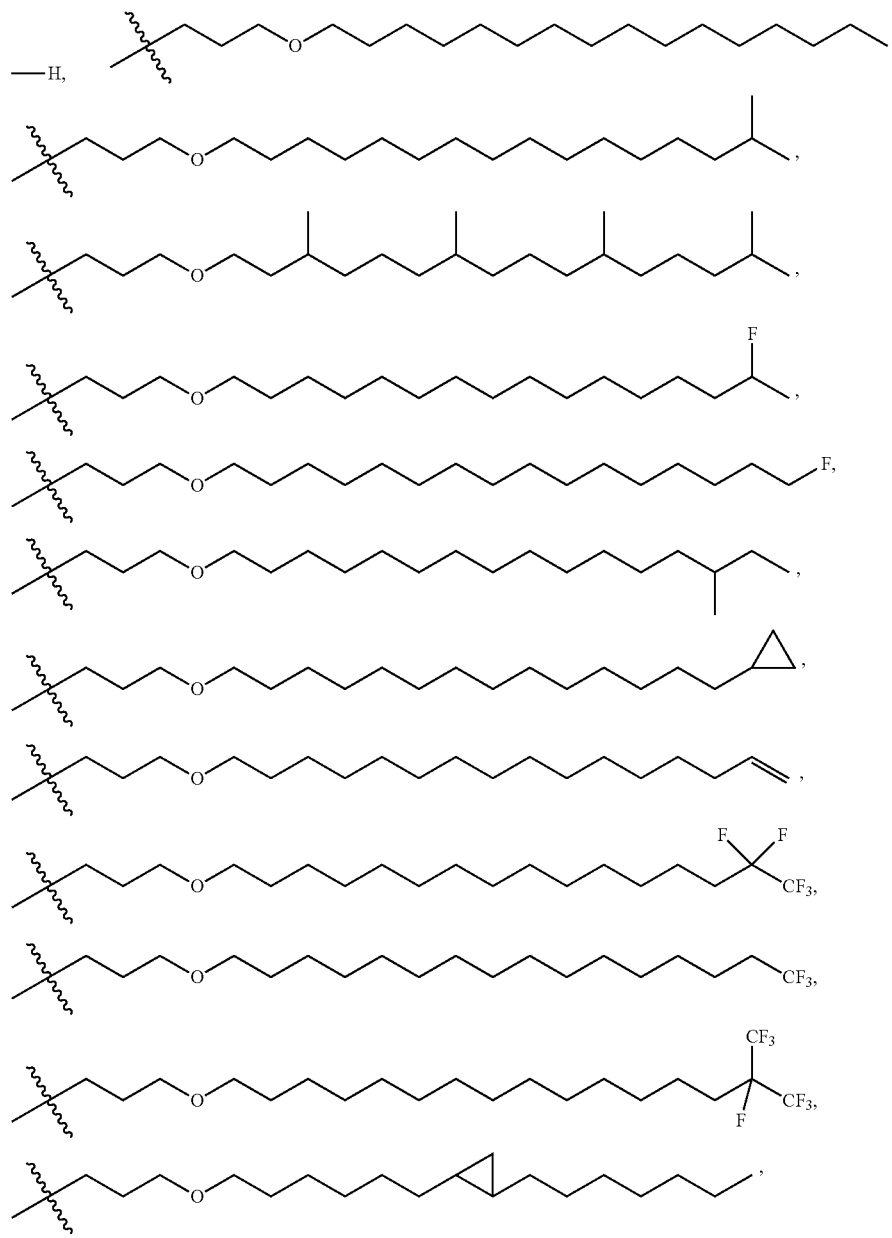

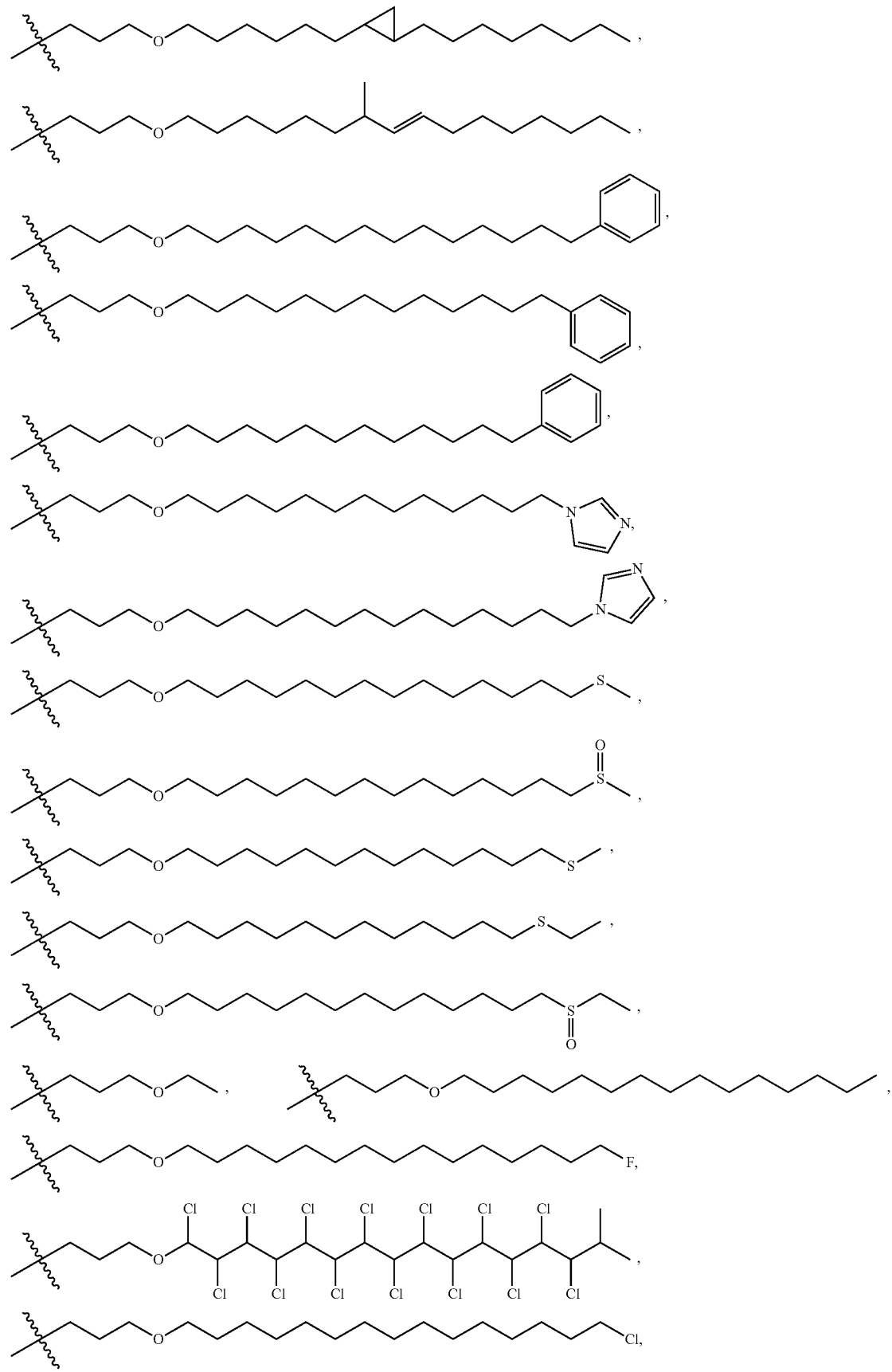

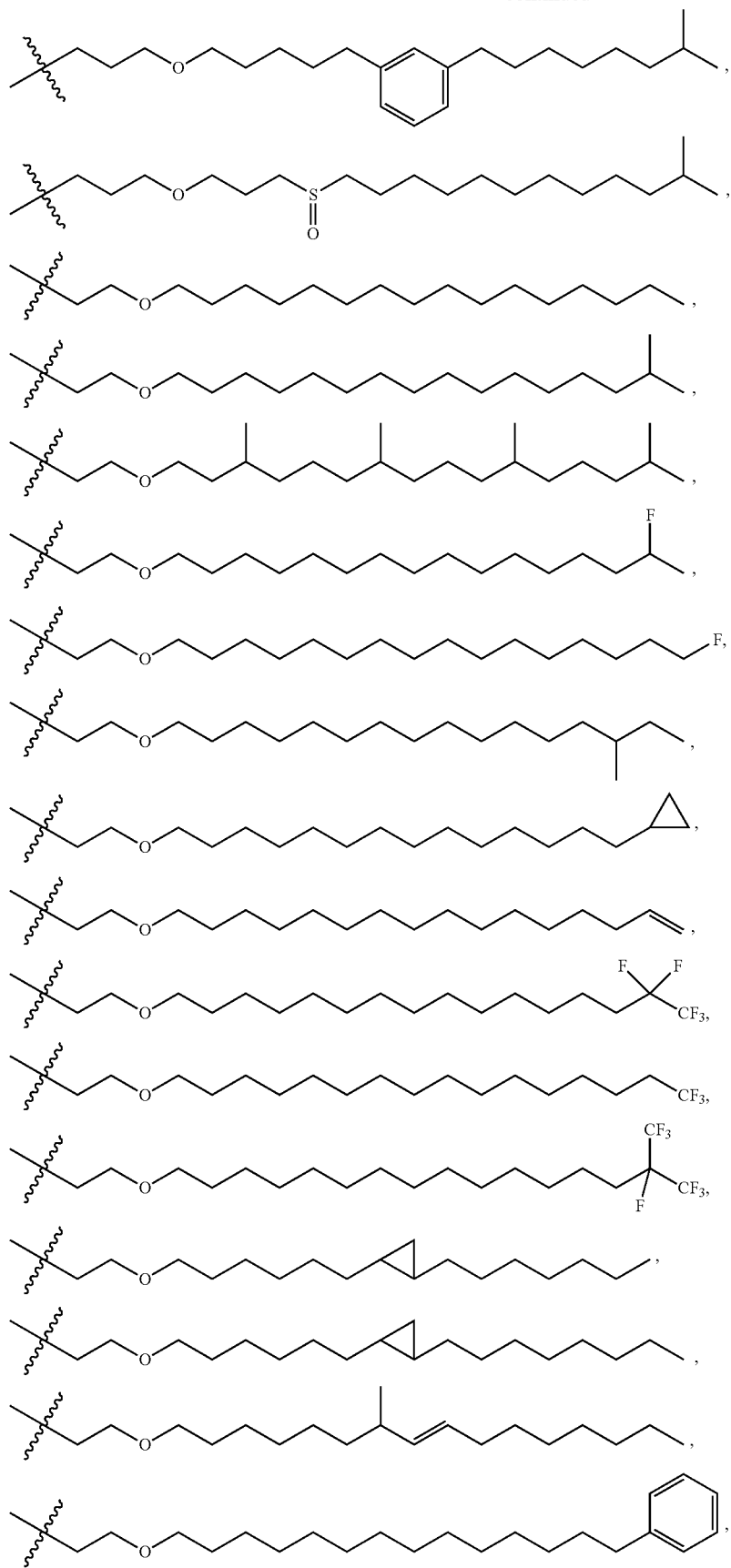

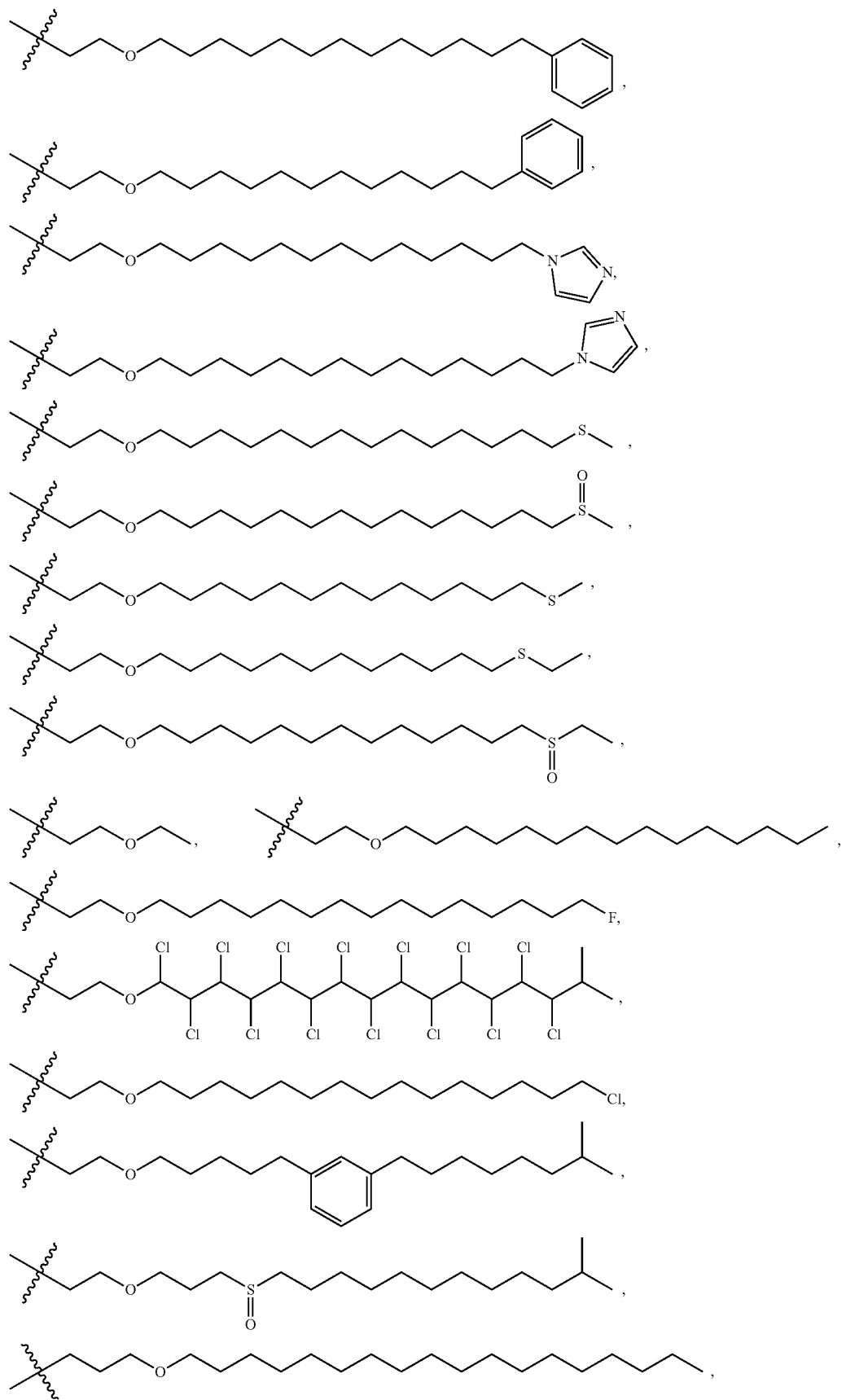

-continued
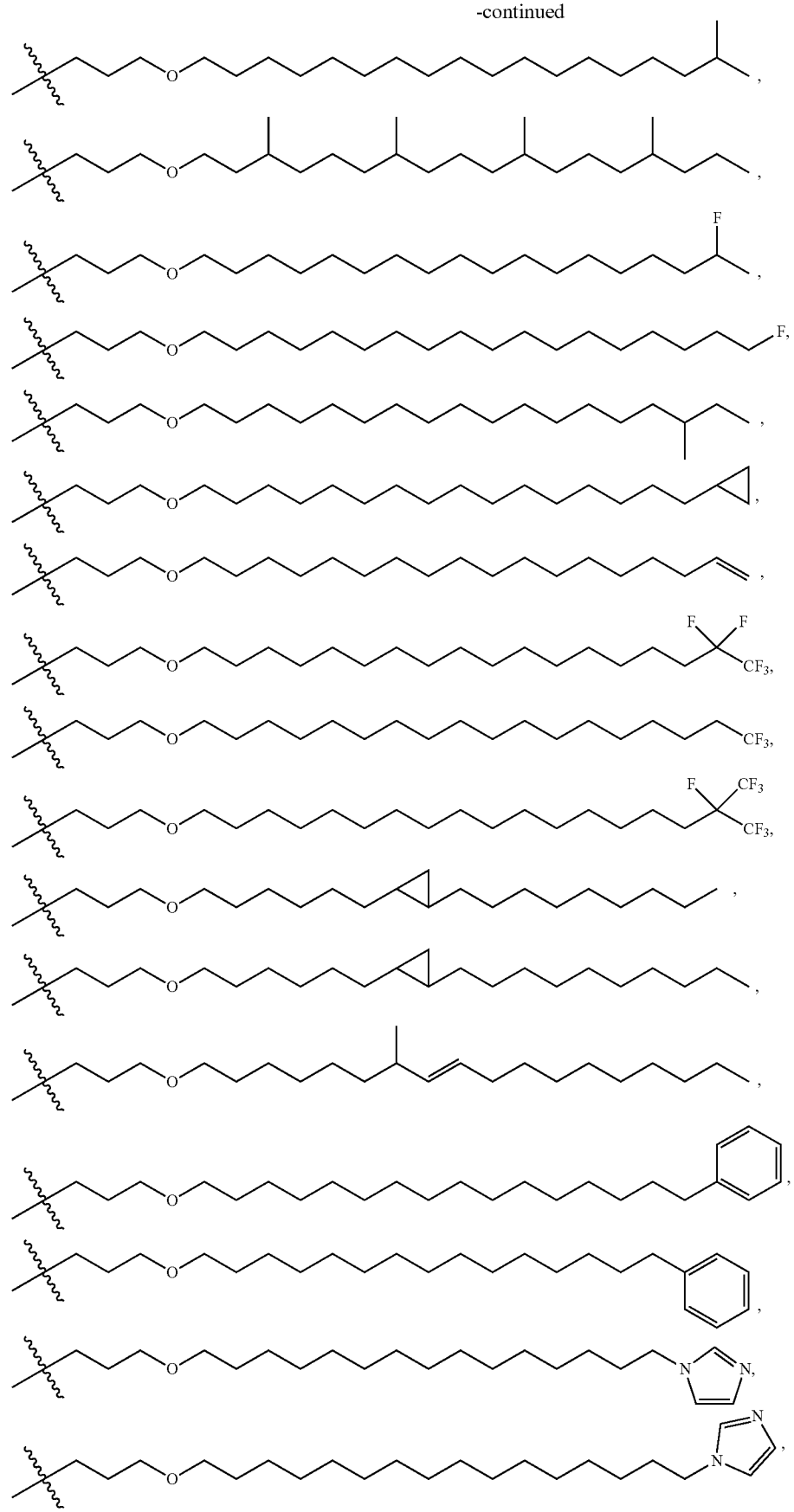

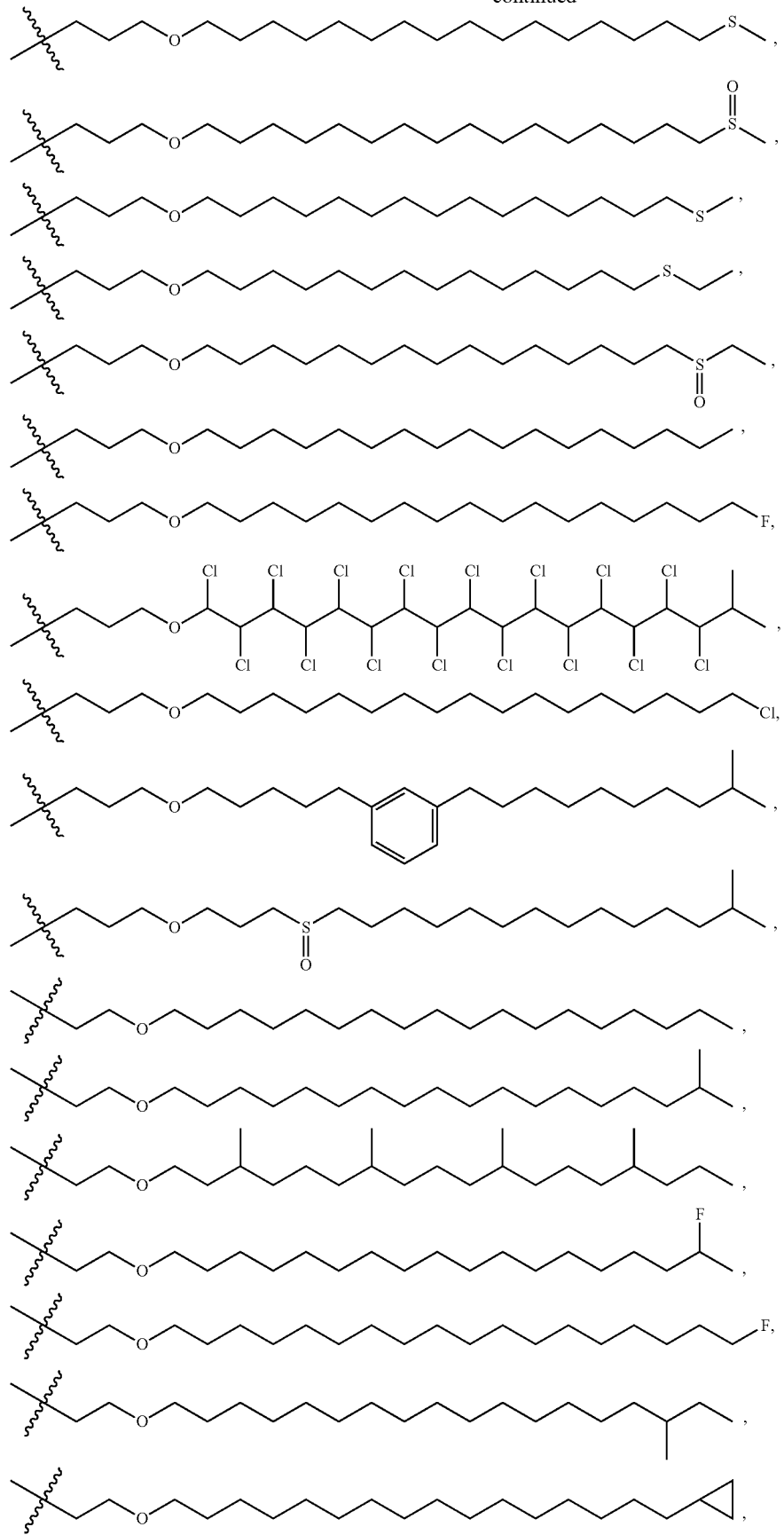

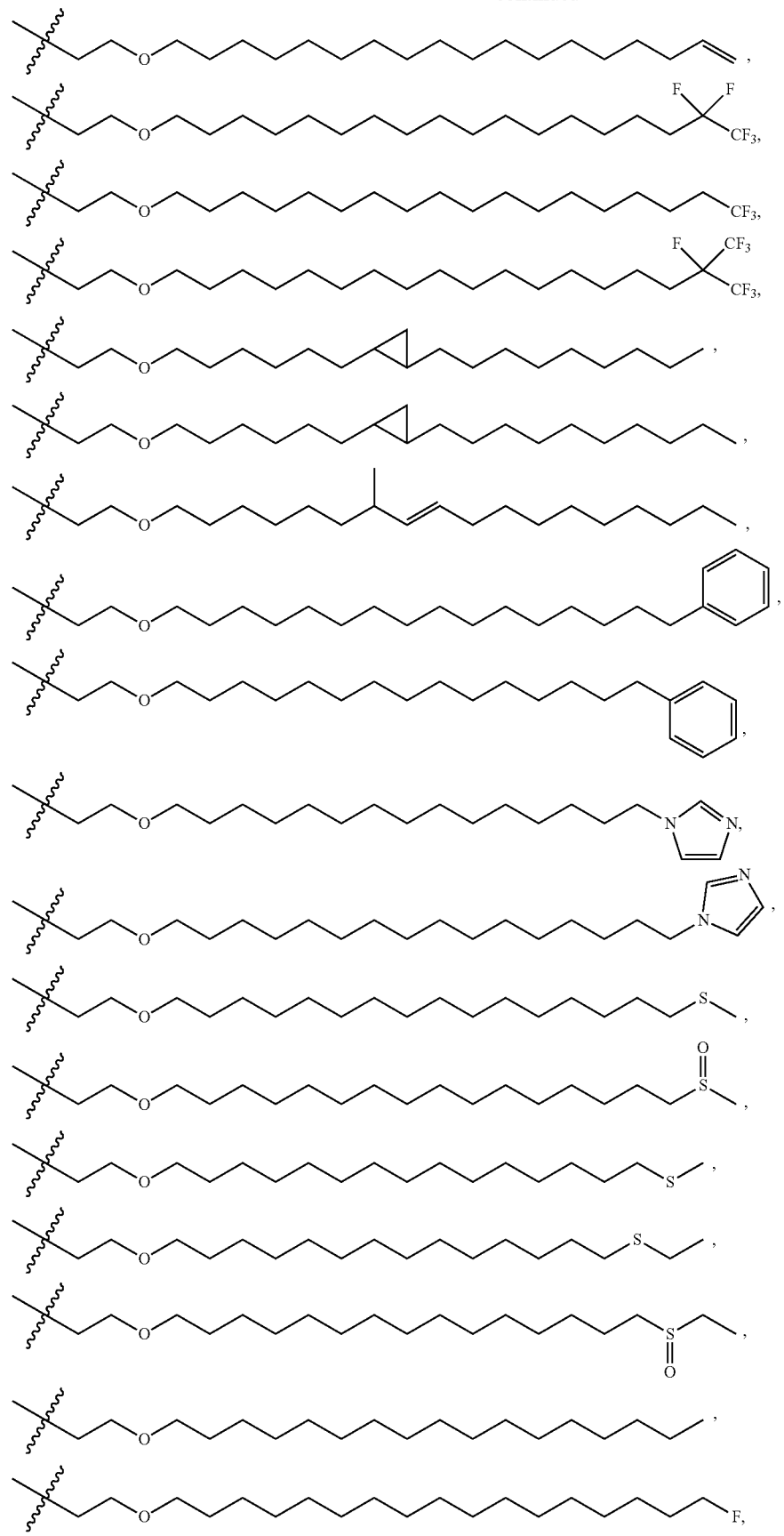

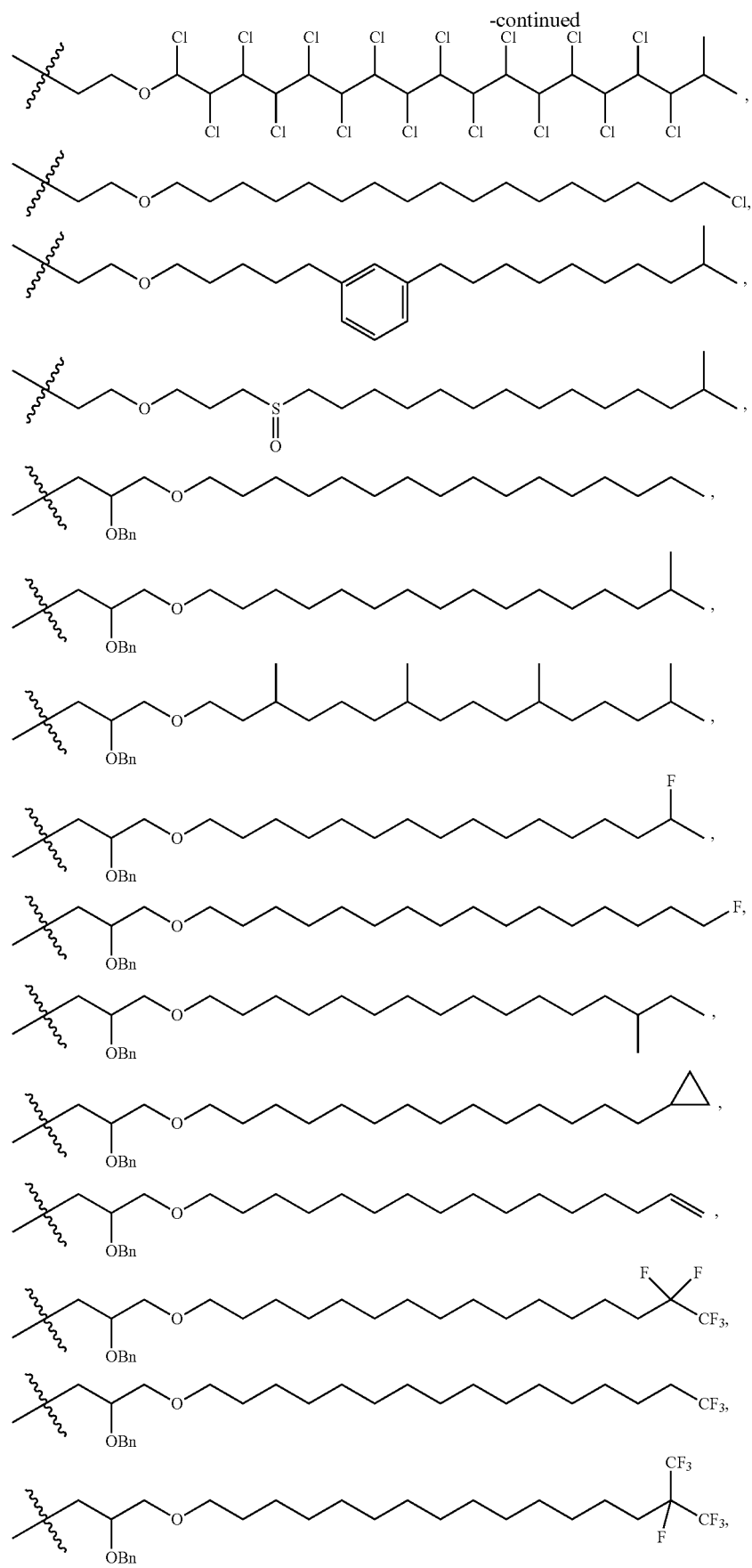

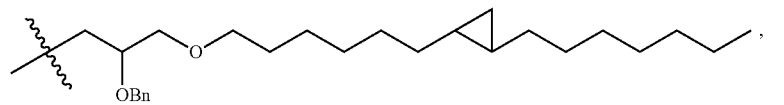
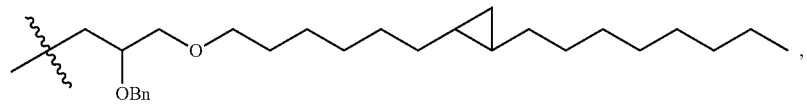
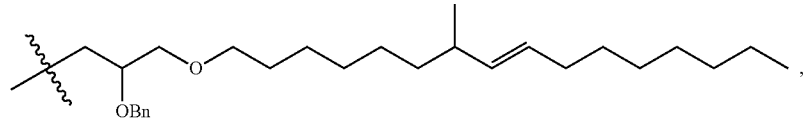
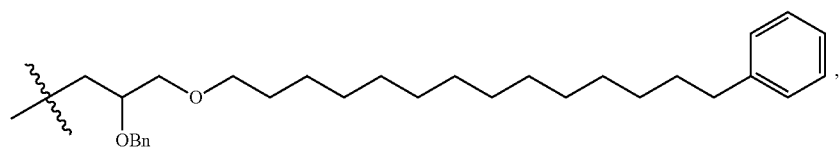
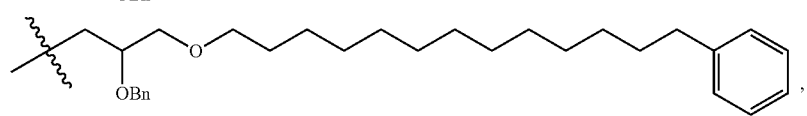
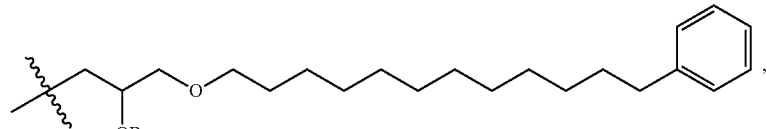
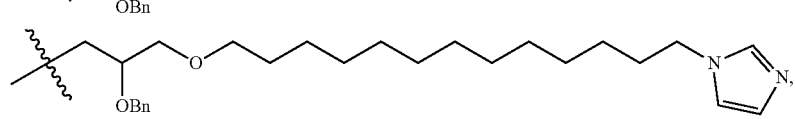
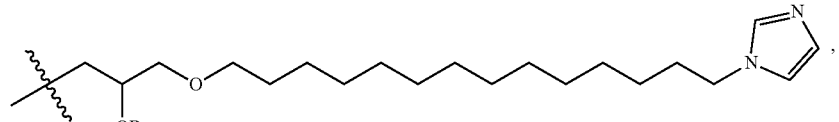
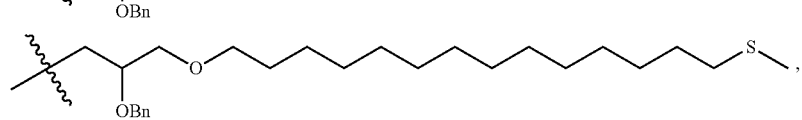
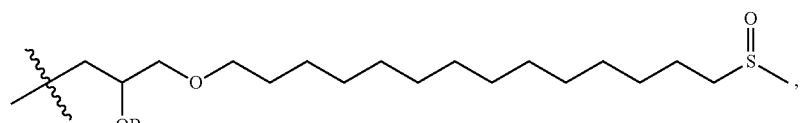
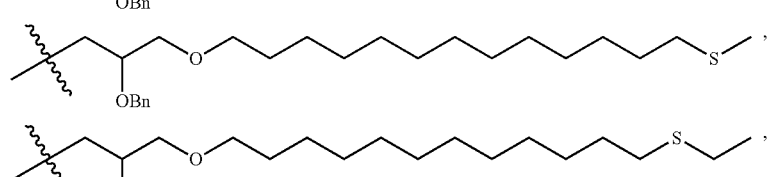
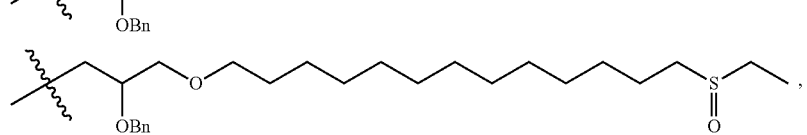
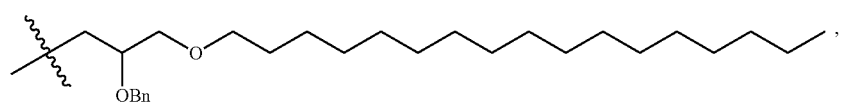
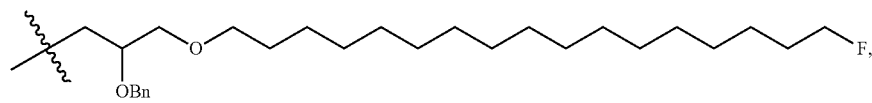
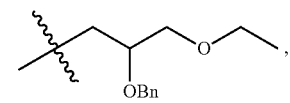

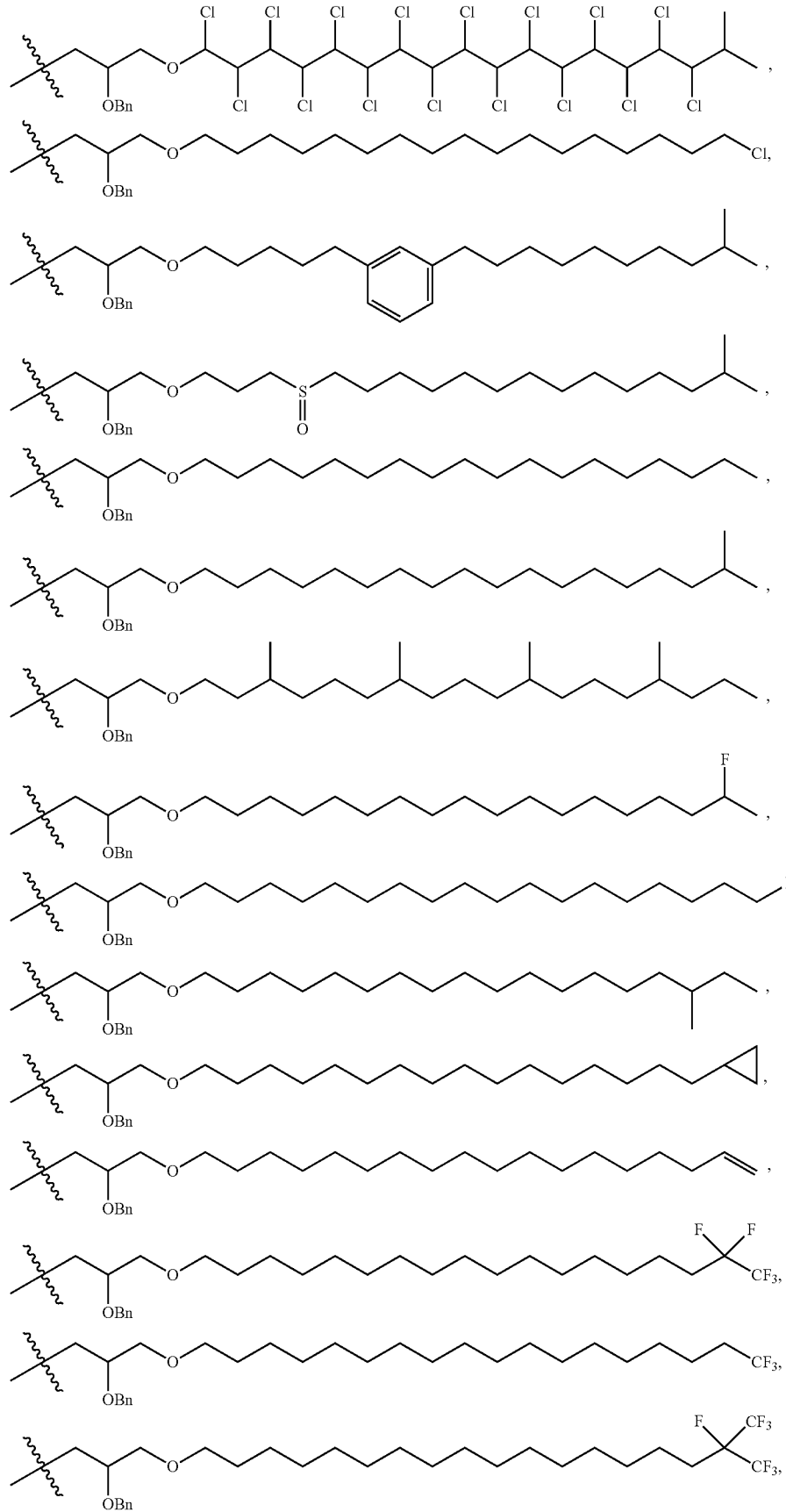

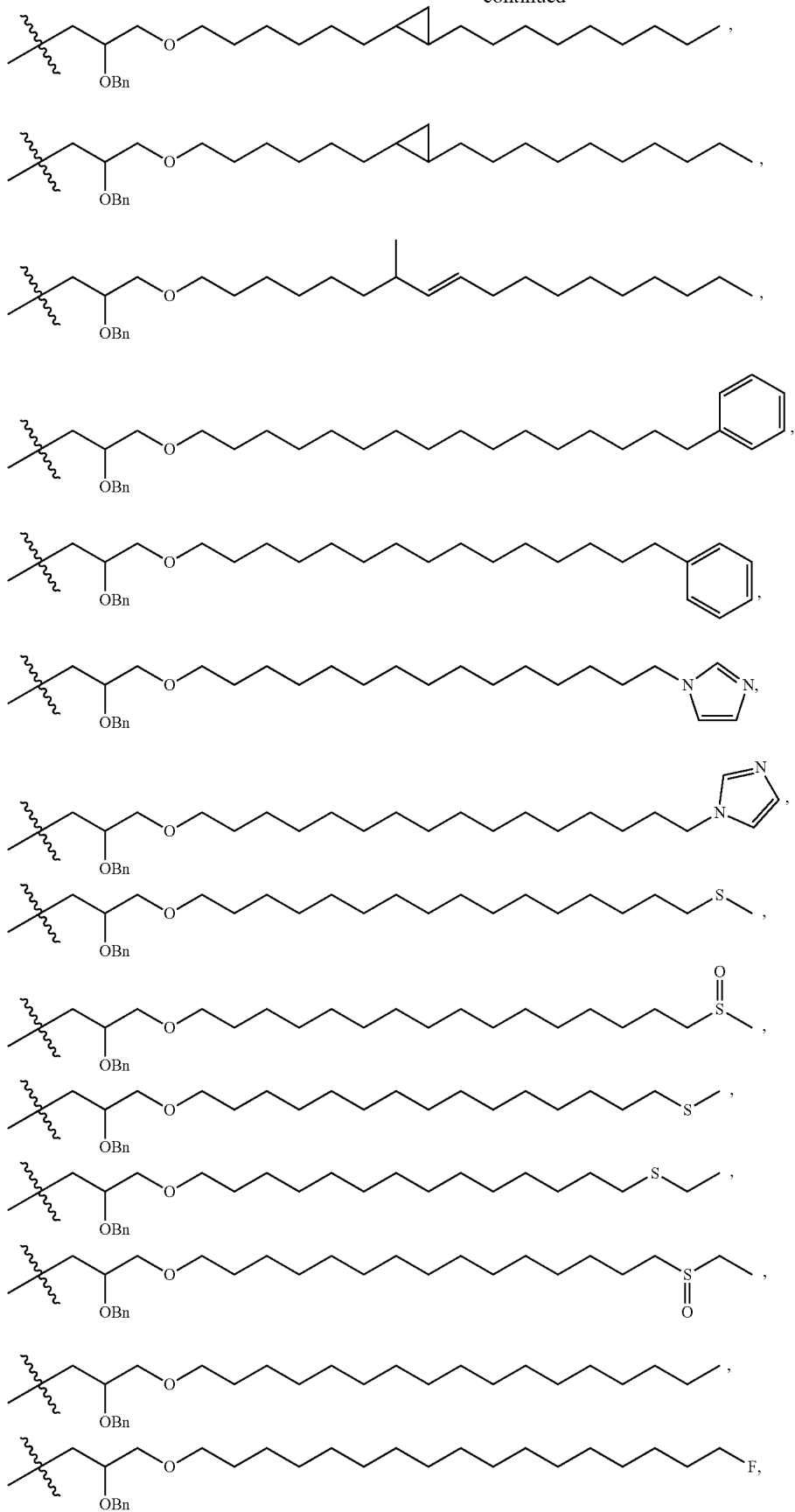

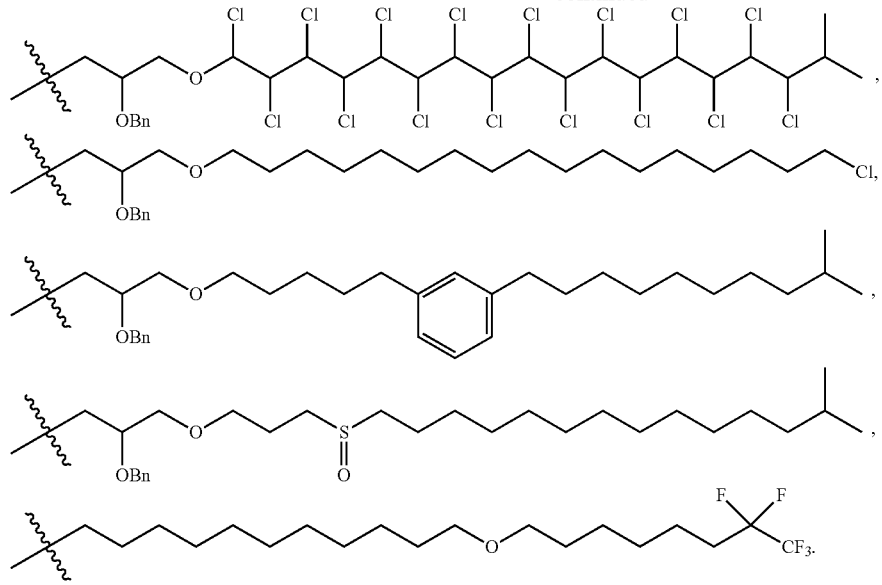

In one or more embodiments, the compound is of the Formula I-a:

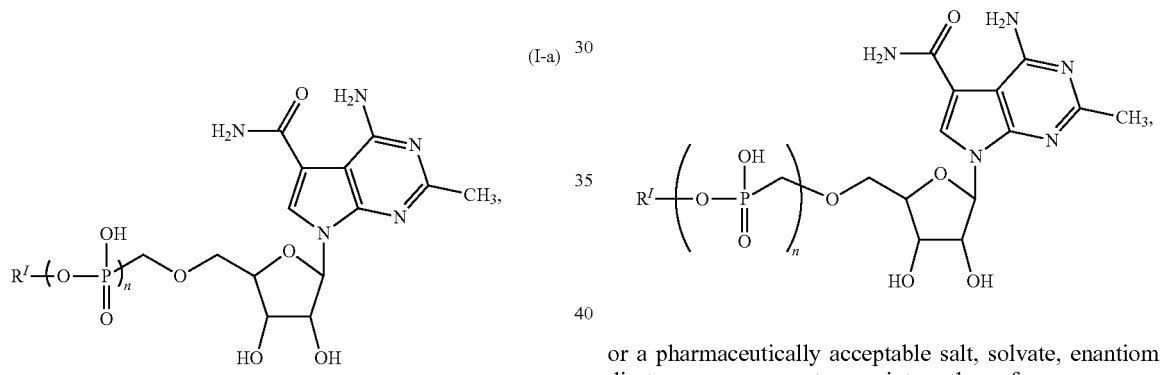

or a pharmaceutically acceptable salt, solvate, enantiomer, diastereomer, racemate or mixture thereof.

In one or more embodiments, the compound is of the Formula I-b:

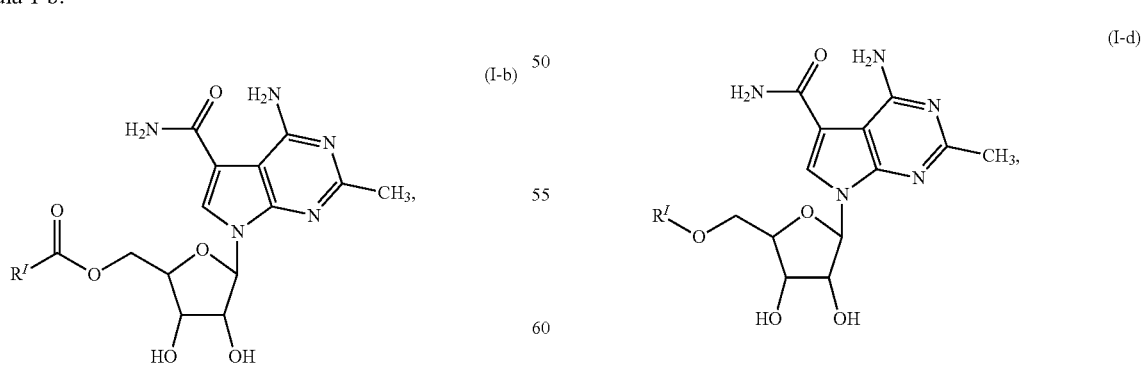

or a pharmaceutically acceptable salt, solvate, enantiomer, diastereomer, racemate or mixture thereof.

In one or more embodiments, the compound is of the Formula I-c:

or a pharmaceutically acceptable salt, solvate, enantiomer, diastereomer, racemate or mixture thereof.

In one or more embodiments, the compound is of the Formula I-d:

or a pharmaceutically acceptable salt, solvate, enantiomer, diastereomer, racemate or mixture thereof.

In one or more embodiments, the compound of the disclosure is:

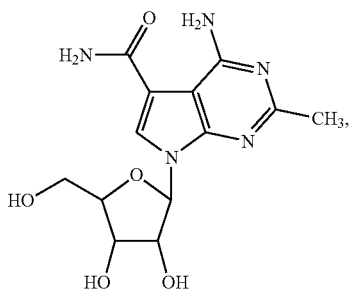 [SMILES: Cc1nc(N)c2c(C(N)=O)cn(C3OC(CO)C(O)C3O)c2n1]

or a pharmaceutically acceptable salt, solvate, enantiomer, diastereomer, racemate or mixture thereof.

In one or more embodiments, the compound of the disclosure is Compound 1:

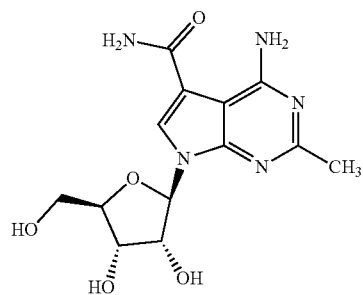 [SMILES: Cc1nc(N)c2c(C(N)=O)cn([C@@H]3O[C@H](CO)[C@@H](O)[C@H]3O)c2n1]

(Compound 1; 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide), or a pharmaceutically acceptable salt, solvate, enantiomer, diastereomer, racemate or mixture thereof.

In one or more embodiments, the compound of the disclosure is Compound 1-triphosphate (Compound 1-TP or Compound 1-PPP), or a pharmaceutically acceptable salt, solvate, enantiomer, diastereomer, racemate or mixture thereof:

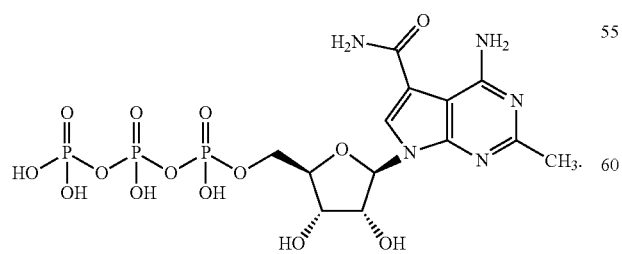

In one or more embodiments, the compound of the disclosure is selected from:

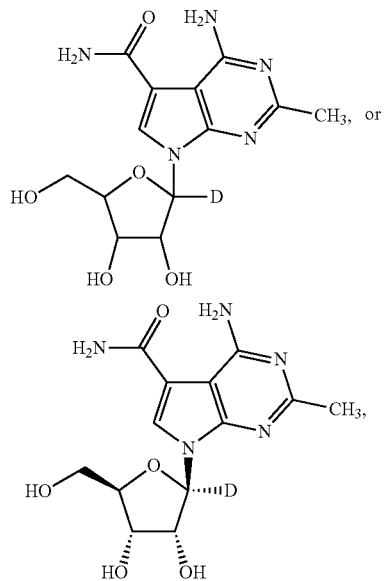

or a pharmaceutically acceptable salt, solvate, enantiomer, diastereomer, racemate or mixture thereof.

In one or more embodiments, the compound of the disclosure is selected from:

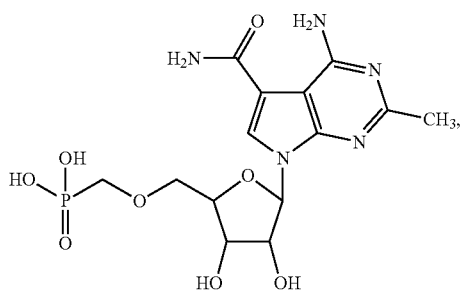

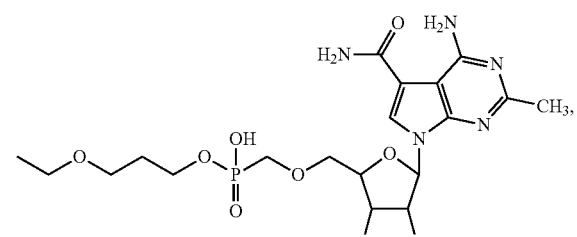

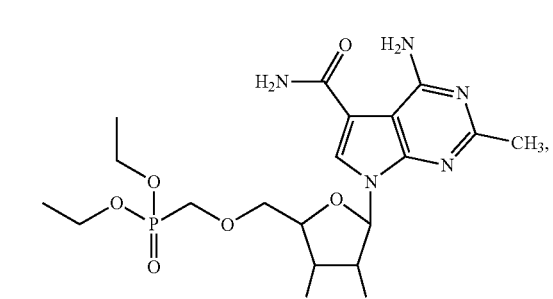

-continued

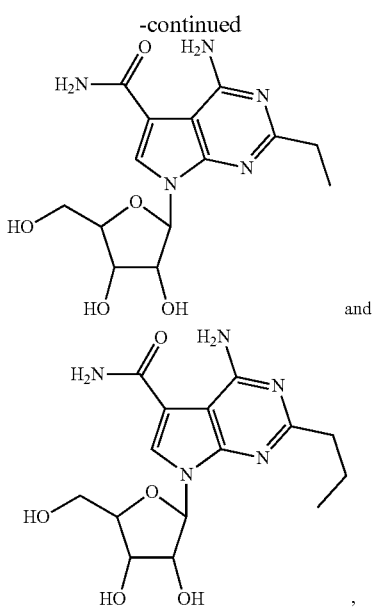

or a pharmaceutically acceptable salt, solvate, enantiomer, diastereomer, racemate or mixture thereof.

In one or more embodiments, the compound of the disclosure is selected from:

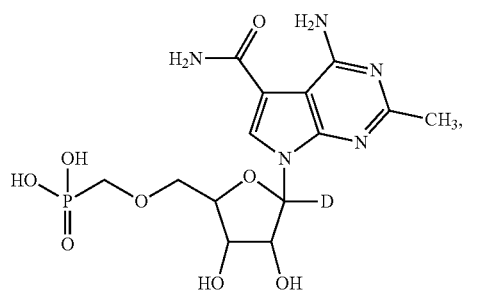

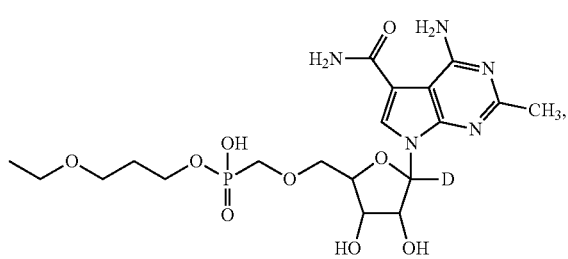

-continued

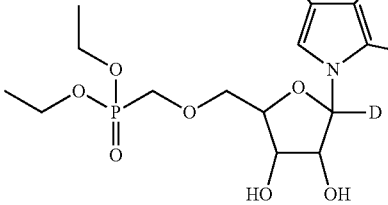

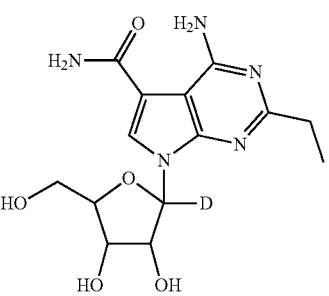

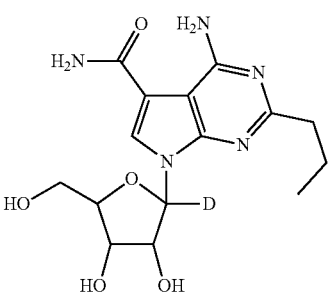

, or a pharmaceutically acceptable salt, solvate, enantiomer, diastereomer, racemate or mixture thereof.

In one or more embodiments, the compound of the disclosure is selected from:

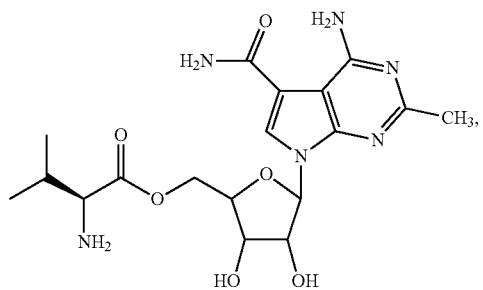
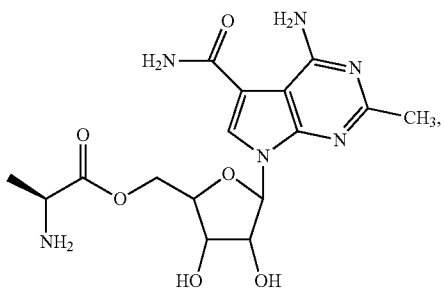

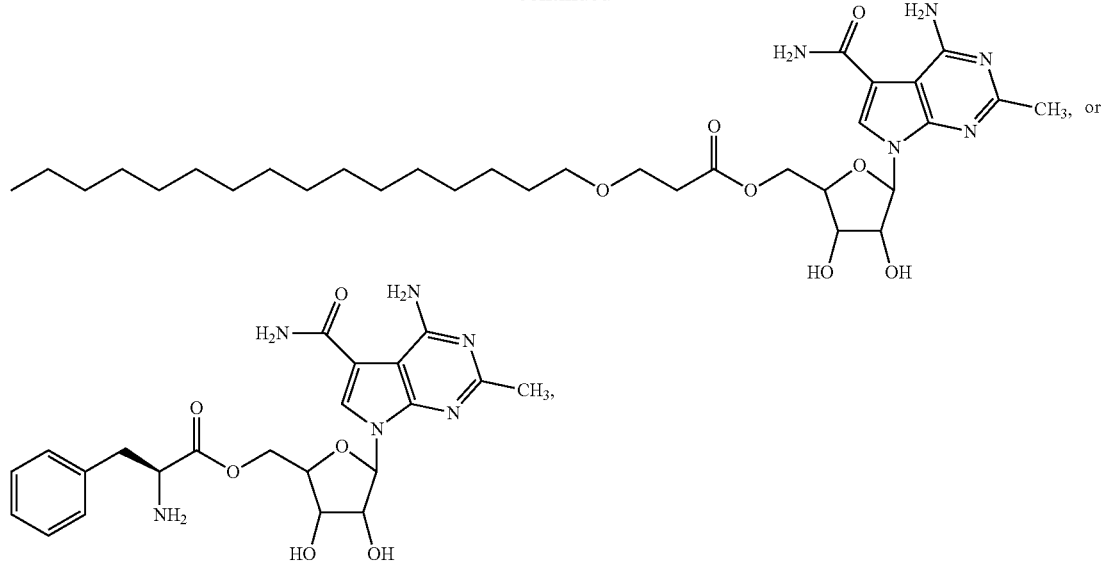
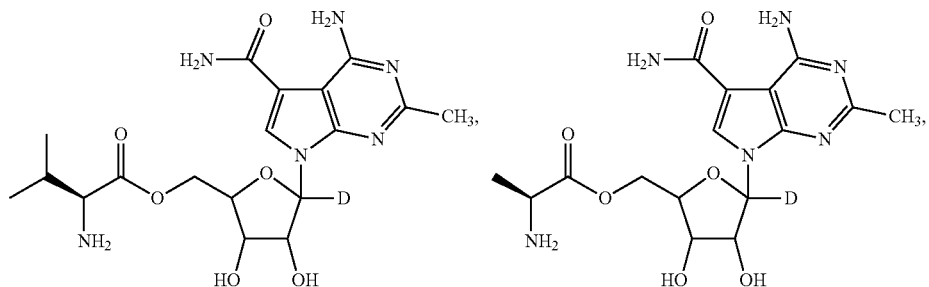
or a pharmaceutically acceptable salt, solvate, enantiomer, diastereomer, racemate or mixture thereof.
In one or more embodiments, the compound of the disclosure is selected from:
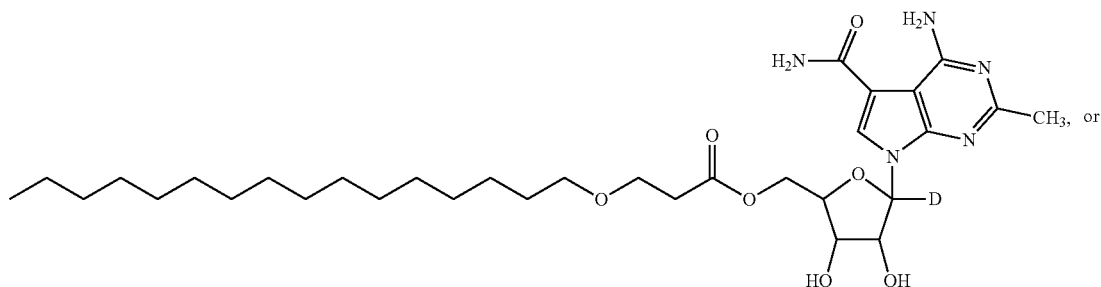
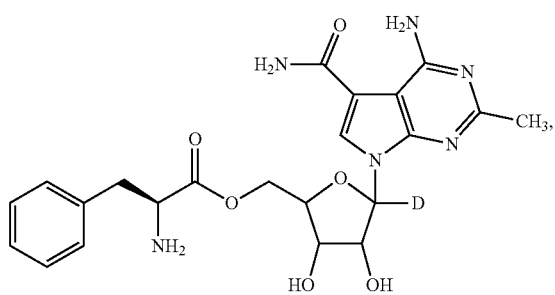

or a pharmaceutically acceptable salt, solvate, enantiomer, diastereomer, racemate or mixture thereof.

In some embodiments, the present disclosure provides the use of a compound as described herein, or a pharmaceutically acceptable salt, solvate, enantiomer, diastereomer, racemate or mixture thereof, in the manufacture of a medicament for treating a disease.

In some embodiments, the present disclosure provides the use of the compound

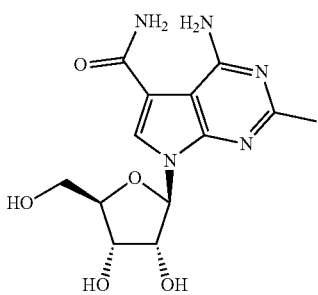 [SMILES: Cc1nc(N)c2c(C(N)=O)cn([C@@H]3O[C@H](CO)[C@@H](O)[C@H]3O)c2n1]

in the manufacture of a medicament for treating a disease. In some embodiments, the disease is a viral infection. In some embodiments, the viral infection is a norovirus.

In some embodiments, the present disclosure provides the use of a compound as described herein in the treatment of a disease.

In some embodiments, the present disclosure provides the use of the compound

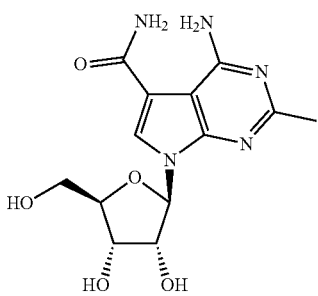 [SMILES: Cc1nc(N)c2c(C(N)=O)cn([C@@H]3O[C@H](CO)[C@@H](O)[C@H]3O)c2n1]

for the treatment of a disease. In some embodiments, the disease is a viral infection. In some embodiments, the viral infection is norovirus infection.

In some embodiments, the compound of the disclosure is selected from compound 1, 2, 3, 4, 5, 6, 71, 77, 76, 107, 111, 126, 133, 137, 139, 141, 143, or 145, or a pharmaceutically acceptable salt, solvate, enantiomer, diastereomer, racemate or mixture thereof, or any combination thereof.

Methods of Synthesis

The compounds of the present disclosure may be made by a variety of methods, including standard chemistry. Suitable synthetic routes are depicted in the schemes given below.

The compounds described herein (e.g., compounds of Formula I, Formula IA, Formula IB, or Formula II) may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I, Formula IA, Formula IB, or Formula II Those skilled in the art will recognize if a stereocenter exists in the compounds of Formula I, Formula IA, Formula IB, or Formula II. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Scheme 1: General Synthesis of Compounds of the Invention

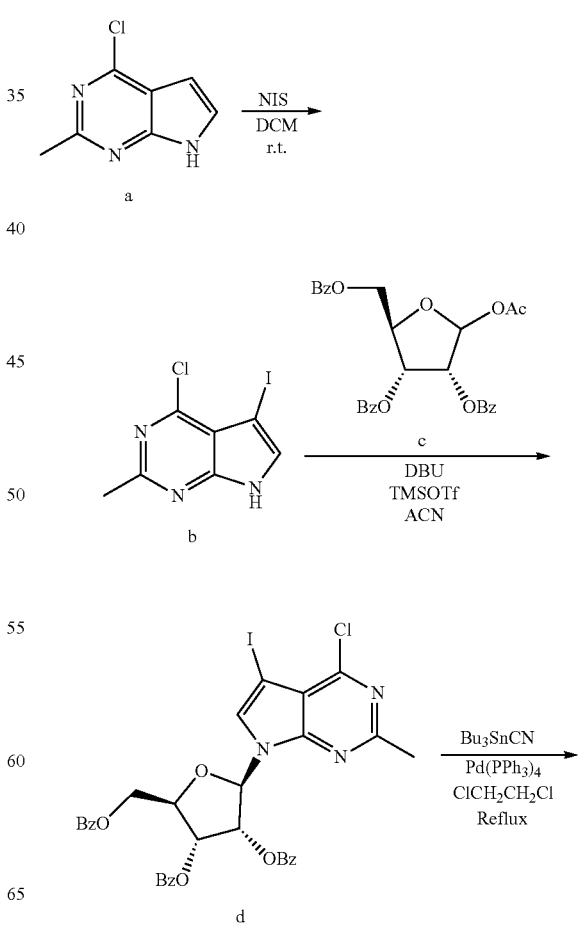

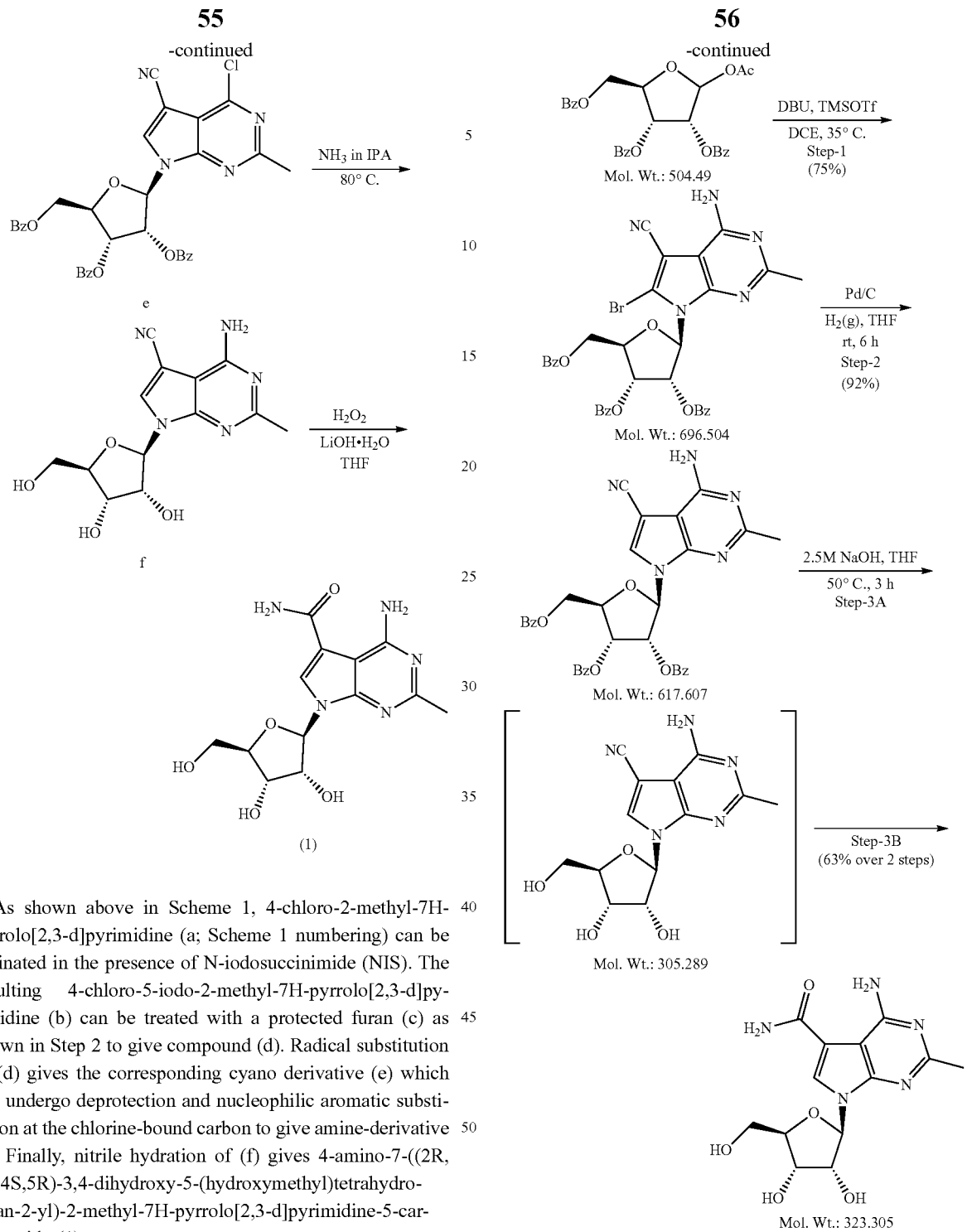

As shown above in Scheme 1, 4-chloro-2-methyl-7H-pyrrolo[2,3-d]pyrimidine (a; Scheme 1 numbering) can be iodinated in the presence of N-iodosuccinimide (NIS). The resulting 4-chloro-5-iodo-2-methyl-7H-pyrrolo[2,3-d]pyrimidine (b) can be treated with a protected furan (c) as shown in Step 2 to give compound (d). Radical substitution of (d) gives the corresponding cyano derivative (e) which can undergo deprotection and nucleophilic aromatic substitution at the chlorine-bound carbon to give amine-derivative (f). Finally, nitrile hydration of (f) gives 4-amino-7-((2R,3R,4S,5R)-3,4-dihydroxy-5-(hydroxymethyl)tetrahydrofuran-2-yl)-2-methyl-7H-pyrrolo[2,3-d]pyrimidine-5-carboxamide (1).

Scheme 2: General Synthesis of Compounds of the Invention

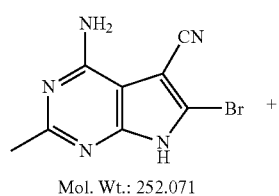

Mol. Wt.: 252.071

Step 1:
4-amino-6-bromo-2-methyl-7H-pyrrolo[2,3-d]pyrimidine-5-carbonitrile, (3R,4R,5R)-2-acetoxy-5-((benzoyloxy)methyl)tetrahydrofuran-3,4-diyl dibenzoate and DCE were charged in a reactor. Stirring was started and DBU was added. TMSOTf (8.01 kg) was added slowly. The reaction mixture was diluted with DCM and quenched slowly with water while being cooled. The reaction was extracted with DCM (19.90 kg), and washed with sat NaHCO₃. The aqueous phase was further extracted with DCM (19.71 kg) and washed with brine.

Step 2:

To a reactor were charged (2R,3R,4R,5R)-2-(4-amino-6-bromo-5-cyano-2-methyl-7H-pyrrolo[2,3-d]pyrimidin-7-yl)-5-((benzoyloxy)methyl)tetrahydrofuran-3,4-diyl dibenzoate, 10% Pd on C and THF. Hydrogen was submitted to the reactor and the mixture was stirred for about 4 hours at room temperature at about 31 psi.

The reaction mixture was filtered over Celite (7.2 kg) and a polish filter and the filter residue was washed with THF. The combined filtrate and wash was transferred to a 100-L jacketed reactor with the aid of a THF wash. The contents of the reactor were vacuum distilled with a maximum batch temperature of 30.0° C. over a period of about 6 hours to a final volume of 27 L. IPA was charged to the reactor. The contents of the reactor were vacuum distilled. IPA was charged to the reactor. The contents of the reactor were heated to about 60° C., agitated, and cooled slowly to about 5° C. Cold stirring was continued for a period of about 9 h with a minimum temperature of about 1° C. The slurry was filtered and washed with IPA. The residue was dried under vacuum with a nitrogen bleed to provide an LOD of 0.36%. Yield: (73.9%). $^1$H NMR confirms structure. Purity: 97.78% (HPLC, AUC).

Step 3:

A solution of (2R,3R,4R,5R)-2-(4-amino-5-cyano-2-methyl-7H-pyrrolo[2,3-d]pyrimidin-7-yl)-5-((benzoyloxy)methyl)tetrahydrofuran-3,4-diyl dibenzoate and THF was heated and the addition of NaOH was started. The initial addition gave a biphasic mixture and endothermic response but as the addition continued a single phased, clear solution formed which was accompanied by a fast exotherm; the reaction temperature was maintained during the rest of the addition and for an additional ~2½ h. IPC showed that no (2R,3R,4R,5R)-2-(4-amino-5-cyano-2-methyl-7H-pyrrolo[2,3-d]pyrimidin-7-yl)-5-((benzoyloxy)methyl)tetrahydrofuran-3,4-diyl dibenzoate was left.

The reaction mixture was cooled to 21° C. and neutralized with 3 N HCl with external cooling to neutral pH. The mixture continued to cool and the resulting neutralized mixture was distilled under vacuum until the emergence of solids were observed in the pot. The suspension was cooled and stirred for about 2 h at about 2° C. The beige suspension was filtered to afford a dark filtrate; the off-white residue was washed once with cold water.

In certain embodiments, the compounds of the disclosure, e.g., Formula I, Formula IA, Formula IB, or Formula II may be prepared as enantiomers, diastereomers, and racemates. In some embodiments, compounds of the disclosure, e.g., Formula I, Formula IA, Formula IB, or Formula II include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds disclosed herein are within the scope of the disclosure.

Compounds of the disclosure, e.g., Formula I, Formula IA, Formula IB, or Formula II can be synthesized substantially free of impurities. Compounds of the disclosure are more than or equal to about 99% w/w pure. In certain embodiments the phosphonate esters may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of phosphonate ester product. Furthermore, the methods allow the preparation of a phosphonate ester product having a purity of at least 98%, or at least 98.5% as measured by HPLC. In preferred embodiments, these products are obtained in a reaction sequence that does not involve purification by any form of chromatography (e.g., gas chromatography, HPLC, preparative LC, size exclusion chromatography, and the like).

Pharmaceutical Compositions and Methods of Treatment

As set forth above, provided herein are pharmaceutical compositions comprising compounds of the disclosure (e.g., Formula I, Formula IA, Formula IB, or Formula II) or pharmaceutically acceptable salts thereof. In some embodiments, the present disclosure provides pharmaceutical compositions comprising compounds of Formula I, Formula IA, Formula IB, or Formula II or pharmaceutically acceptable salts thereof and a pharmaceutically acceptable carrier and/or diluent. In some embodiments the present disclosure provides compounds of Formula I, Formula IA, Formula IB, or Formula II formulated as a pharmaceutical composition. In one embodiment, compounds of Formula I, Formula IA, Formula IB, or Formula II is formulated as a tablet. In another embodiment, compounds of Formula I, Formula IA, Formula IB, or Formula II is formulated as a suspension.

Techniques for formulation and administration of the disclosed compounds can be found in *Remington; the Science and Practice of Pharmacy*, $22^{nd}$ edition, Pharmaceutical Press (2012).

In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

The compounds of the disclosure, e.g., compounds of Formula I, Formula IA, Formula IB, or Formula II or pharmaceutically acceptable salts thereof described herein may be combined with a pharmaceutically acceptable carrier according to conventional pharmaceutical compounding techniques. Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

In another embodiment, the disclosure provides a method for the therapeutic and/or prophylactic treatment of viral infection in a subject, e.g., an immunodeficient subject, the method comprising administering any one of the compounds of Formula I, Formula IA, Formula IB, or Formula II or pharmaceutically acceptable salt thereof. In some embodiments, the salt has a purity of equal to or greater than 91% w/w, e.g., having less than or equal to 9% w/w of impurities, to the subject.

Pharmaceutical compositions comprising the compounds of the present disclosure (e.g., compounds of Formula I, Formula IA, Formula IB, or Formula II) may be formulated to have any concentration desired. In some embodiments, the composition is formulated such that it comprises at least a therapeutically effective amount.

Pharmaceutical compositions include those suitable for oral, sublingual, nasal, rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

When the compounds of the present disclosure are administered as pharmaceuticals to mammals, e.g., humans, they can be given per se or as a pharmaceutical composition containing, for example, about 0.1% to 99.9%, about 0.2 to 98%, about 0.3% to 97%, about 0.4% to 96%, or about 0.5 to 95% of active ingredient in combination with a pharmaceutically acceptable carrier. In one embodiment pharmaceutical composition containing about 0.5% to 90% of active ingredient in combination with a pharmaceutically acceptable carrier is suitable for administration to mammals, e.g., humans. Some embodiments of the present disclosure provide preparation of a pharmaceutical composition comprising about 0.1% to 99.9%, about 0.2 to 98%, about 0.3% to 97%, about 0.4% to 96%, or about 0.5 to 95% of the compounds of Formula I, Formula IA, Formula IB, or Formula II or pharmaceutically acceptable salts thereof, e.g., any one of the Compounds in Table 7 or pharmaceutically acceptable salt thereof, for use in treating, preventing, or prophylaxis of viral infections or viral infection associated disorders. The present disclosure provides use of about 0.1% to 99.9%, about 0.2 to 98%, about 0.3% to 97%, about 0.4% to 96%, or about 0.5 to 95% of the compounds of Formula I, Formula IA, Formula IB, or Formula II or pharmaceutically acceptable salts thereof for the manufacture of a medicament containing effective amounts of the compound for use in treating, preventing, or prophylaxis of viral infections and viral infection associated diseases.

The present disclosure provides for a compound of Formula I, Formula IA, Formula IB, or Formula II for use in treating a viral infection or a viral infection-associated disease or disorder. The compounds can be in a pharmaceutical formulation comprising about 0.1% to 99.9%, about 0.2 to 98%, about 0.3% to 97%, about 0.4% to 96%, or about 0.5 to 95% of the compounds of Formula I, Formula IA, Formula IB, or Formula II.

For any compound, the therapeutically effective amount of a compound or composition can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

The pharmaceutical compositions containing compounds of Formula I, Formula IA, Formula IB, or Formula II of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. The appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as, for example, peppermint, methyl salicylate, or orange flavoring.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. In some embodiments, the materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

The compounds of Formula I, Formula IA, Formula IB, or Formula II or pharmaceutically acceptable salts thereof are formulated as a pharmaceutical composition or are used in the manufacture of a medicament for the treatment of a viral infection and/or viral infection associated disease and/or disorder. Additionally, the present disclosure provides a compound of Formula I, Formula IA, Formula IB, or Formula II, or a composition comprising a compound of Formula I, Formula IA, Formula IB, or Formula II for use in treating a viral infection or a viral infection-associated disease or disorder. The composition and/or the medicament of the compounds of Formula I, Formula IA, Formula IB, or Formula II or pharmaceutically acceptable salts thereof can be formulated as a tablet or suspension. Tablets of the compounds of Formula I, Formula IA, Formula IB, or Formula II or pharmaceutically acceptable salts thereof are formulated comprising pharmacologically acceptable buffers, excipients, carriers, including emulsifiers, enhancers (e.g., absorption enhancers), disintegrants (e.g., Polyvinylpolypyrrolidone (polyvinyl polypyrrolidone, PVPP, crospovidone, crospolividone or E1202), which is a highly cross-linked modification of polyvinylpyrrolidone (PVP)), and/or polymers disclosed in the present disclosure and well-known in the art.

In one embodiment, the present disclosure provides tablet formulation of the compounds of Formula I, Formula IA, Formula IB, or Formula II or pharmaceutically acceptable salts thereof for use in treatment, prophylactic treatment or prevention viral infection and/or viral associated disease or disorder. The present disclosure provides tablet formulation of the compounds of Formula I, Formula IA, Formula IB, or Formula II or pharmaceutically acceptable salts thereof for use in treating subjects in need of such treatment including but not limited to immunodeficient subjects, or pre- or post-organ and/or tissue transplantation subjects. The present disclosure provides the compounds of Formula I, Formula IA, Formula IB, or Formula II or pharmaceutically acceptable salts thereof for the use in the manufacture of a medicament for use in treating subjects in need of such treatment including but not limited to immunodeficient subjects, or pre- or post-organ and/or tissue transplantation subjects.

In one embodiment, the present disclosure provides suspension formulations of the compounds of Formula I, Formula IA, Formula IB, or Formula II or pharmaceutically acceptable salts thereof for use in prophylactic treatment or prevention viral infection and/or viral associated disease and/or disorder. The present disclosure provides suspension formulation of the compounds of Formula I, Formula IA, Formula IB, or Formula II or pharmaceutically acceptable salts thereof for use in treating subjects in need of such treatment including but not limited to immunodeficient subjects, or pre- or post-organ and/or tissue transplantation subjects.

In another embodiment, additional excipients include but are not limited to sodium phosphate, dibasic, citric acid (monohydrate) (about 0.01-5% wt), sodium citrate (about 0.01-5% wt), xanthum gum (about 0.01-5% wt), methylparaben (sodium salt) (about 0.01-5% wt), propylparaben (sodium salt) (about 0.01-5% wt), sucralose (about 0.01-5% wt), microcrystalline cellulose and carboxymethylcellulose sodium (VivaPur MCG 591) (about 0.5-10% wt), high fructose corn syrup (about 10-70% wt), lemon lime flavor (WONF220J15) (about 0.01-5% wt), sodium hydroxide pellets, sodium hydroxide/hydrochloric acid, and purified water (about 68.93% wt).

The formulations of the present disclosure are used in manufacturing a medicament in prophylactic treatment and/or prevention viral infection and/or viral associated disease and/or disorder.

In another embodiment, the present disclosure provides compositions (e.g., pharmaceutical compositions) with desirable pharmacokinetic characteristics. For example, the compositions of the disclosure may provide a blood level of the compounds of Formula I, Formula IA, Formula IB, or Formula II or pharmaceutically acceptable salts thereof which, after metabolism to the therapeutically-active form (e.g., the diphosphate equivalent), results in blood levels of the metabolite that do not induce toxicity.

In some embodiments, the present disclosure provides a pharmaceutical composition comprising a compound described herein (e.g., compound 1, 2, 3, 4, 5, 6, 71, 77, 76, 107, 111, 126, 133, 137, 139, 141, 143, or 145, or a pharmaceutically acceptable salt, solvate, enantiomer, diastereomer, racemate or mixture thereof, or any combination thereof).

Disease Indications

In some embodiments, the present disclosure provides a method of treating a viral infection or a viral-infection-associated disease or disorder comprising administering to a subject in need thereof a compound of the disclosure (e.g., compound 1, 2, 3, 4, 5, 6, 71, 77, 76, 107, 111, 126, 133, 137, 139, 141, 143, or 145, or a pharmaceutically acceptable salt, solvate, enantiomer, diastereomer, racemate or mixture thereof, or any combination thereof).

In some embodiments, the present disclosure provides a use of a compound of the disclosure (e.g., compound 1, 2, 3, 4, 5, 6, 71, 77, 76, 107, 111, 126, 133, 137, 139, 141, 143, or 145, or a pharmaceutically acceptable salt, solvate, enantiomer, diastereomer, racemate or mixture thereof, or any combination thereof) in the manufacture of a medicament for treating a disease, (e.g., a viral infection or a viral-infection-associated disease or disorder).

In some embodiments, the present disclosure provides a use of a compound of the disclosure (e.g., compound 1, 2, 3, 4, 5, 6, 71, 77, 76, 107, 111, 126, 133, 137, 139, 141, 143, or 145, or a pharmaceutically acceptable salt, solvate, enantiomer, diastereomer, racemate or mixture thereof, or any combination thereof) for treating a disease, (e.g., a viral infection or a viral-infection-associated disease or disorder).

The present disclosure provides treatment and/or prevention of a viral infection with the compounds disclosed herein and pharmaceutically acceptable salts thereof. The compounds represented by Formula I, Formula IA, Formula IB, or Formula II are used in treating, preventing, and/or manufacturing a medicament for treating and/or preventing at least one virus selected from but not limited to ssRNA viruses. In some embodiments, the virus can be a norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71, papilloma virus, West Nile virus, yellow fever virus, foot-and-mouth disease virus, Rift Valley fever virus, and other flavivirus, arenavirus, bunyavirus, alphavirus, and human immunodeficiency virus (HIV) infections, and any combination thereof.

The present disclosure further provides a method of treatment, prevention, or delaying on-set of viral infections or viral-infection-associated diseases or disorders (e.g., norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71, papilloma virus, West Nile virus, yellow fever virus, foot-and-mouth disease virus, Rift Valley fever virus, & other flavivirus, arenavirus, bunyavirus, alphavirus, and human immunodeficiency virus (HIV) infections, and any combination thereof) by orally administering to a subject a pharmaceutical composition comprising a therapeutically effective dose of a compound of Formula I, Formula IA, Formula IB, or Formula II or a pharmaceutically acceptable salt thereof, in combination with one or more of compound or composition selected from an immunosuppressant and/or an antiviral agent.

In some embodiments, the present disclosure also provides a compound of Formula I, Formula IA, Formula IB, or Formula II in the manufacture of a medicament for the treatment, prevention, or delaying on-set of viral infections or viral-infection-associated diseases or disorders (e.g., norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71, papilloma virus, West Nile virus, yellow fever virus, foot-and-mouth disease virus, Rift Valley fever virus, & other flavivirus, arenavirus, bunyavirus, alphavirus, and human immunodeficiency virus (HIV) infections, and any combination thereof) by orally administering to a subject a pharmaceutical composition comprising a therapeutically effective dose of a compound of Formula I, Formula IA, Formula IB, or Formula II or a pharmaceutically acceptable salt thereof, in combination with one or more of compound or composition selected from an immunosuppressant and/or an antiviral agent.

In some embodiments, the present disclosure also provides a compound of Formula I, Formula IA, Formula IB, or Formula II for use in treatment, prevention, or delaying on-set of viral infections or viral-infection-associated diseases or disorders (e.g., norovirus, human cytomegalovirus (HCMV), BK virus (BKV), Epstein-Barr virus (EBV), adenovirus, JC virus (JCV), SV40, MC virus (MCV), KI virus (KIV), WU virus (WUV), vaccinia, herpes simplex virus 1 (HSV-1), herpes simplex virus 2 (HSV-2), human herpes virus 6 (HHV-6), human herpes virus 8 (HHV-8), hepatitis B virus, hepatitis C virus, varicella zoster virus (VZV), variola major, variola minor, smallpox, cowpox, camelpox, monkeypox, poliovirus, picornaviridae (e.g., rhinovirus), paramyxoviridae (e.g., respiratory syncytial virus, RSV), ebola virus, Marburg virus, Epstein-Barr virus (EBV), influenza, enterovirus (e.g., EV68 and EV71, papilloma virus, West Nile virus, yellow fever virus, foot-and-mouth disease virus, Rift Valley fever virus, & other flavivirus, arenavirus, bunyavirus, alphavirus, and human immunodeficiency virus (HIV) infections, and any combination thereof) by orally administering to a subject a pharmaceutical composition comprising a therapeutically effective dose of a compound of Formula I, Formula IA, Formula IB, or Formula II or a pharmaceutically acceptable salt thereof, in combination with one or more of compound or composition selected from an immunosuppressant and/or an antiviral agent.

In some embodiments, the present disclosure provides a method of treatment, prevention, or delaying on-set of Marburg virus infection or Marburg virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of Marburg virus infection or Marburg virus infection associated disease or disorder, by oral administration to a subject in need thereof.

In some embodiments, the present disclosure provides a compound of Formula I, Formula IA, Formula IB, or Formula II for use in treatment, prevention, or delaying on-set of Marburg virus infection or Marburg virus infection associated disease or disorder, by oral administration to a subject in need thereof.

In some embodiments the present disclosure provides a method of treatment, prevention, or delaying on-set of Ebola virus infection or Ebola virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of Ebola virus infection or Ebola virus infection associated disease or disorder, by oral administration to a subject in need thereof.

In some embodiments, the present disclosure provides a compound of Formula I, Formula IA, Formula IB, or Formula II for use in treatment, prevention, or delaying on-set of Ebola virus infection or Ebola virus infection associated disease or disorder, by oral administration to a subject in need thereof.

In some embodiments the present disclosure provides a method of treatment, prevention, or delaying on-set of influenza virus infection or influenza virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of influenza virus infection or influenza virus infection associated disease or disorder, by oral administration to a subject in need thereof.

In some embodiments, the present disclosure provides a compound of Formula I, Formula IA, Formula IB, or Formula II for use in treatment, prevention, or delaying on-set of influenza virus infection or influenza virus infection associated disease or disorder, by oral administration to a subject in need thereof.

In some embodiments the present disclosure provides a method of treatment, prevention, or delaying on-set of norovirus virus infection or norovirus virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of norovirus virus infection or norovirus virus infection associated disease or disorder, by oral administration to a subject in need thereof.

In some embodiments, the present disclosure provides a compound of Formula I, Formula IA, Formula IB, or Formula II for use in treatment, prevention, or delaying on-set of norovirus infection or norovirus infection associated disease or disorder, by oral administration to a subject in need thereof.

In some embodiments the present disclosure provides a method of treatment, prevention, or delaying on-set of piconaviridae virus infection or piconaviridae virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of piconaviridae virus infection or piconaviridae virus infection associated disease or disorder, by oral administration to a subject in need thereof.

In some embodiments, the present disclosure provides a compound of Formula I, Formula IA, Formula IB, or Formula II for use in treatment, prevention, or delaying on-set of picornaviridae virus infection or picornaviridae virus infection associated disease or disorder, by oral administration to a subject in need thereof.

In some embodiments the present disclosure provides a method of treatment, prevention, or delaying on-set of paramyxoviridae virus infection or paramyxoviridae virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of paramyxoviridae virus infection or paramyxoviridae virus infection associated disease or disorder, by oral administration to a subject in need thereof.

In some embodiments, the present disclosure provides a compound of Formula I, Formula IA, Formula IB, or Formula II for use in treatment, prevention, or delaying on-set of paramyxoviridae infection or paramyxoviridae infection associated disease or disorder, by oral administration to a subject in need thereof.

In some embodiments of the present disclosure provides a method of treatment, prevention, or delaying on-set of enterovirus infection or enterovirus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof.

In some embodiments, the present disclosure provides a compound of Formula I, Formula IA, Formula IB, or Formula II in the manufacture of a medicament for treatment, prevention, or delaying on-set of enterovirus infection or enterovirus infection associated disease or disorder, by oral administration to a subject in need thereof.

In any of the above embodiments, the compound can be compound 1.

In some embodiments, the present disclosure provides a compound of Formula I, Formula IA, Formula IB, or Formula II for use in treatment, prevention, or delaying on-set of enterovirus infection or enterovirus infection associated disease or disorder, by oral administration to a subject in need thereof.

The present disclosure further provides a method of prophylactic treatment, prevention, or delaying on-set of norovirus infection or a norovirus infection associated disease or disorder, by orally administering to a subject a pharmaceutical composition comprising a therapeutically effective dose of a compound of Formula I, Formula IA, Formula IB, or Formula II (e.g., compound 1) or a pharmaceutically acceptable salt thereof, in combination with one or more antiviral agent. In some embodiments, the method of prophylactic treatment comprises treating a subject with a compound of the disclosure prior to infection with the norovirus.

The present disclosure also provides a compound of Formula I, Formula IA, Formula IB, or Formula II (e.g., compound 1) in the manufacture of a medicament for the prophylactic treatment, prevention, or delaying on-set of norovirus infection or a norovirus infection associated disease or disorder, by orally administering to a subject a pharmaceutical composition comprising a therapeutically effective dose of a compound of Formula I, Formula IA, Formula IB, or Formula II or a pharmaceutically acceptable salt thereof, in combination with one or more antiviral agent.

The present disclosure also provides a compound of Formula I, Formula IA, Formula IB, or Formula II (e.g., compound 1) for use in the prophylactic treatment, prevention, or delaying on-set of norovirus infection or a norovirus infection associated disease or disorder, by orally administering to a subject a pharmaceutical composition comprising a therapeutically effective dose of a compound of Formula I, Formula IA, Formula IB, or Formula II or a pharmaceutically acceptable salt thereof, in combination with one or more antiviral agent. The present disclosure further provides a method of prophylactic treatment, prevention, or delaying on-set of enterovirus infection or an enterovirus infection associated disease or disorder, by orally administering to a subject a pharmaceutical composition comprising a therapeutically effective dose of a compound of Formula I, Formula IA, Formula IB, or Formula II or a pharmaceutically acceptable salt thereof, in combination with one or more antiviral agent.

The present disclosure also provides the use of a compound of Formula I, Formula IA, Formula IB, or Formula II in the manufacture of a medicament for prophylactic treatment, prevention, or delaying on-set of enterovirus infection or an enterovirus infection associated disease or disorder, by orally administering to a subject a pharmaceutical composition comprising a therapeutically effective dose of a compound of Formula I, Formula IA, Formula IB, or Formula II or a pharmaceutically acceptable salt thereof, in combination with one or more antiviral agent.

The present disclosure also provides a compound of Formula I, Formula IA, Formula IB, or Formula II for use in the prophylactic treatment, prevention, or delaying on-set of enterovirus infection or an enterovirus infection associated disease or disorder, by orally administering to a subject a pharmaceutical composition comprising a therapeutically effective dose of a compound of Formula I, Formula IA, Formula IB, or Formula II or a pharmaceutically acceptable salt thereof, in combination with one or more antiviral agent.

In one of the embodiments, compounds of Formula I, Formula IA, Formula IB, or Formula II are be used to treat norovirus. In another embodiments, compounds of Formula I, Formula IA, Formula IB, or Formula II are used to treat norovirus associated with specific genotypes such as those in genogroups I, II and IV, VI and VII which are known to infect humans (Phan et al., J. Med. Virol. 2007 September; 79(9): 1388-1400).

Dosage Regimens

The regimen of administration can affect what constitutes a pharmaceutically effective amount. The compounds of Formula I, Formula IA, Formula IB, or Formula II or pharmaceutically acceptable salts thereof can be administered to the subject either prior to or after the onset of a disease. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation. Further, the dosages may be co-administered in combination with other antiviral.

The dosage regimen utilizing the compounds can also be selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

In some embodiments, the subject treated for a viral infection (e.g., a norovirus infection or a norovirus infection associated disease or disorder) is administered once or twice a week with about 40 mg, 50 mg, 75 mg, 100 mg, 150 mg, 175 mg, 200 mg, or 250 mg of a compound of Formula I, Formula IA, Formula IB, or Formula II or a pharmaceutically acceptable salt thereof. The present disclosure provides treatment of a subject for norovirus infection or norovirus infection associated disease or disorder by administering to the subject once a week (QW) about 200 mg or twice a week (BIW) about 100 mg of a compound of Formula I, Formula IA, Formula IB, or Formula II, or a pharmaceutically acceptable salt thereof. In one embodiment, the subject is treated twice a week (BIW) with about 100 mg of the compound. In another embodiment, the subject is treated once a week (QW) with about 200 mg, or twice a week (BIW) with about 100 mg of the compound.

In an embodiment, a compound of Formula I, Formula IA, Formula IB, or Formula II or pharmaceutically acceptable salt thereof having a purity of equal to or greater than about 91% is administered orally to a subject, for example, at a dosage of about 0.01 mg/kg to about 10 mg/kg or more, e.g., up to 100 mg/kg, or up to 400 mg/kg, or up to 1000 mg/kg.

In another embodiment, a compound of Formula I, Formula IA, Formula IB, or Formula II or pharmaceutically acceptable salt thereof having a purity of equal to or greater than about 91% w/w is administered to a subject at a dosage of about 0.01 mg/kg, 0.05 mg/kg, 0.1 mg/kg, 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, or 10 mg/kg or more or any range therein.

In a preferred aspect, the disease or condition to be treated is viral infection.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, once every two weeks, or monthly depending on half-life and clearance rate of the particular formulation.

In some embodiments, the administration continues for ten total doses. For instance, the compounds of Formula I, Formula IA, Formula IB, or Formula II can be administered at dosages of about 100 mg twice a week for five weeks (i.e., ten total doses). Alternatively, the compounds of Formula I, Formula IA, Formula IB, or Formula II may be administered with a loading dose of about 200 mg followed by about 100 mg doses continuing twice a week. In some embodiments, the administration continues for ten total doses. For instance, the compounds of Formula I, Formula IA, Formula IB, or Formula II may be administered at a loading dose of about 200 mg followed by nine additional about 100 mg doses twice a week for a total of ten doses. In one of the embodiments Compounds of Formula I, Formula IA, Formula IB, or Formula II can be dosed daily in the range of about 20-200 mg/day or weekly in the range of about 200 mg-3000 mg.

In one or more embodiments the compounds of the disclosure are useful at treating a viral infection such as a norovirus infection or a norovirus-infection associated disease or disorder. In some embodiments, treatment of the infection, e.g., norovirus infection, can comprise daily dosing, or dosing multiple times per day. In some embodiments, the total treatment regimen only lasts as long as the norovirus infection is active (e.g., between 1-3 days). In some embodiments, the compounds of the disclosure can be dosed multiple times per day for 1-3 days to treat a norovirus infection.

In another embodiment, tablets or suspensions of the compounds of Formula I, Formula IA, Formula IB, or Formula II or pharmaceutically acceptable salts thereof are administered at a dose of about 40-3000 mg daily, BID, TID, once a week (QW) or twice a week (BIW). In another embodiment, tablets or suspensions of the compounds of Formula I, Formula IA, Formula IB, or Formula II or pharmaceutically acceptable salts thereof are administered at a dose of about 40-400 mg daily, BID, TID, once a week (QW) or twice a week (BIW).

In therapeutic applications, the dosages of the pharmaceutical compositions disclosed herein vary depending on the agent, the age, weight, and clinical condition of the recipient patient, and the experience and judgment of the clinician or practitioner administering the therapy, among other factors affecting the selected dosage. Dosages can range from about 0.01 mg/kg to about 100 mg/kg. In preferred aspects, dosages can range from about 0.1 mg/kg to about 10 mg/kg. In an aspect, the dose will be in the range of about 1 mg to about 1 g; about 10 mg to about 500 mg; about 20 mg to about 400 mg; about 40 mg to about 400 mg; or about 50 mg to about 400 mg, in single, divided, or continuous doses (which dose may be adjusted for the patient's weight in kg, body surface area in $m^2$, and age in years). In certain embodiments, the amount per dosage form can be about 0.1 mg to about 3000 mg, e.g., about 0.1 mg, about 0.5 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg, about 600 mg, about 700 mg, about 800 mg, about 900 mg, about 1000 mg, about 1250 mg, 1500 mg, about 1750 mg, about 2000 mg, about 2500 mg, or about 3000 mg. In one embodiment, the amount can be about 20 mg. In one embodiment, the amount can be about 50 mg. In another embodiment the dosage can be 100 mg. In another embodiment the dose can be 500 mg.

In another embodiment, the compounds of Formula I, Formula IA, Formula IB, or Formula II or pharmaceutically acceptable salts thereof are administered to a subject as a single dose. In another embodiment, the compounds of Formula I, Formula IA, Formula IB, or Formula II or pharmaceutically acceptable salts thereof are administered to a subject in multiple doses. Multiple doses can be administered regularly, for example, once every 12 hours, once a day, every 2 days, every 3 days, every 4 days, every 5 days, every 6 days, every 7 days, every 8 days, every 9 days, every 10 days, every 11 days, every 12 days, every 13 days, every 14 days or every 15 days. For example, doses can be administered twice per week. Moreover, each individual dose can be administered with the same or a different dosage.

For example, a subject can be administered any one the compounds of Formula I, Formula IA, Formula IB, or Formula II or pharmaceutically acceptable salts thereof with a first dose of about 1-20 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, about 3.9-4.0 mg/kg, about 4.0-5.0 mg/kg, about 5.0-6.0 mg/kg, about 6.0-7.0 mg/kg, about 7.0-8.0 mg/kg, about 8.0-9.0 mg/kg, about 9.0-10.0 mg/kg, or about 10-20 mg/kg) of any one of the Compounds of Formula I, Formula IA, Formula IB, or Formula II (or a pharmaceutically acceptable salt thereof) followed by one or more additional doses at 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of any one of the Compounds of Formula I, Formula IA, Formula IB, or Formula II (or a pharmaceutically acceptable salt thereof) in the same week or in the following week. For example, a subject can be administered with a first dose of about 3 mg/kg followed by one or more additional doses at about 1 mg/kg. For example, a subject can be administered with a first dose of about 2 mg/kg followed by one or more additional doses at about 3 mg/kg. For example, a subject can be administered with a first dose of 4 mg/kg followed by one or more additional doses at about 4 mg/kg.

Multiple doses can also be administered at variable time intervals. For example, the first 2, 3, 4, 5, 6, 7, or 8 or more doses can be administered at an interval of 6 days followed by additional doses administered at an interval of 7 days. For example, the first 2, 3, 4, 5, 6, 7, or 8 or more doses can be administered at an interval of 7 days followed by additional doses administered at an interval of 3 days.

In one embodiment, the compounds of Formula I, Formula IA, Formula IB, or Formula II or pharmaceutically acceptable salts thereof are administered to a subject once a week at a dose of about 40-3000 mg, or twice a week at a dose of about 40-3000 mg.

In some embodiments, the pharmaceutical composition of the present disclosure is administered daily, BID, TID, once a week (QW), or twice a week (BIW) with about 40-3000 mg of compounds of Formula I, Formula IA, Formula IB, or Formula II or pharmaceutically acceptable salts thereof. The pharmaceutical compositions of the present disclosure is administered daily, BID, TID, once a week (QW), or twice a week (BIW) with about 40 mg, 50 mg, 75 mg, 100 mg, 150 mg, 175 mg, 200 mg, 250 mg, 275 mg, 300 mg, 325 mg, 350 mg, 375 mg, 400 mg, 450 mg, 500 mg, 500-600 mg, 600-700 mg, 700-800 mg, 800-900 mg, or 900-1000 mg, or twice a week (BIW) with about 40 mg, 50 mg, 75 mg, 100 mg, 150 mg, 175 mg, 200 mg, 250 mg, 275 mg, 300 mg, 325 mg, 350 mg, 375 mg, or 400 mg, 450 mg, 500 mg, 500-600 mg, 600-700 mg, 700-800 mg, 800-900 mg, or 900-1000 mg of Compounds of Formula I, Formula IA, Formula IB, or Formula II or pharmaceutically acceptable salts thereof.

The present disclosure provides compounds of Formula I, Formula IA, Formula IB, or Formula II administered at a dose of about 1-100 mg/kg (e.g., 10-20 mg/kg, 20-50 mg/kg, 50-75 mg/kg, 75-100 mg/kg).

Routes of Administration

The compounds of the present disclosure, or pharmaceutically acceptable salts, esters or derivatives thereof, can be administered orally, nasally, intranasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

A pharmaceutical composition of the disclosure is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Combination Therapy

The present disclosure provides methods of preventing or treating a viral infection in a subject (e.g., a norovirus infection). The methods comprise administering a subject a therapeutically effective amount of a compound described herein. The compounds may be used in a monotherapy or combination therapy regime.

As used herein, "monotherapy" means or refers to the administration of a single active or therapeutic compound (e.g., a compound of Formula I, Formula IA, Formula IB, or Formula II) to a subject in need thereof. Preferably, monotherapy will involve administration of a therapeutically effective amount of an active compound. For example, norovirus monotherapy with one of the compound of the present disclosure, or a pharmaceutically acceptable salt, prodrug, metabolite, analog or derivative thereof, to a subject in need of treatment of norovirus. Monotherapy may be contrasted with combination therapy, in which a combination of multiple active compounds is administered, preferably with each component of the combination present in a therapeutically effective amount. In one aspect, monotherapy with a compound of the present disclosure, or a pharmaceutically acceptable salt, prodrug, metabolite, polymorph or solvate thereof, is more effective than combination therapy in inducing a desired biological effect.

As used herein, "combination therapy" or "co-therapy" includes the administration of a compound of the present disclosure, or a pharmaceutically acceptable salt, prodrug, metabolite, polymorph or solvate thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present disclosure.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

In some embodiments the present disclosure provides a method of treatment, prevention, or delaying on-set of a viral infection, (e.g., norovirus virus infection or norovirus virus infection associated disease or disorder; influenza virus infection or influenza virus infection associated disease or disorder), by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II in the manufacture of a medicament for treatment, prevention, or delaying on-set of a viral infection, (e.g., norovirus virus infection or norovirus virus infection associated disease or disorder; influenza virus infection or influenza virus infection associated disease or disorder), by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II for use in treatment, prevention, or delaying on-set of a viral infection, (e.g., norovirus virus infection or norovirus virus infection associated disease or disorder; influenza virus infection or influenza virus infection associated disease or disorder), by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

In some embodiments the present disclosure provides a method of treatment, prevention, or delaying on-set of piconaviridae virus infection or piconaviridae virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II in the manufacture of a medicament for treatment, prevention, or delaying on-set of a piconaviridae virus infection or piconaviridae virus infection associated disease or disorder by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II for use in treatment, prevention, or delaying on-set of a piconaviridae virus infection or picornaviridae virus infection associated disease or disorder by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

In some embodiments the present disclosure provides a method of treatment, prevention, or delaying on-set of paramyxoviridae virus infection or paramyxoviridae virus infection associated disease or disorder, by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II in the manufacture of a medicament for treatment, prevention, or delaying on-set of a paramyxoviridae virus infection or paramyxoviridae virus infection associated disease or disorder by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

The present disclosure also provides a compound of Formula I, Formula IA, Formula IB, or Formula II for use in treatment, prevention, or delaying on-set of a paramyxoviridae virus infection or paramyxoviridae virus infection associated disease or disorder by oral administration to a subject in need thereof a pharmaceutical composition of a therapeutically effective dose of a compound of Formula I, Formula IA, Formula IB, or Formula II or a pharmaceutically acceptable salt thereof in combination with one or more antiviral agent.

In one embodiment, the method of treating a viral infection, e.g., influenza virus infection or norovirus infection further comprises administering at least one additional antiviral agent. In one embodiment, the compound of Formula I, Formula II, or Formula IA can be for use in combination with an additional antiviral agent. In one or more embodiments, the compound of Formula I, Formula IA, Formula IB, or Formula II for use in the manufacture of a medicament in combination with an additional antiviral agent. In one embodiment, the one additional antiviral agent is an adamantane. In a further embodiment, the one additional antiviral agent is amantadine or rimantadine. In another embodiment, the one additional antiviral agent is a neuraminidase inhibitor (e.g., oseltamivir, zanamivir, laninamivir, and peramivir). In a further embodiment, the one additional antiviral agent is oseltamivir or zanamivir.

In some embodiments, the pharmaceutical composition of the present disclosure (e.g., a compound of Formula I, Formula IA, Formula IB, or Formula II) is administered in combination with one or more compounds or compositions selected from midazolam, cyclosporine A, tacrolimus, ganciclovir, valganciclovir, foscavir, cidofovir, second-line anti-CMV drugs, second-line anti-HCV drugs, foscarnet, filgrastim, pegfilgrastim, corticosteroids such as budesonide, beclomethasone, and broad-spectrum CYP inhibitor aminobenzotriazole or combinations thereof.

In additional embodiments, the compound is for administration in combination with at least one other immunosuppressant agent. In one embodiment, the immunosuppressant agent is concurrently or sequentially administered. The immunosuppressant agents include but are not limited to Daclizumab, Basiliximab, Tacrolimus, Sirolimus, Mycophenolate, Cyclosporine A, Glucocorticoids, Anti-CD3 monoclonal antibodies, Antithymocyte globulin, Anti-CD52 monoclonal antibodies, Azathioprine, Everolimus, Dactinomycin, Cyclophosphamide, Platinum, Nitrosurea, Methotrexate, Mercaptopurine, Muromonab, IFN gamma, Infliximab, Etanercept, Adalimumab, Natalizumab, Fingolimod, and combinations thereof.

The compounds or compositions provided herein may also be used in combination with an enhancer agent, with other active ingredients, or with an immunosuppressant agent. In certain embodiments, the compounds may be administered in combination, or sequentially, with another therapeutic agent or an enhancer. Such other therapeutic agents include those known for treatment, prevention, or amelioration of one or more symptoms associated with viral infections. It should be understood that any suitable combination of the compounds provided herein with one or more of the above-mentioned compounds and optionally one or more further pharmacologically active substances are considered to be within the scope of the present disclosure. In another embodiment, the compound provided herein is administered prior to or subsequent to the one or more additional active ingredients. In one embodiment, two or more of the antiviral agents disclosed herein are administered serially or in combination. The amount of some enhancers can be selected using methods known in the art to enhance the bioavailability of the anti-viral agent. Any amount can be used that provides a desired response by some enhancers. The dosages may range, in a non-limiting example, from 0.001 mg to about 3000 mg of compound per kilogram of body weight per day, e.g., 0.01 to 500 mg/kg, or e.g., 0.1-20 mg/kg.

The pharmacokinetic behavior of a composition will vary somewhat from subject to subject within a population. The numbers described above for the compositions disclosed herein are based on the average behavior in a population. The present disclosure is intended to encompass compositions that on average fall within the disclosed ranges, even though it is understood that certain subjects may fall outside of the ranges.

The pharmaceutical compositions can be included in a container, pack, or dispenser together with instructions for administration. The present disclosure provides a kit including, in addition to a pharmaceutical composition of any one of the disclosed compounds, a container, pack, or dispenser together with instructions for administration.

A compound of the present disclosure, or a pharmaceutically acceptable salt, prodrug, metabolite, analog or derivative thereof, may be administered in combination with a second antiviral compound. For example, as noted above, the compositions of the present disclosure may include the compounds as described above in combination with one or more (e.g., 1, 2, 3) additional active agents such as described in this section in analogous manner as known in the art. Additional antiviral active agents that may be used with the compounds of the present disclosure in carrying out the present methods include, but are not limited to, those that target the M2 ion channel in influenza A viruses (e.g., the adamantanes, such as amantadine and rimantadine); those that inhibit viral uncoating following entry into the cell, agents that block release of the newly formed virions from the surface of infected cells (e.g., the neuraminidase inhibitors, such as oseltamivir and zanamivir).

Methods for Preventing Disease or Disorder Due to Virus Reactivation.

The current disclosure also provides a method of preventing a disease or disorder in a subject at risk of virus infection reactivation, by orally administering to the subject a pharmaceutical composition of a therapeutically effective dose of a compound of Formula I, Formula IA, Formula IB, or Formula II or a pharmaceutically acceptable salt thereof. In some embodiments, the virus at risk of reactivation can be influenza, norovirus, EBV, ebola, picornaviridae, paramyxoviridae, and Marburg virus. In some preferred embodiments, the virus at risk of reactivation can be influenza.

Effect of Food

In some embodiments, the pharmaceutical composition of the current embodiments, e.g., tablet or suspension, may be provided to a subject when the subject is either fasted or in fed conditions. In one embodiment, the composition comprising a compound of Formula I, Formula IA, Formula IB, or Formula II (or a pharmaceutically acceptable salt thereof) may be provided to a subject having an empty stomach, e.g., after fasting for less than 24 hours but more than 12 hours, more than 11 hours, more than 10 hours, more than 8 hours, or more than 5 hours.

In other embodiments, the composition comprising a compound of Formula I, Formula IA, Formula IB, or Formula II (or a pharmaceutically acceptable salt thereof) may be provided to a subject in combination with food or subsequent to having food. In one embodiment, a compound of Formula I, Formula IA, Formula IB, or Formula II (or a pharmaceutically acceptable salt thereof) may be taken by a subject on an empty stomach.

Patient Population

In certain embodiments, compounds of Formula I, Formula IA, Formula IB, or Formula II (or a pharmaceutically acceptable salt thereof), a composition comprising a compound of Formula I, Formula IA, Formula IB, or Formula II, or a combination therapy comprising a composition of Formula I, Formula IA, Formula IB, or Formula II is administered to a mammal in need thereof (e.g., a human) which is about 1 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old, or 95 to 100 years old. In some embodiments, the mammal is suffering from a viral infection (e.g., an ssRNA infection such as a norovirus infection).

In certain embodiments, a compound of Formula I, Formula IA, Formula IB, or Formula II, a composition comprising a compound of Formula I, Formula IA, Formula IB, or Formula II, or a combination therapy comprising a compound of Formula I, Formula IA, Formula IB, or Formula II is administered to a human at risk for developing a virus infection. In certain embodiments, a compound of Formula I, Formula IA, Formula IB, or Formula II, a composition comprising a compound of Formula I, Formula IA, Formula IB, or Formula II, or a combination therapy comprising a compound of Formula I, Formula IA, Formula IB, or Formula II is administered to a human with a virus infection. In certain embodiments, the patient is a human about 1 to 6 months old, 6 to 12 months old, 1 to 5 years old, 5 to 10 years old, 5 to 12 years old, 10 to 15 years old, 15 to 20 years old, 13 to 19 years old, 20 to 25 years old, 25 to 30 years old, 20 to 65 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old.

In some embodiments, a compound of Formula I, Formula IA, Formula IB, or Formula II, a composition comprising a compound of Formula I, Formula IA, Formula IB, or Formula II, or a combination therapy comprising a compound of Formula I, Formula IA, Formula IB, or Formula II is administered to a human infant. In other embodiments, a compound of Formula I, Formula IA, Formula IB, or Formula II, or a combination therapy comprising a compound of Formula I, Formula IA, Formula IB, or Formula II is administered to a human child. In other embodiments, a compound of Formula I, Formula IA, Formula IB, or Formula II, a composition comprising a compound of Formula I, Formula IA, Formula IB, or Formula II, or a combination therapy comprising a compound of Formula I, Formula IA, Formula IB, or Formula II is administered to a human adult. In yet other embodiments, a compound of Formula I, Formula IA, Formula IB, or Formula II, a composition comprising a compound of Formula I, Formula IA, Formula IB, or Formula II, or a combination therapy comprising a compound of Formula I, Formula IA, Formula IB, or Formula II is administered to an elderly human.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

In some embodiments, the compound of Formula II is:

| Compound No. | STRUCTURE |
|---|---|
| 1 | 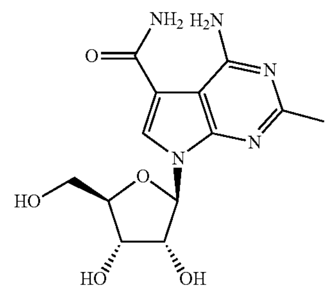 [SMILES: Cc1nc(N)c2c(C(N)=O)cn([C@@H]3O[C@H](CO)[C@@H](O)[C@H]3O)c2n1] |
| 2 | 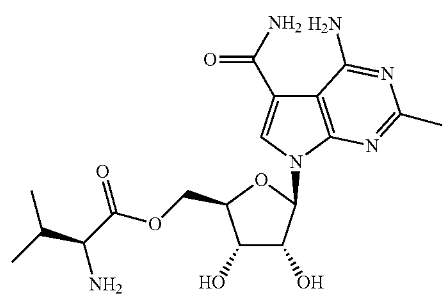 [SMILES: Cc1nc(N)c2c(C(N)=O)cn([C@@H]3O[C@H](COC(=O)[C@@H](N)C(C)C)[C@@H](O)[C@H]3O)c2n1] |
| 3 | 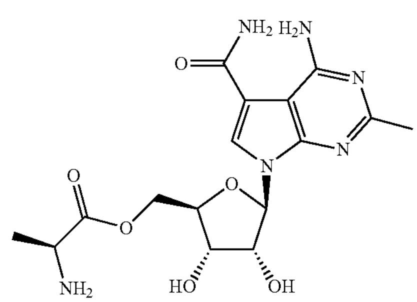 [SMILES: Cc1nc(N)c2c(C(N)=O)cn([C@@H]3O[C@H](COC(=O)[C@H](C)N)[C@@H](O)[C@H]3O)c2n1] |

-continued
| Compound No. | STRUCTURE |
|---|---|
| 4 | 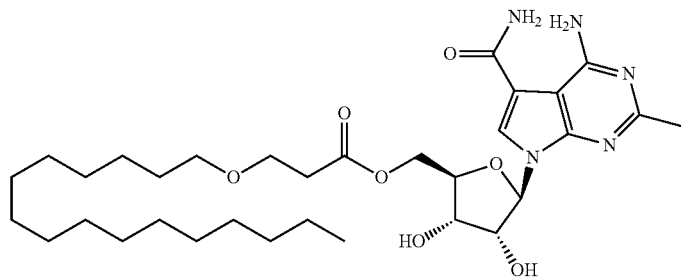 [SMILES: CCCCCCCCCCCCCCCCOCCC(=O)OC[C@H]1O[C@@H](n2cc(C(N)=O)c3c(N)nc(C)nc32)[C@H](O)[C@@H]1O] |
| 5 | 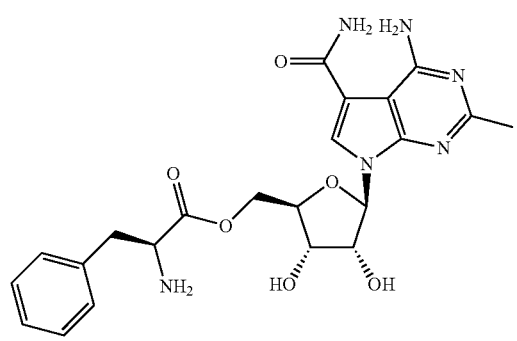 [SMILES: Cc1nc(N)c2c(C(N)=O)cn([C@@H]3O[C@H](COC(=O)[C@@H](N)Cc4ccccc4)[C@@H](O)[C@H]3O)c2n1] |
| 6 | 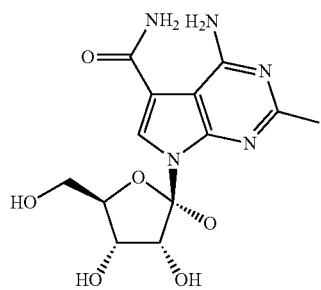 [SMILES: Cc1nc(N)c2c(C(N)=O)cn([C@]3(O)O[C@H](CO)[C@@H](O)[C@H]3O)c2n1] |
| 71 | 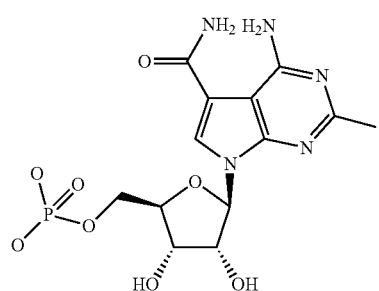 [SMILES: Cc1nc(N)c2c(C(N)=O)cn([C@@H]3O[C@H](COP(=O)(O)O)[C@@H](O)[C@H]3O)c2n1] |
| 77 | 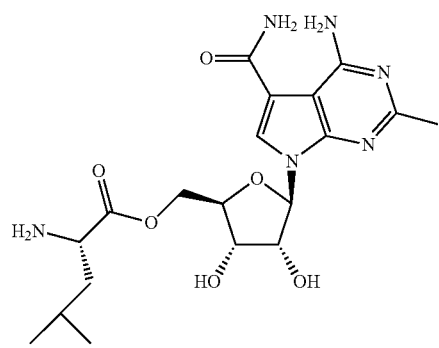 [SMILES: Cc1nc(N)c2c(C(N)=O)cn([C@@H]3O[C@H](COC(=O)[C@@H](N)CC(C)C)[C@@H](O)[C@H]3O)c2n1] |

-continued
| Compound No. | STRUCTURE |
|---|---|
| 76 | 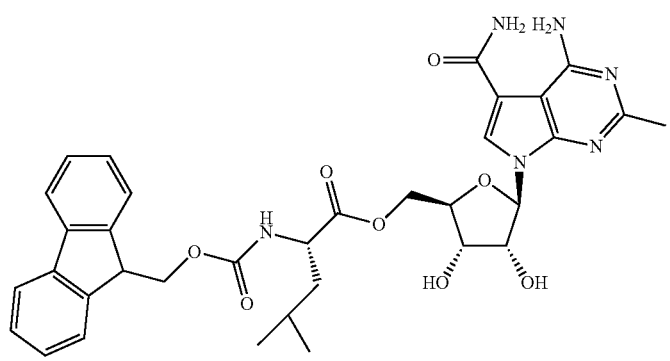 [SMILES: Cc1nc(N)c2c(C(N)=O)cn([C@@H]3O[C@H](COC(=O)[C@H](CC(C)C)NC(=O)OCC4c5ccccc5-c5ccccc54)[C@@H](O)[C@H]3O)c2n1] |
| 107 | 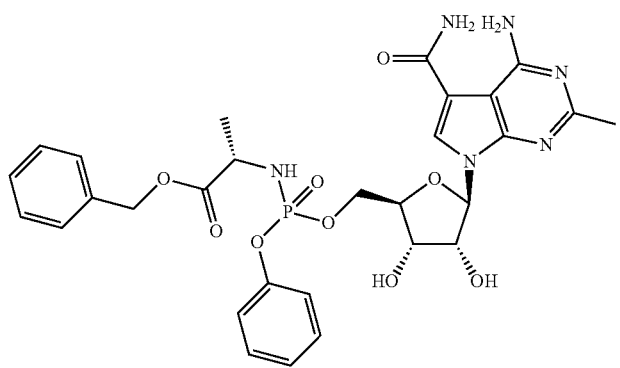 [SMILES: Cc1nc(N)c2c(C(N)=O)cn([C@@H]3O[C@H](COP(=O)(N[C@@H](C)C(=O)OCc4ccccc4)Oc4ccccc4)[C@@H](O)[C@H]3O)c2n1] |
| 111 | 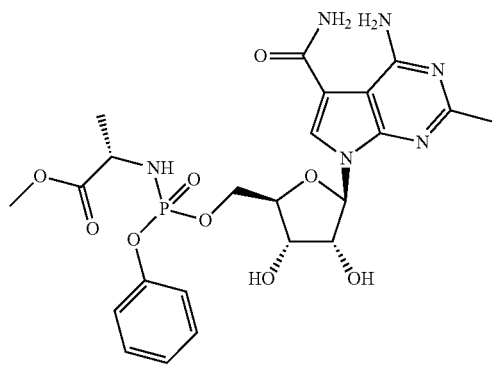 |
| 126 | 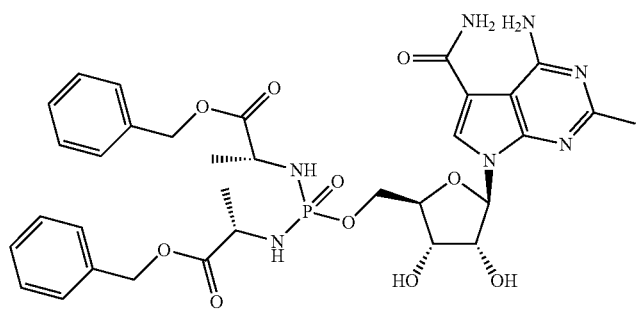 [SMILES: Cc1nc(N)c2c(C(N)=O)cn([C@@H]3O[C@H](COP(=O)(N[C@@H](C)C(=O)OCc4ccccc4)N[C@H](C)C(=O)OCc4ccccc4)[C@@H](O)[C@H]3O)c2n1] |

| Compound No. | STRUCTURE |
|---|---|
| 133 | 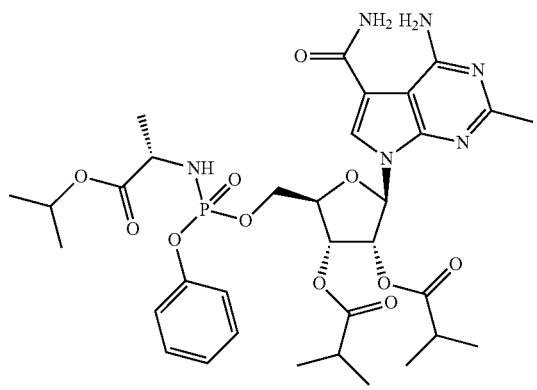 [SMILES: Cc1nc(N)c2c(C(N)=O)cn([C@@H]3O[C@H](COP(=O)(N[C@@H](C)C(=O)OC(C)C)Oc4ccccc4)[C@@H](OC(=O)C(C)C)[C@H]3OC(=O)C(C)C)c2n1] |
| 137 | 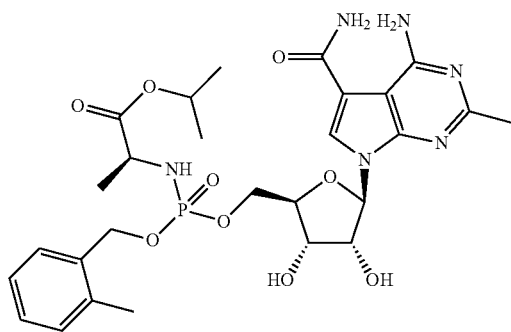 [SMILES: Cc1nc(N)c2c(C(N)=O)cn([C@@H]3O[C@H](COP(=O)(N[C@@H](C)C(=O)OC(C)C)OCc4ccccc4C)[C@@H](O)[C@H]3O)c2n1] |
| 139 | 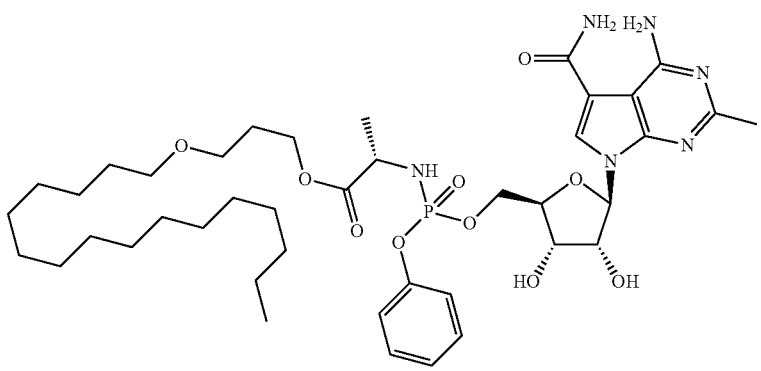 [SMILES: CCCCCCCCCCCCCCCCOCCCOC(=O)[C@H](C)NP(=O)(OC[C@H]1O[C@@H](n2cc(C(N)=O)c3c(N)nc(C)nc32)[C@H](O)[C@@H]1O)Oc1ccccc1] |
| 141 | 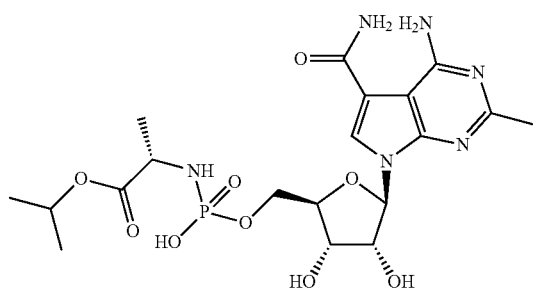 [SMILES: Cc1nc(N)c2c(C(N)=O)cn([C@@H]3O[C@H](COP(=O)(O)N[C@@H](C)C(=O)OC(C)C)[C@@H](O)[C@H]3O)c2n1] |

| Compound No. | STRUCTURE |
|---|---|
| 143 | 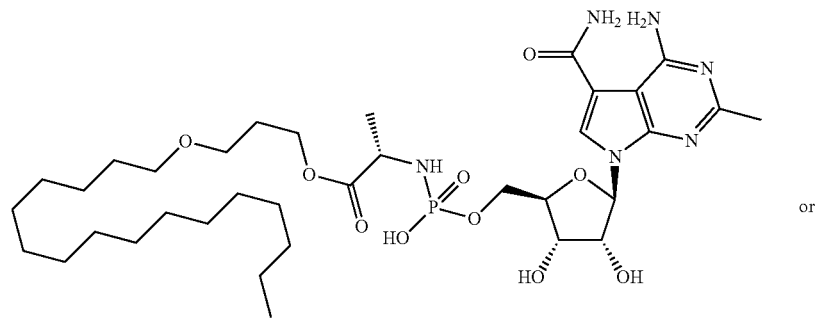 [SMILES: CCCCCCCCCCCCCCCCOCCCOC(=O)[C@H](C)NP(=O)(O)OC[C@H]1O[C@@H](n2cc(C(N)=O)c3c(N)nc(C)nc32)[C@H](O)[C@@H]1O] or |
| 145 | 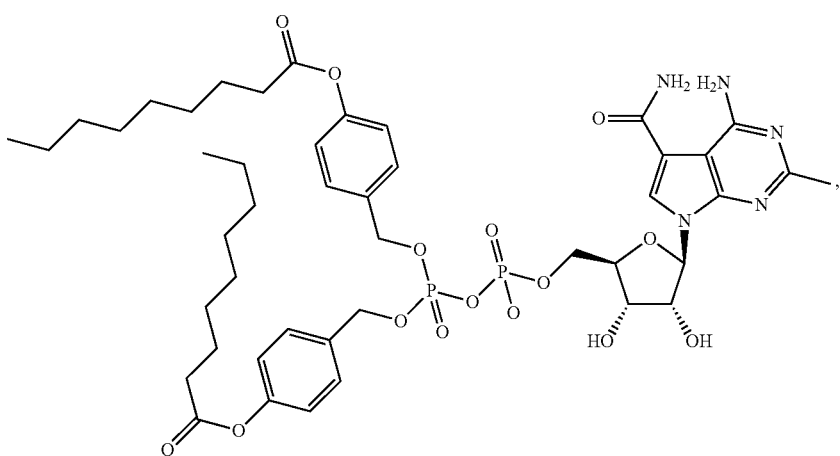 [SMILES: CCCCCCCCC(=O)Oc1ccc(COP(=O)(OCc2ccc(OC(=O)CCCCCCCC)cc2)OP(=O)(O)OC[C@H]2O[C@@H](n3cc(C(N)=O)c4c(N)nc(C)nc43)[C@H](O)[C@@H]2O)cc1] , |
or a pharmaceutically acceptable salt, solvate, enantiomer, diastereomer, racemate or mixture thereof.
In some embodiments, compounds of Formula I, II, IA, IB or analogs thereof are:
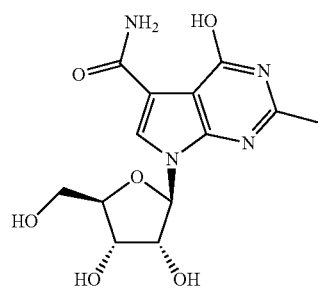
7
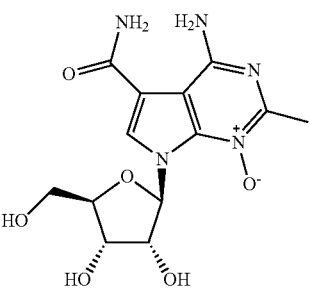
8
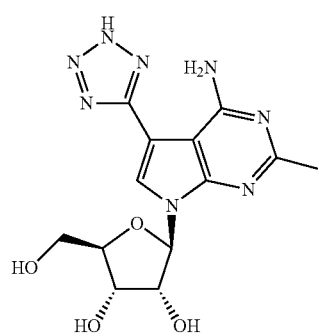
10
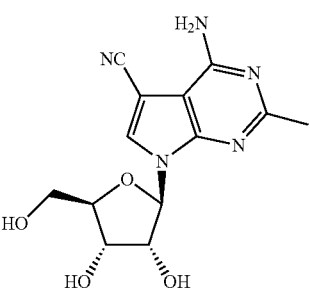
11

-continued
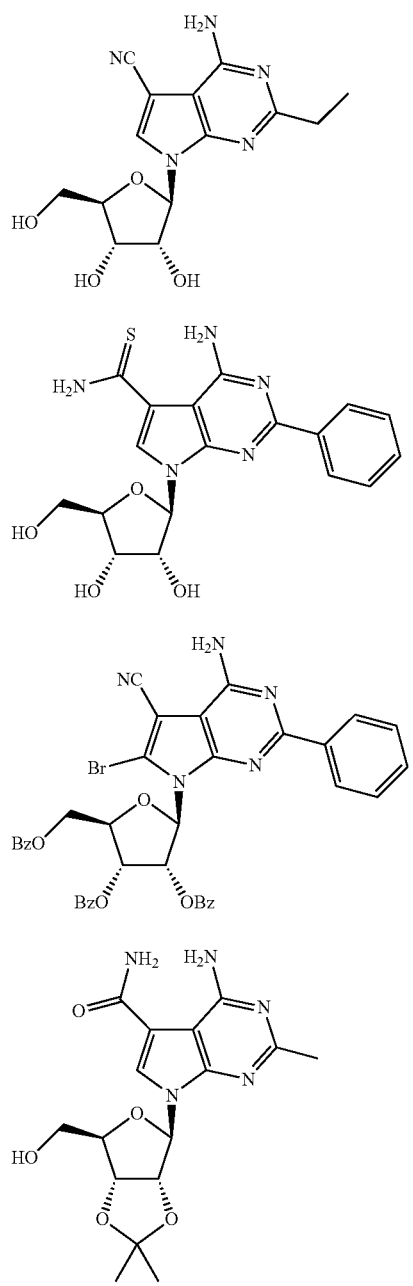
12
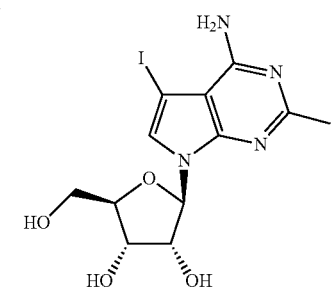
14
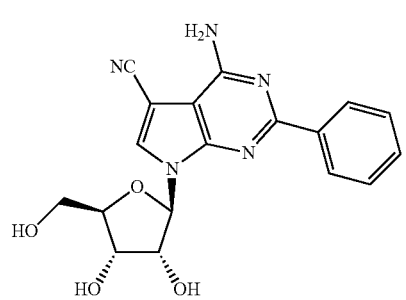
16
17
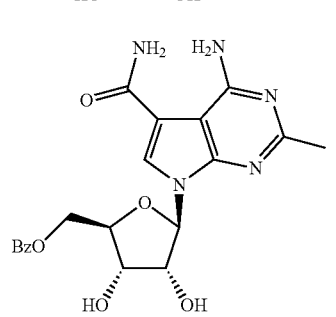
18
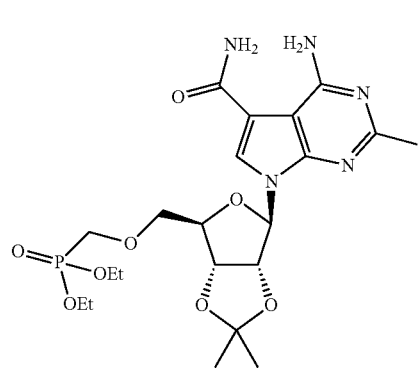
19
20
21
22
27
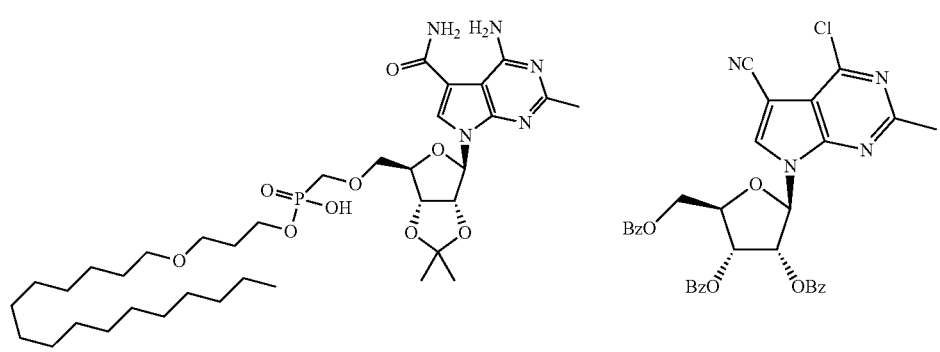

-continued
28
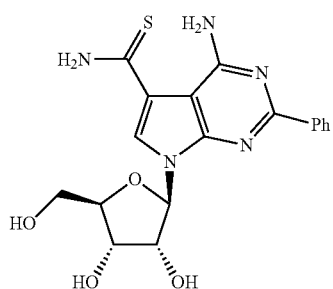
29
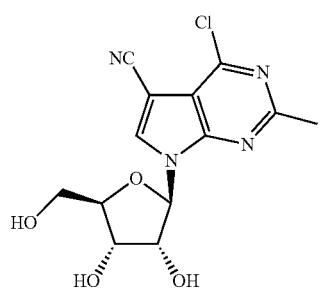
30
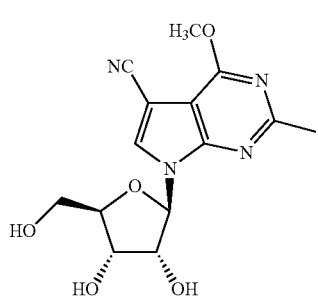
31
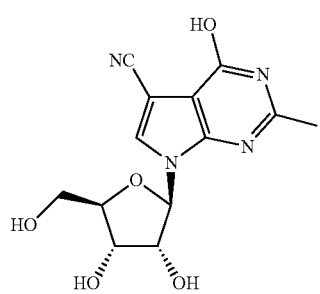
32
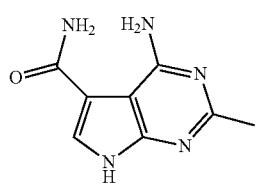
33
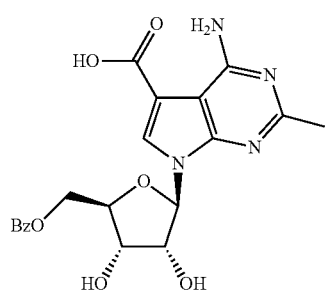
34
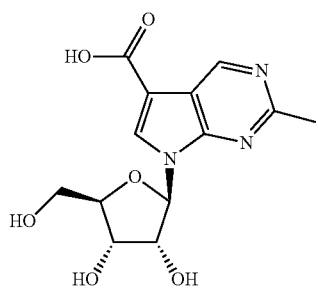
35
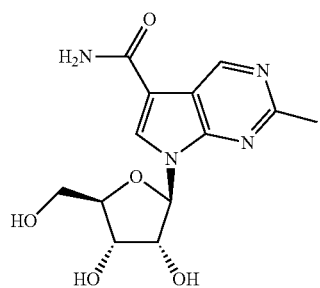
36
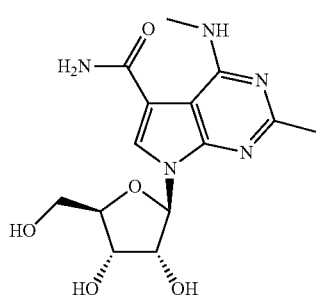
37
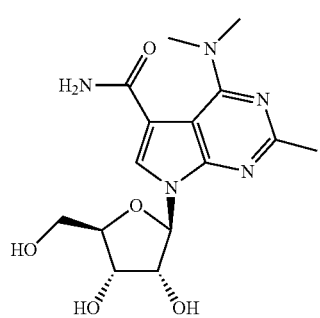

-continued
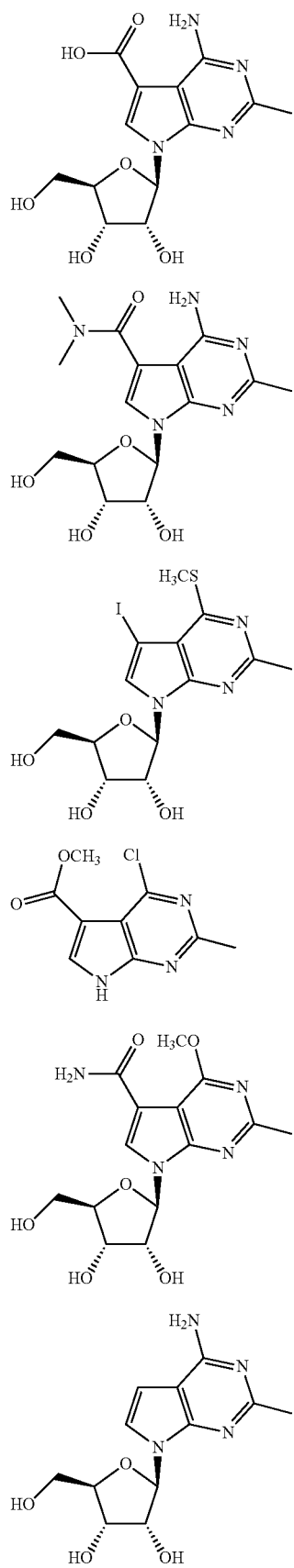
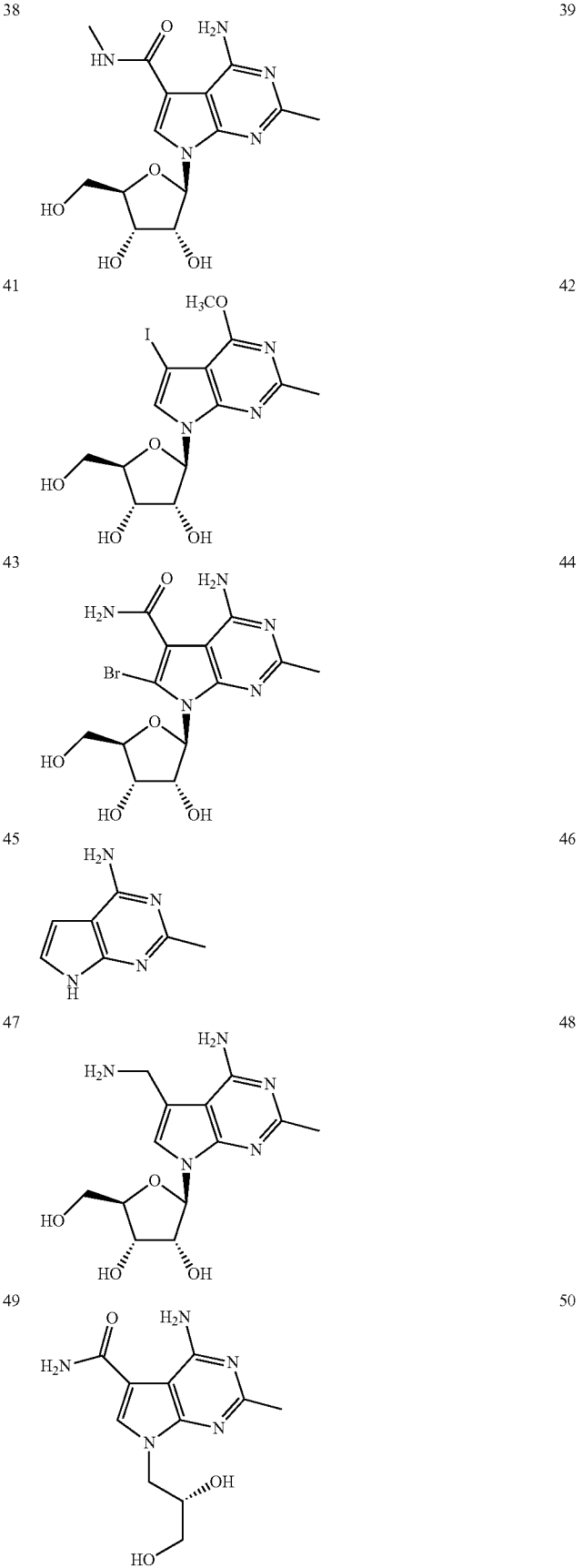

-continued
| 93 | 94 |
|---|---|
| 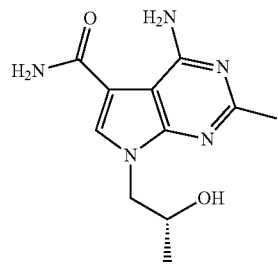 51 | 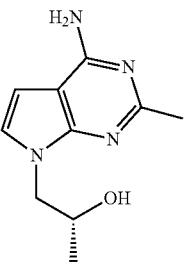 54 |
| 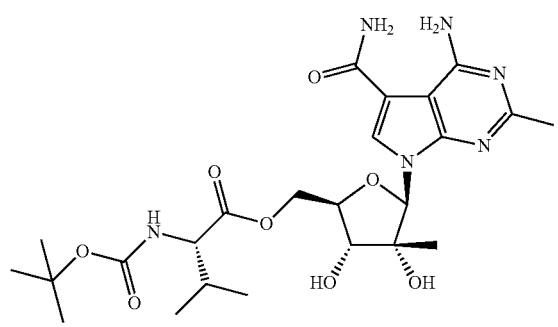 61 | 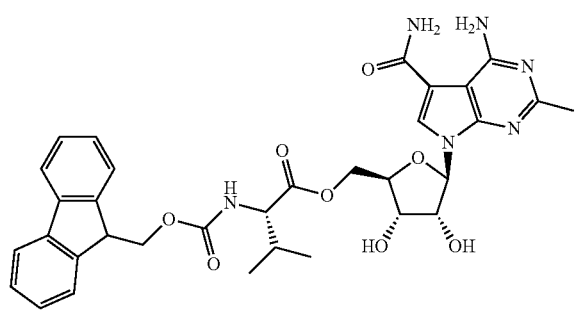 63 |
| 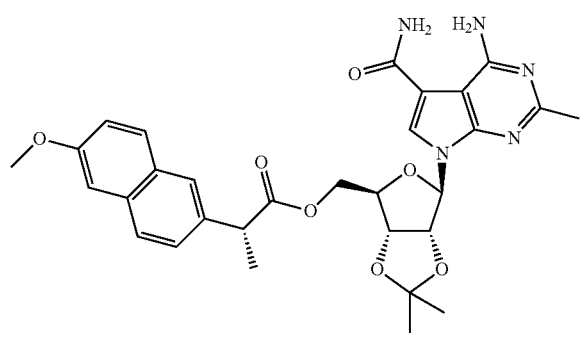 65 | 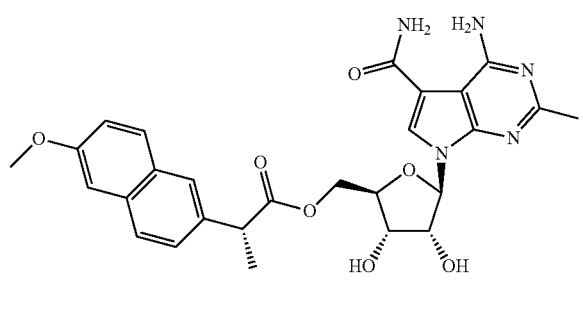 66 |
| 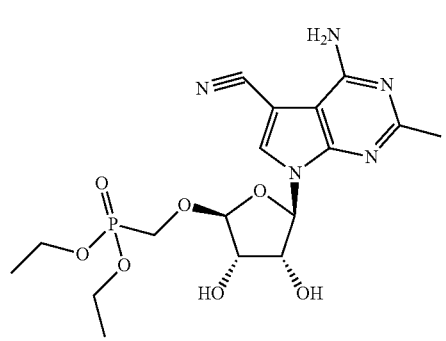 68 | 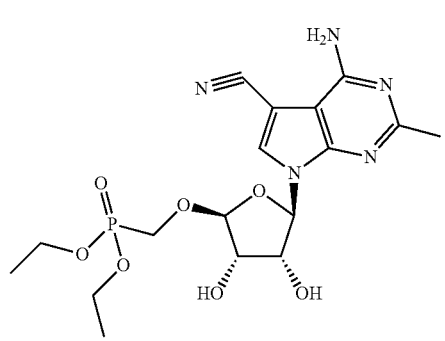 69 |
| 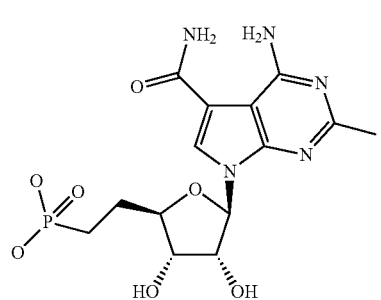 72 | 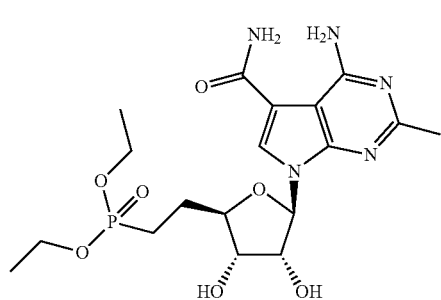 73 |

-continued
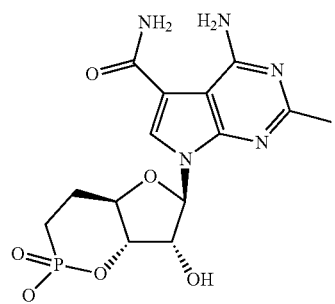
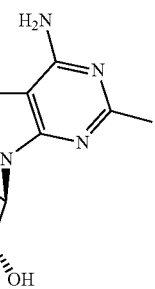
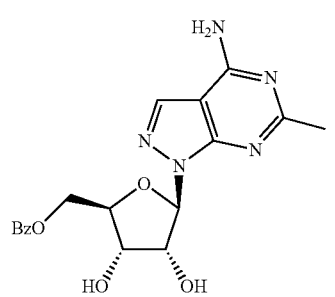
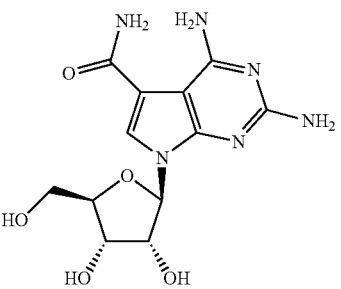
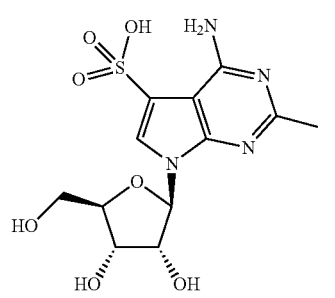
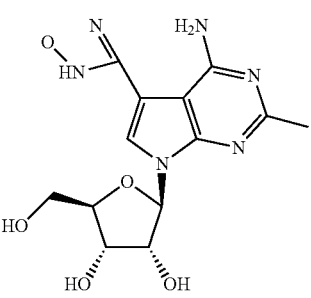
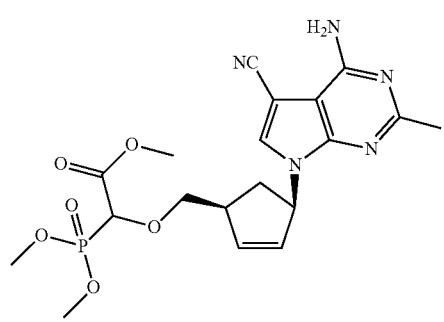
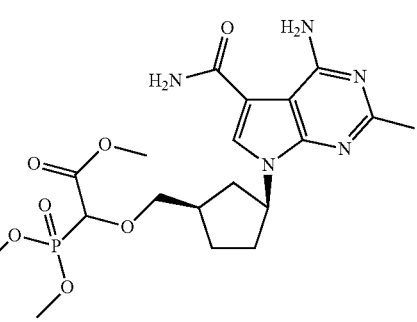
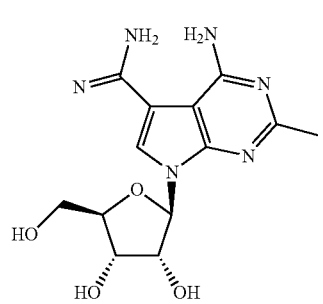
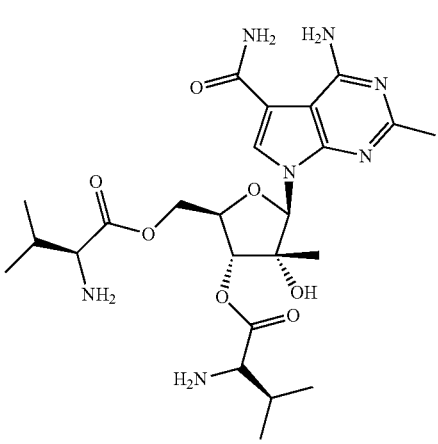

-continued
94
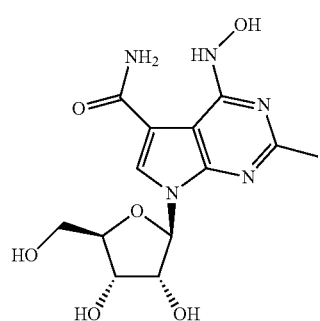
95
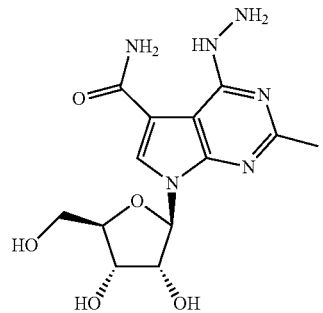
96
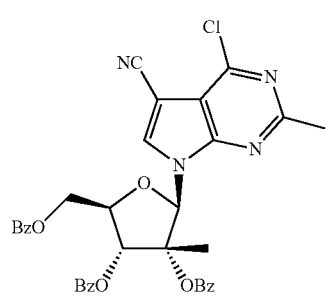
98
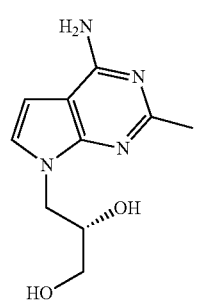
100
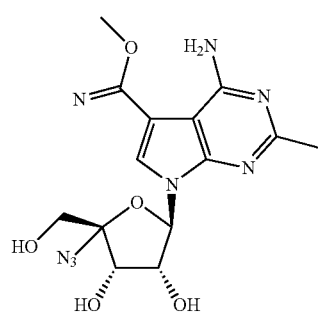
103
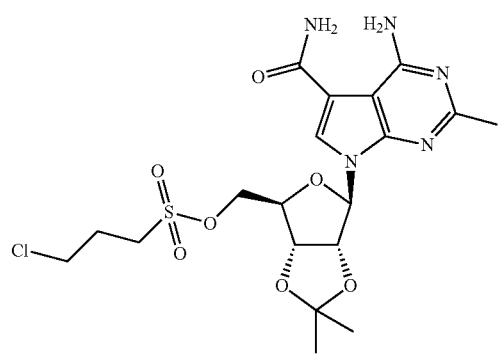
104
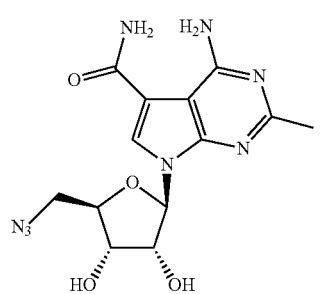
106
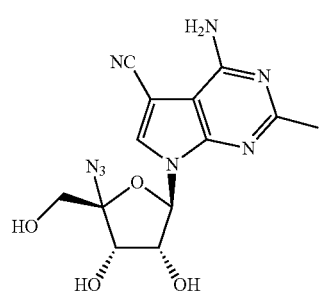
108
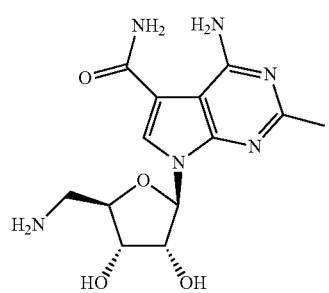
110
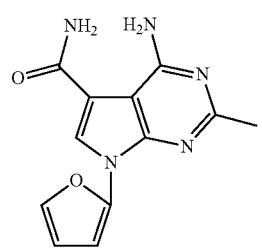

-continued
| | | | |
|---|---|---|---|
| 114 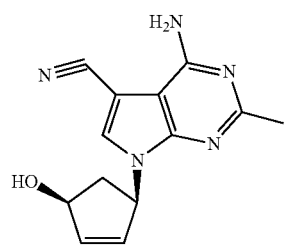 | 115 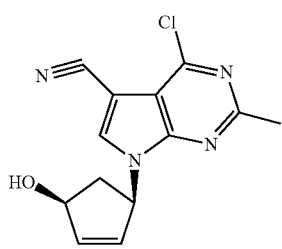 |
| 116 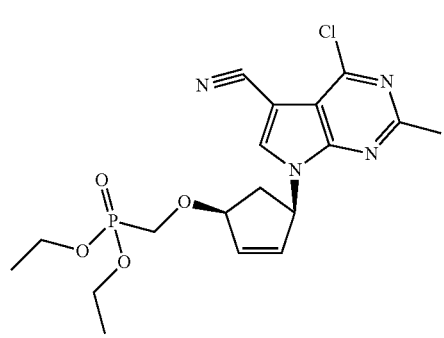 | 117 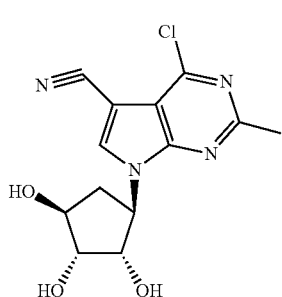 |
| 120 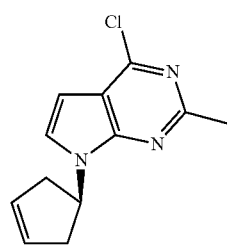 | 121 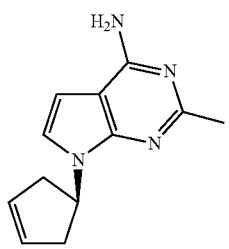 |
| 122 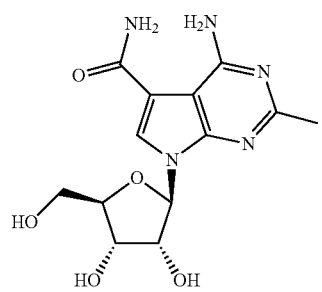 | 123 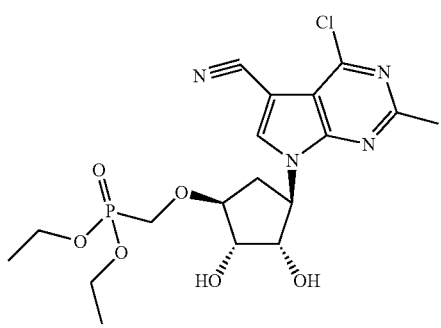 |
| 124 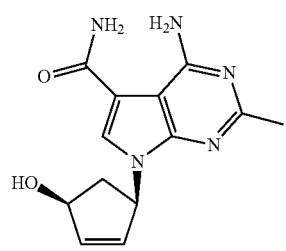 | 125 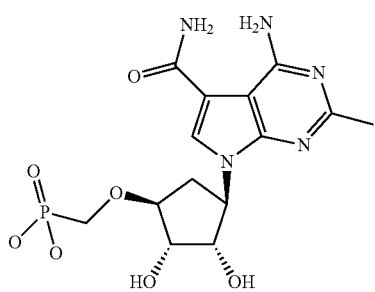 |

-continued
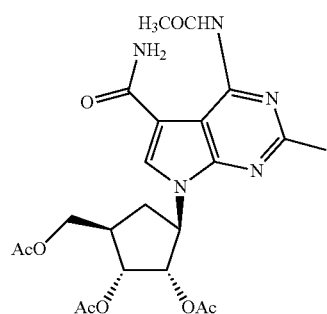 128
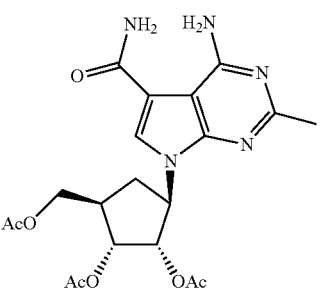 129
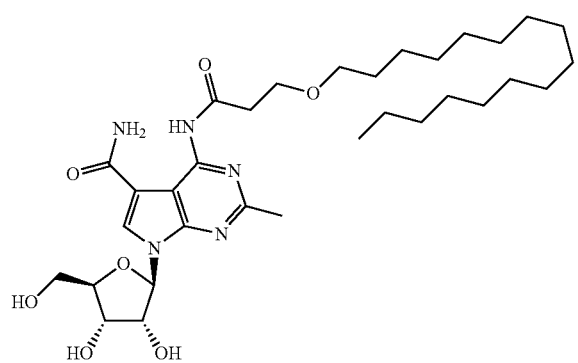 130
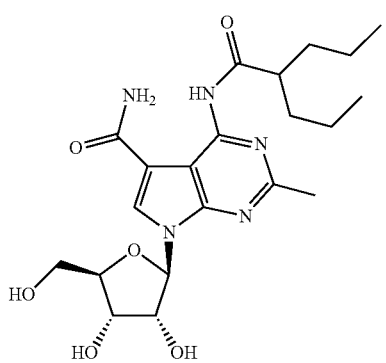 131
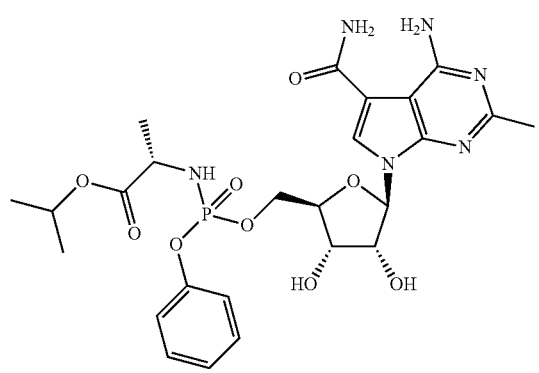 132
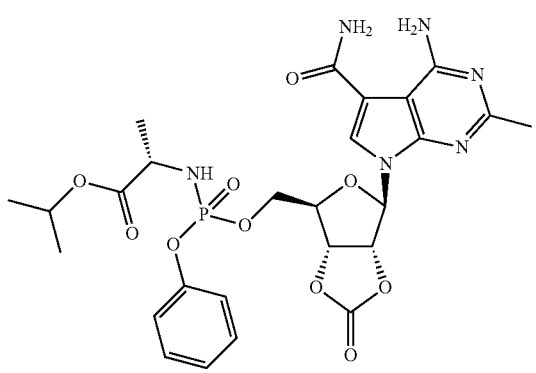 134
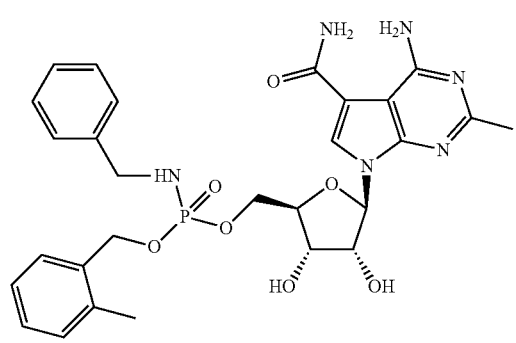 136
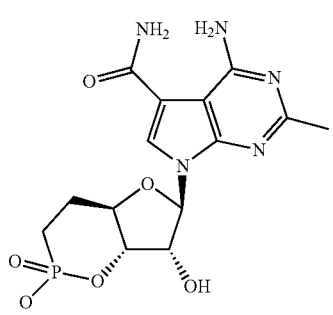 138

-continued
140
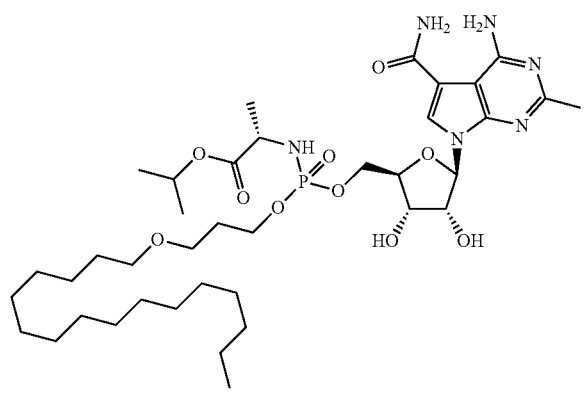
142
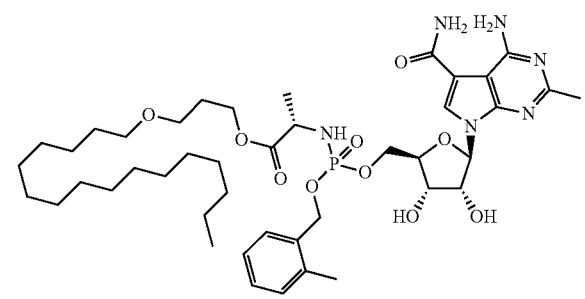
144
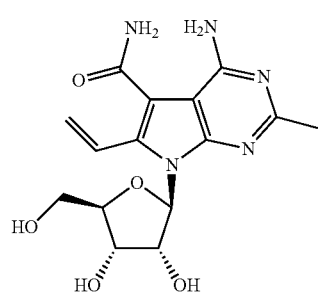
9
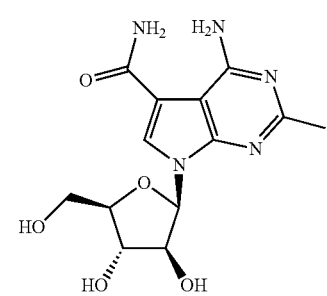
13
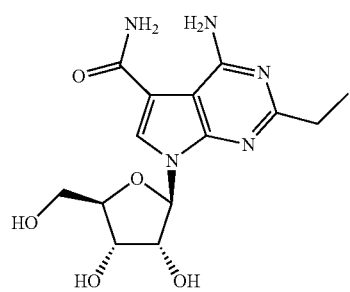
15
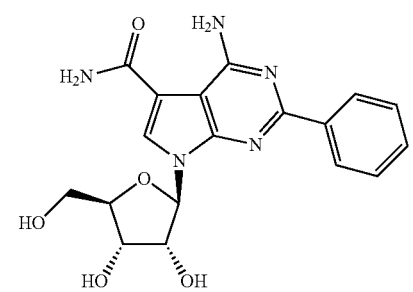
23
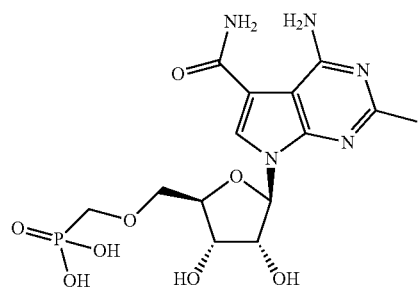
24
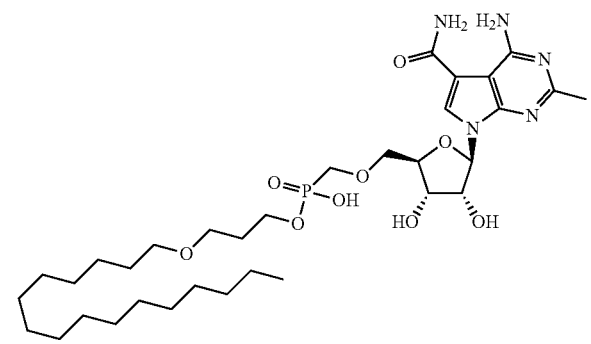
25
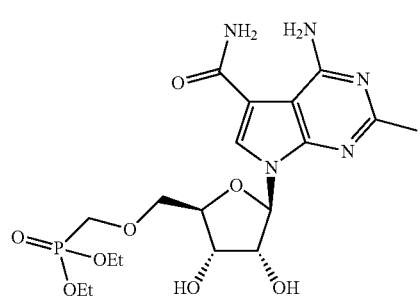
26
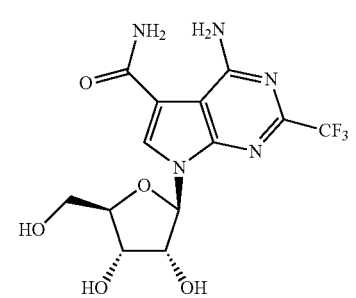

105
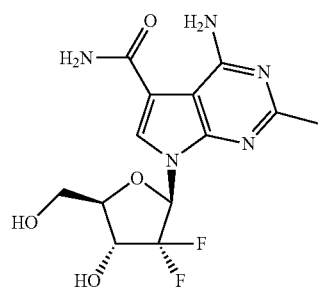
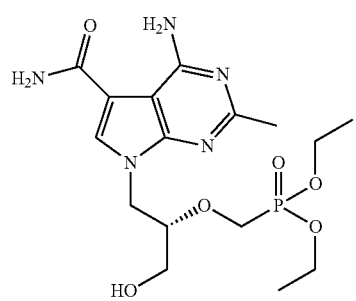
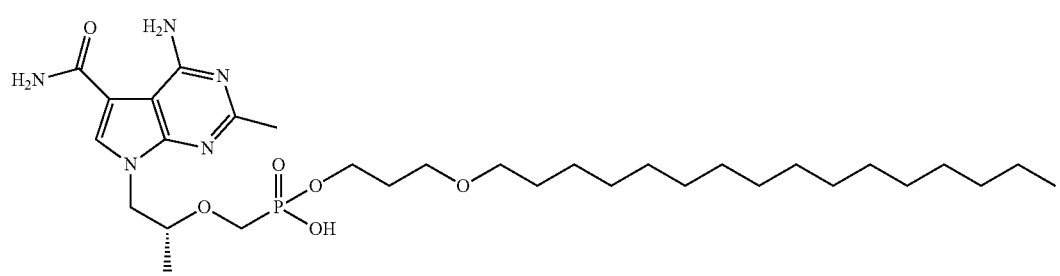
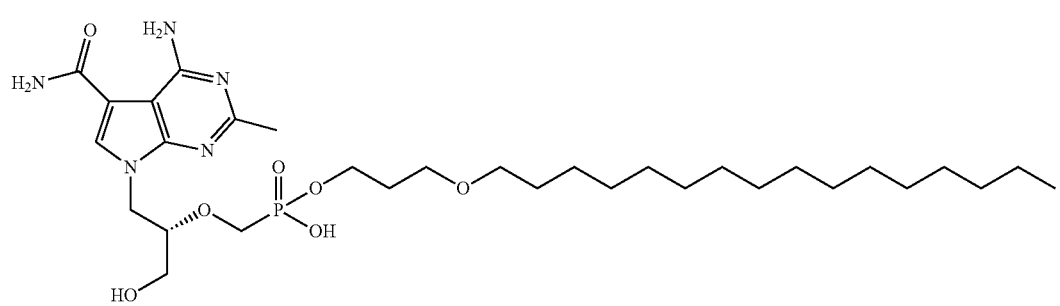
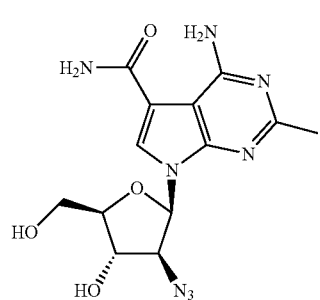
106
-continued
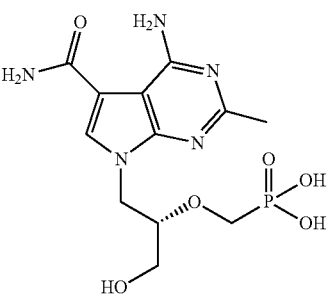
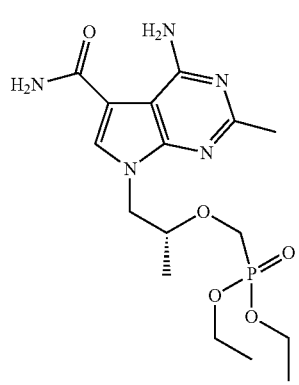

-continued
59
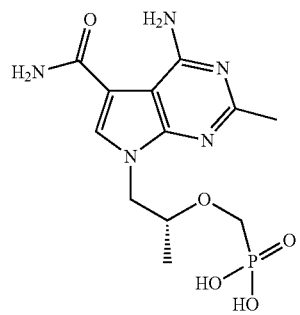
60
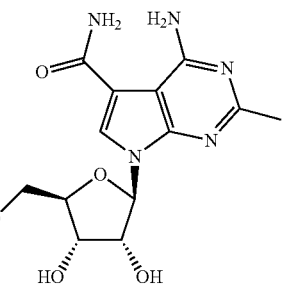
62
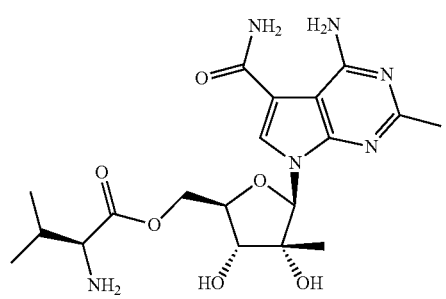
64
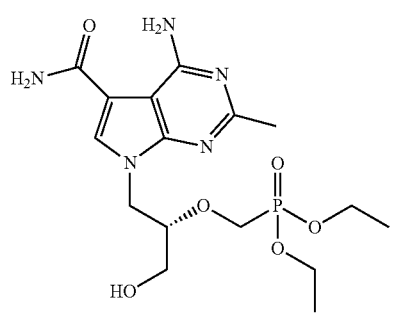
67
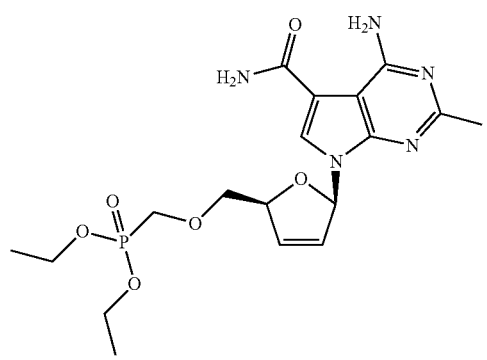
70
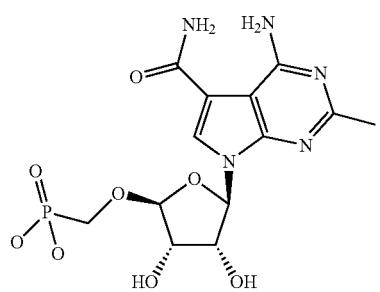
74
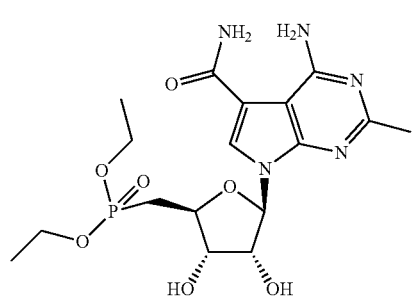
75
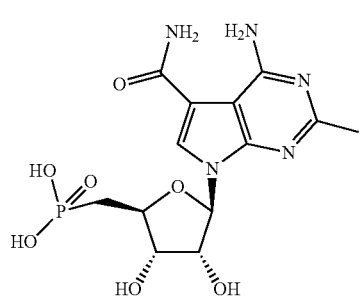

-continued
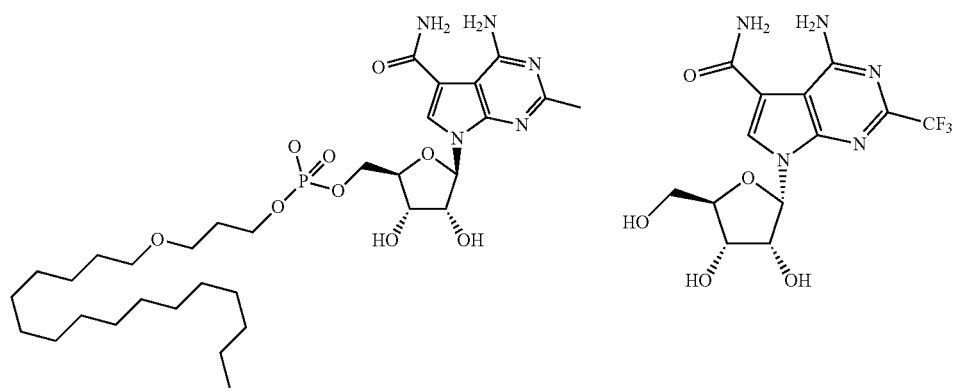
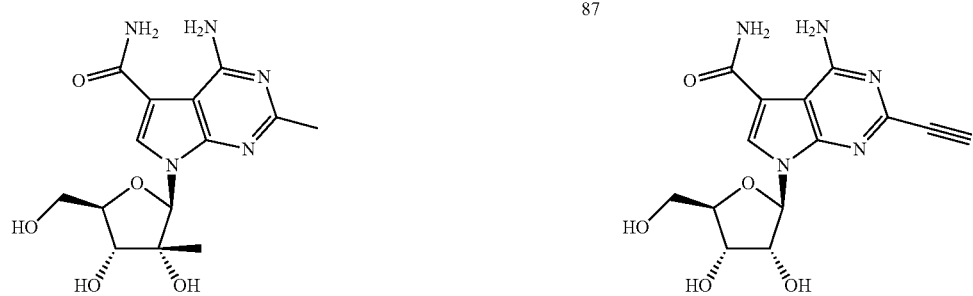
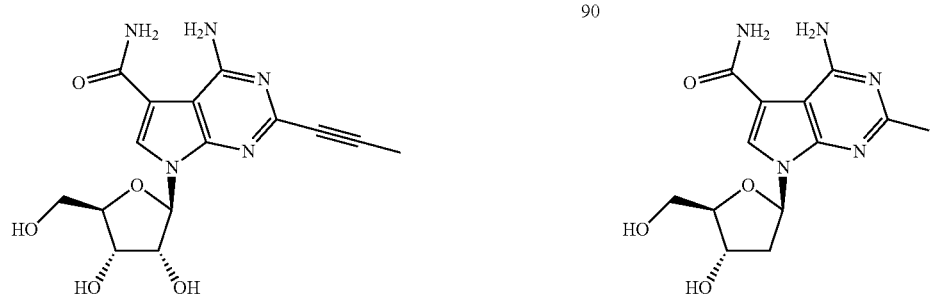
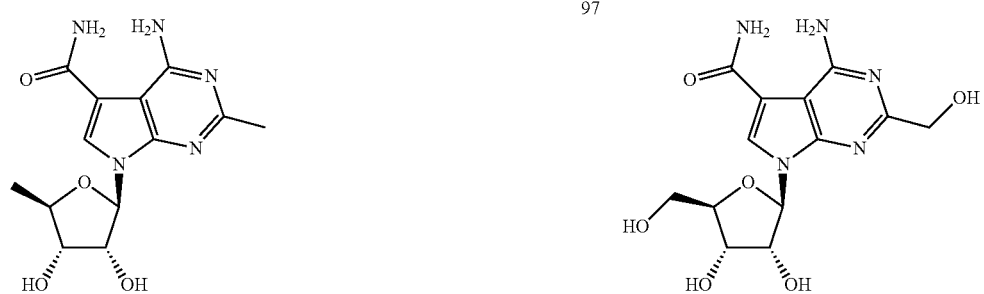
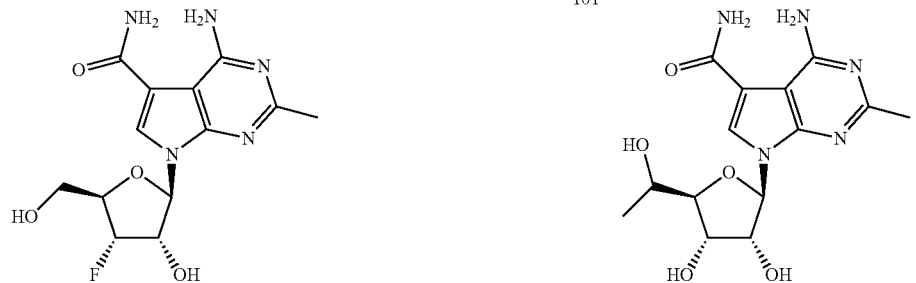

-continued

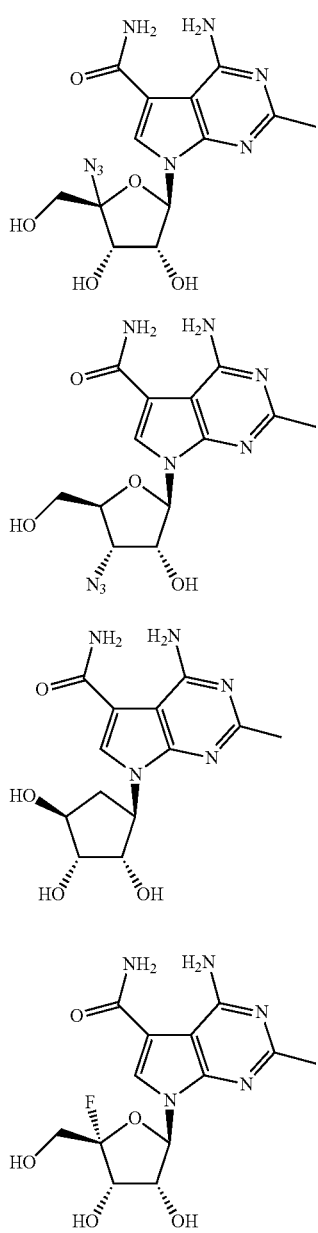
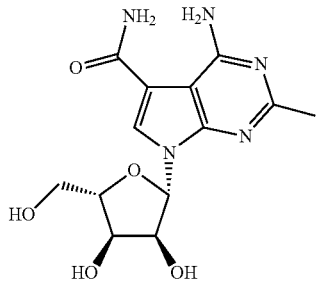
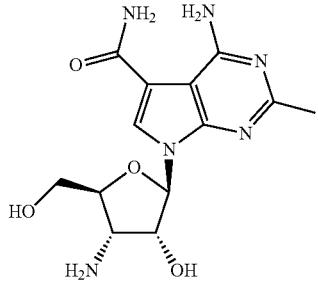
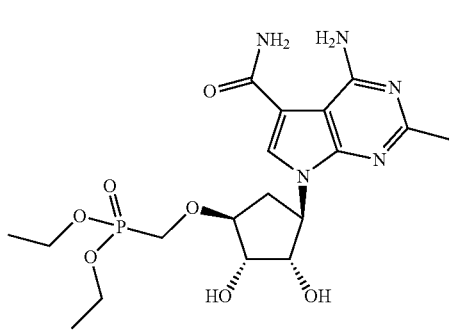
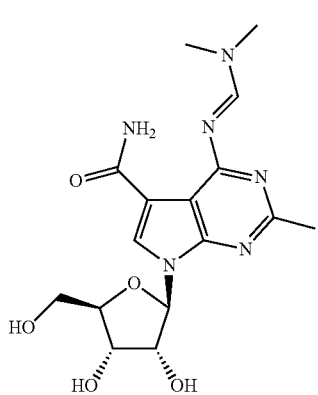

or pharmaceutically acceptable salts, solvates, enantiomers, diastereomers, racemates or mixtures thereof.

The HPLC plots were recorded on a Zorbax Eclipse Plus C18 column (4.6×50 mm×1.8 μm). The first mobile phase was 97.5% water: 2.5% acetonitrile: 0.05% trifluoroacetic acid. The second mobile phase was 97.5% acetonitrile: 2.5% water: 0.05% trifluoroacetic acid.

¹HNMR were recorded at 300 MHz unless otherwise specified.

Antiviral and Cytotoxicity Assays

Cells Culture and Virus Strains:

Human foreskin fibroblast (HFF) cells were prepared from human foreskin tissue. The tissue was incubated at in cell culture media consisting of minimum essential media (MEM) with Earle's salts supplemented with 10% fetal bovine serum (FBS), and standard concentrations of L-glutamine, fungizone, and vancomycin. Tissue was then placed in phosphate buffered saline (PBS), minced, rinsed to remove the red blood cells, and resuspended in trypsin/EDTA solution. The tissue suspension was incubated at 37° C. and gently agitated to disperse the cells, which were then collected by centrifugation. Cells were resuspended in media and placed in a tissue culture flask and incubated at 37° C. in a humidified $CO_2$ incubator. The media was then replaced with fresh media and the cell growth was monitored daily until a confluent cell monolayer was formed. The HFF cells were then expanded through serial passages in standard growth medium of MEM with Earl's salts supplemented with 10% FBS, L-glutamine, penicillin, and gentamycin. The cells were passaged routinely and used for assays at or below passage 10.

Influenza Virus:

Influenza viruses were passaged in canine kidney cells to create working stocks, which were used for the antiviral assays.

Antiviral Assays:

Each experiment that evaluated the antiviral activity of the compounds included both positive and negative control compounds to ensure the performance of each assay. Concurrent assessment of cytotoxicity was performed when possible at equivalent levels of compound exposure. Methods are presented on effective concentrations giving 50% reductions in viral replication in vitro ($EC_{50}$), concentrations producing 50% reduction in cell viability ($CC_{50}$) and selectivity index (SI, calculated as $CC_{50}$ divided by $EC_{50}$). When sufficient material was available, multiple assays were performed for each compound evaluation to obtain statistical data.

Cytotoxicity Assays:

Every antiviral assay included a parallel cytotoxicity assay with the same cells used for each virus, the same cell number, the same drug concentrations, and the same incubation times to provide the same drug exposure. To ensure that the cytotoxicity of all compounds could be compared directly, a standard neutral red uptake cytotoxicity assay for all compounds in confluent HFF cells with a 7 d incubation period was performed.

Neutral Red-Uptake Cytotoxicity Assays:

Each compound was evaluated in a standard cytotoxicity assay by standard methods. Briefly, HFF cells were seeded into tissue culture plates in standard tissue culture medium. After 24 h of incubation, medium was replaced with maintenance cell culture medium and compounds were added and then 5-fold serial dilutions were then used to generate a series of compound concentrations. Assay plates were incubated for 7 d, and neutral red solution in PBS was added to each well and the plates incubated for 1 h. The stain was then removed, the plates rinsed with PBS and the dye internalized by viable cells was solubilized in PBS supplemented with 50% ethanol and 1% glacial acetic acid. The optical density was then determined and $CC_{50}$ values were interpolated from the experimental data.

For all plaque-reduction assays in HFF cells, neutral red cytotoxicity assays were performed on a parallel set of 6-well plates containing uninfected HFF cells that received the same compound concentrations as used for the antiviral assays. The cytotoxicity plates were removed from the incubator on the same day as each antiviral assay and the cell monolayer was stained with a neutral red solution in PBS. The dye was then removed, residual dye rinsed from the cells with PBS, and cell monolayers were inspected visually for any signs of toxicity. The cell viability was determined using a Cell Proliferation Assay according to manufacturer's instructions.

Cell Proliferation Assays:

The inhibition of HFF cell proliferation was used to refine estimates of cytotoxicity for some compounds and was performed according to a standard procedure used in the laboratory. Cells were seeded at a low density into plates using standard culture medium. After 24 h, the medium was aspirated, and a range of compound solutions in the growth medium was prepared. The plates were incubated for 72 h at 37° C., and the cells were then dislodged with trypsin and counted. Compound concentrations that reduced cell proliferation by 50% were interpolated from experimental data.

Cytotoxicity in Lymphocyte Assays:

Cell viability in all assays with lymphocytes was assessed with a luminescent Cell Viability Assay. Briefly, assay plates were incubated at ambient temperature for 30 min then luminescent reagent was added to each well and the plates were mixed to lyse the cells. Plates were then incubated for at ambient temperature and the luminescence was quantified on a luminometer. Standard methods were used to calculate drug concentrations that inhibited the proliferation of cells by 50% ($CC_{50}$).

Mouse Norovirus (MNV) Assay:

RAW cells were incubated at 37° C. with 5% $CO_2$ in cell culture media. The mouse norovirus isolate used in this assay was isolated from a wild mouse.

Serial dilutions of test compounds in DMEM were added to tissue culture-treated plates. Cell suspension were added to the compound dilutions in the plate, and incubated at 37° C. with 5% $CO_2$ for 2 days. Each assay plate included uninfected cell controls and untreated virus control wells. After 2 days of incubation, aqueous MTS Reagent (was added as directed by manufacturer in each well and incubated at 37° C. until the untreated-cell controls developed a 490 nm absorbance between 1.1 and 1.8. The final absorbance readings were read, and software was used to calculate the concentration that protected MNV-infected RAW cells by 50% compared to uninfected cell controls (EC50).

Human Norovirus Assays:

Antiviral activity against a human Norovirus (NoV) was assessed in a 3-day assay using a stably-expressing human Norovirus replicon cell line, maintained as sub-confluent cultures. In some embodiments, 4 doses (10-fold or 3-fold steps), in triplicate can be used. Antiviral activity was determined by blot hybridization analysis of intracellular NoV RNA (normalized to the level of cellular β-actin RNA in each culture sample). Cytotoxicity was assessed by neutral red dye uptake in cultures maintained in parallel plates (Korba and Gerin, 1992, Antivir. Res. 19:55).

$EC_{50}$, and $CC_{50}$ values were calculated by linear regression analysis using data combined from all treated cultures (Korba & Gerin, 1992, Antivir. Res. 19:55; Okuse, et al., 2005, Antivir. Res. 65:23). Standard deviations for $EC_{50}$ and $EC_{90}$ values were calculated from the standard errors generated by the regression analyses. $EC_{50}$ and $EC_{90}$ are drug concentrations at which a 2-fold, or a 10-fold depression of intracellular NoV RNA (relative to the average levels in untreated cultures), respectively, is observed. $CC_{50}$ is the drug concentration at which a 2-fold lower level of neutral red dye uptake (relative to the average levels in untreated cultures) is observed. The Selectivity index (S.I.) is calculated as $CC_{50}/EC_{50}$. Recombinant human interferon 2b (PBL laboratories, Inc.) is used as an assay control.

BKV $EC_{50}$ in VERO Cells:

Tissue culture plates were seeded with Vero cells in DMEM containing 2% Hyclone Standard Fetal Bovine Serum and 1% Hyclone Penicillin and Streptomycin. Cells were inoculated with BKV. Serial dilutions of test compounds were added to the cells and plates were incubated for 10 days at 37° C. in 5% $CO_2$. After the 10-day incubation, supernatant was mixed with lysis buffer. Each plate was incubated C. Supernatant BKV DNA was measured by quantitative polymerase chain reaction (qPCR) using forward and reverse BKV PCR primers, and a FAM-labeled probe. Absolute quantitation of viral copy number was performed using a standard curve with dilutions of a BKV DNA amplicon containing sequences homologous to the amplified fragment.

Plaque-Reduction Assays for HSV-1, HSV-2, VZV and HCMV:

Monolayers of cells were prepared in six-well plates and incubated at to allow the cells to reach confluency. Media was then aspirated from the wells and of virus was added to each of three wells to yield 20-30 plaques in each well. The virus was allowed to adsorb to the cells for 1 h and the plates were rocked gently every 15 min to redistribute the media. Compounds were diluted in maintenance cell culture media consisting of MEM with Earl's salts supplemented with 2% FBS, L-glutamine, penicillin, and gentamycin. Solutions were added to duplicate wells and the plates were incubated for various times, depending on the virus used. The plaque-reduction assay with HSV-1 strain F was performed in a similar manner but with Vero cells infected one day after plating. For HSV-1 and -2, the monolayers were stained with 1% crystal violet in 20% methanol and the unbound dye removed by washing with $dH_2O$. For assays with HCMV and VZV, the cell monolayer was stained with 1% Neutral Red solution for 4 h then the stain was aspirated and the cells were washed with PBS. For all assays, plaques were enumerated using a stereomicroscope and the concentration of compound that reduced plaque formation by 50% (EC50) was interpolated from the experimental data.

Plaque-Reduction Assays for MCMV:

Mouse embryo fibroblast cells were prepared from mouse embryos using a procedure similar to that outlined above for HFF cells and suspended in tissue culture media as described above and seeded into plates and incubated. The medium was aspirated and the cell monolayers were infected with MCMV. The infected cells were then incubated at 37° C. for 1 h and the plates were rocked occasionally to ensure that the media covered the entire monolayer. Compounds were serially diluted in tissue maintenance cell culture media described above and the solutions were added to the infected monolayers. Infected monolayers were incubated for 7 d and then stained with Neutral Red solution as described above. Plaques were enumerated and $EC_{50}$ values were interpolated from the experimental data by standard methods.

DNA Quantitation Assays for EBV and HHV-6B:

Assays for EBV were performed in Akata cells that were induced to undergo a lytic infection with goat anti-human IgG antibody by standard methods. Experimental compounds were diluted in plates. Akata cells were added to the plates and incubated. For HHV-6, compounds were serially diluted then uninfected HSB-2 or Molt-3 cells were added to each well. Infection was initiated by adding HHV-6A infected HSB-2 cells, or HHV-6B infected Molt-3 cells, and incubated for 7 d at 37° C. For all assays, denaturation buffer was added to each well to denature the DNA and an aliquot was aspirated through a nylon membrane. The membranes were then allowed to dry before equilibration in DIG. Specific digoxigenin (DIG)-labeled probes were prepared for each virus according to the manufacturer's protocol. Detection of specifically bound DIG probe was performed with anti-DIG antibody using the manufacturer's protocol. An image of the photographic film was captured and quantified and compound concentrations sufficient to reduce the accumulation of viral DNA by 50% (EC50), were interpolated from the experimental data.

DNA Quantitation Assays for HHV-8:

Test compounds were diluted in duplicate wells. BCBL-1 cells were induced to undergo a lytic infection by the addition of phorbol 12-myristate 13-acetate cells were added to each well in the plate. Cells were incubated for 7 d at 37° C. in a humidified $CO_2$ incubator then total DNA was prepared. Viral DNA was quantified by real time PCR Compound concentrations sufficient to reduce genome copy number by 50% were calculated from experimental data.

Cell-Based Assays for Flu:

For dose-response curves, individual drugs were added to MDCK cells in 96-well microplates. Untreated wells of infected cells (virus controls) and uninfected cells (cell controls) were included on each test plate. At three days post-infection, the virus control wells exhibited 100% cytopathology. The extent of viral cytopathology in each well was determined microscopically by inspection and by staining with neutral red (NR). Briefly, the cells were stained with NR diluted in MEM to determine cell viability. Two hours later the plates were processed for quantification of NR uptake into viable cells. The amount of NR taken up by cells was determined spectrophotometrically.

qPCR Assays for BKV and JCV:

Primary assays for BK virus were performed in 96-well plates containing monolayers of HFF cells. Compound dilutions were prepared in plates containing cells which were subsequently infected at with the Gardner strain of BK virus. After a 7 d incubation, total DNA was prepared with a purification kit and genome copy number was quantified by real time PCR. Compounds that were positive in this assay were confirmed in a similar assay in 96-well plates with the compounds added 1 h following infection to identify compounds that inhibit early stages of replication including adsorption and penetration. Genome copy number was determined by methods described above.

Primary evaluation of compounds against JC virus were also performed by methods similar to those for BK virus primary assays. Secondary assays against JCV were performed in COS7 cells by methods similar to those for BK virus to identify compounds that inhibited adsorption or penetration of the virus.

Hepatitis C Virus Assay:

Luciferase reporter (Replicon)/CytoTox-1 (Toxicity). Compounds were screened for anti-HCV activity using a luciferase (Luc) reporter gene endpoint in the HCV primary assay. The Luc reporter was used as an indirect measure of HCV replication as its activity is directly proportional to HCV RNA levels. Assessment of cytotoxicity is conducted in parallel. Drug stocks were prepared in DMSO unless otherwise specified and were diluted with tissue culture medium to the desired high-test concentration. For each assay, the compounds were then further diluted in tissue culture medium as required. After incubation, the cells were processed to derive, where applicable, EC50 and EC90 (compound concentration reducing replicon replication by 50% and 90% respectively). CC50 (concentration decreasing cell viability by 50%) and SI50 (CC50/EC50) values were determined and reported. Anti-HCV activity was assessed with the replicon (genotype 1b or 2a) or HCVcc virus-derived Luc activity as readout; whereas the cytotoxic concentrations of drug reducing cell numbers was assessed by the CytoTox-1 cell proliferation assay according to manufacturer's protocol. Recombinant interferon alpha was used as the positive control drug to validate assay performance.

Assays for Influenza virus, RSV, and SARS CoV were Cytopathic effect/Toxicity-based assay using CellTiter-Glo. The antiviral cytoprotection assays examine the effects of compounds at designated dose-response concentrations in specific cell types to test the efficacy of the compounds in preventing the virus-induced cytopathic effect. Ribavirin was included as a positive control drug for influenza and RSV, while calpain IV inhibitor was used for SARS antiviral assays. Subconfluent cultures of cells were plated into 96-well plates for the analysis of cell viability (cytotoxicity) and antiviral activity (CPE). For the standard assay, drugs were added to the cells 24 hours later. The CPE wells also received 100 tissue culture infectious doses (100 TCID50s) of titered virus. 72 hours later the cell viability was determined.

Measurement of viral-induced CPE was based on quantitation of ATP, an indicator of metabolically active cells. The CPE assay employed a commercially available Luminescent Cell Viability Kit, and was a reliable method for determining cytotoxicity and cell proliferation in culture. The procedure involved adding the single reagent directly to previously cultured, subconfluent cells in media. This induced cell lysis and the production of a bioluminescent signal (half-life greater than 5 hours, depending on the cell type) that was proportional to the amount of ATP present (which is a biomarker for viability).

Assays for Dengue (DENV), West Nile Virus (WNV), Yellow Fever Virus (YFV), Rift Valley Fever Virus (RVFV), Venezuelan Equine Encephalitis Virus (VEEV):

Primary cytopathic effect (CPE) reduction assay. Four-concentration CPE inhibition assays were performed. Confluent or near-confluent cell culture monolayers in microplates were prepared. Cells were maintained in MEM or DMEM supplemented with FBS as required for each cell line. For antiviral assays the same medium is used but with FBS reduced to 2% or less and supplemented with gentamicin. The test compound was prepared at different concentrations, u. The virus control and cell control wells were on every microplate. In parallel, a known active drug was tested as a positive control drug using the same method as was applied for test compounds. The positive control was tested with each test run. The assay was set up by first removing growth media from the 96-well plates of cells. Then the test compound was applied to wells. Virus was placed in those wells designated for virus infection. Medium devoid of virus was placed in toxicity control wells and cell control wells. Virus control wells was treated similarly with virus. Plates were incubated at 37° C. with 5% $CO_2$ until maximum CPE is observed in virus control wells. The plates were then stained with neutral red for approximately two hours at 37° C. in a 5% $CO_2$ incubator. The neutral red medium was removed by complete aspiration, and the cells can be rinsed with phosphate buffered solution (PBS) to remove residual dye. The PBS is completely removed and the incorporated neutral red was eluted with buffer. The dye content in each well is quantified using a spectrophotometer. The dye content in each set of wells was converted to a percentage of dye present in untreated control wells using a Microsoft Excel computer-based spreadsheet. The 50% effective (EC50) concentrations and 50% cytotoxic (CC50) concentrations were then calculated by linear regression analysis. The quotient of CC50 divided by EC50 gives the selectivity index (SI) value.

Assays for Adenovirus (AdV), Measles (MEV), Poliovirus (POV) and Enterovirus (ENTV):

The primary screen was a cytopathic effect (CPE) reduction assay. Briefly, cultures of cells were infected with virus in the presence of test compounds and incubated for 4-7 days (depending on the specific virus/cells). Each virus was pre-titered such that control wells exhibited approximately 95% loss of cell viability due to virus replication. Therefore, antiviral effect, or cytoprotection, was observed when compounds prevent virus replication. Each assay plate contained cell control wells (cells only), virus control wells (cells plus virus), compound toxicity control wells (cells plus compound only), compound colorimetric control wells (compound only, no cells or virus), as well as experimental wells (compound plus cells plus virus). Cytoprotection and compound cytotoxicity were assessed by MTS dye reduction. The percent reduction in viral CPE (antiviral activity) and percent cell viability (cytotoxicity) were determined and reported.

Assays for Vaccinia Virus (VACV):

The primary assay was a cytopathic effect (CPE) reduction assay. Low passage HFF cells were trypsinized, counted, and seeded into tissue culture plates. The cells were then incubated for 24 h at 37° C. The media was then removed and MEM containing 2% FBS was added to all but the first row. In the first row, media containing the experimental drug (e.g., Compound 1) was added in triplicate wells. Media alone was added to both cell and virus control wells. The drug in the first row of wells was then diluted serially 1:5 throughout the remaining wells. The plates were then incubated for 60 minutes and a virus suspension was added to each well, excluding cell control wells which received MEM. The plates were then incubated at 37° C. in a $CO_2$ incubator. After the incubation period, media was aspirated and the cells stained with crystal violet in formalin for 4 h. The stain was then removed and the plates were rinsed until all excess stain was removed. The plates were allowed to dry for 24 h and the amount of CPE in each row determined. $EC_{50}$ and $CC_{50}$ values were determined by comparing drug treated and untreated cells using a computer program.

As set forth in Example 1, below, compound 1 has activity against mouse norovirus in vitro. In some embodiments, compound 1 has an $EC_{50}$ value of about 2.1 and a $CC_{50}$ value of about 114 against mouse norovirus. Additionally, compound 1 has activity against a wide array of DNA and RNA viruses.

Figure 2A:
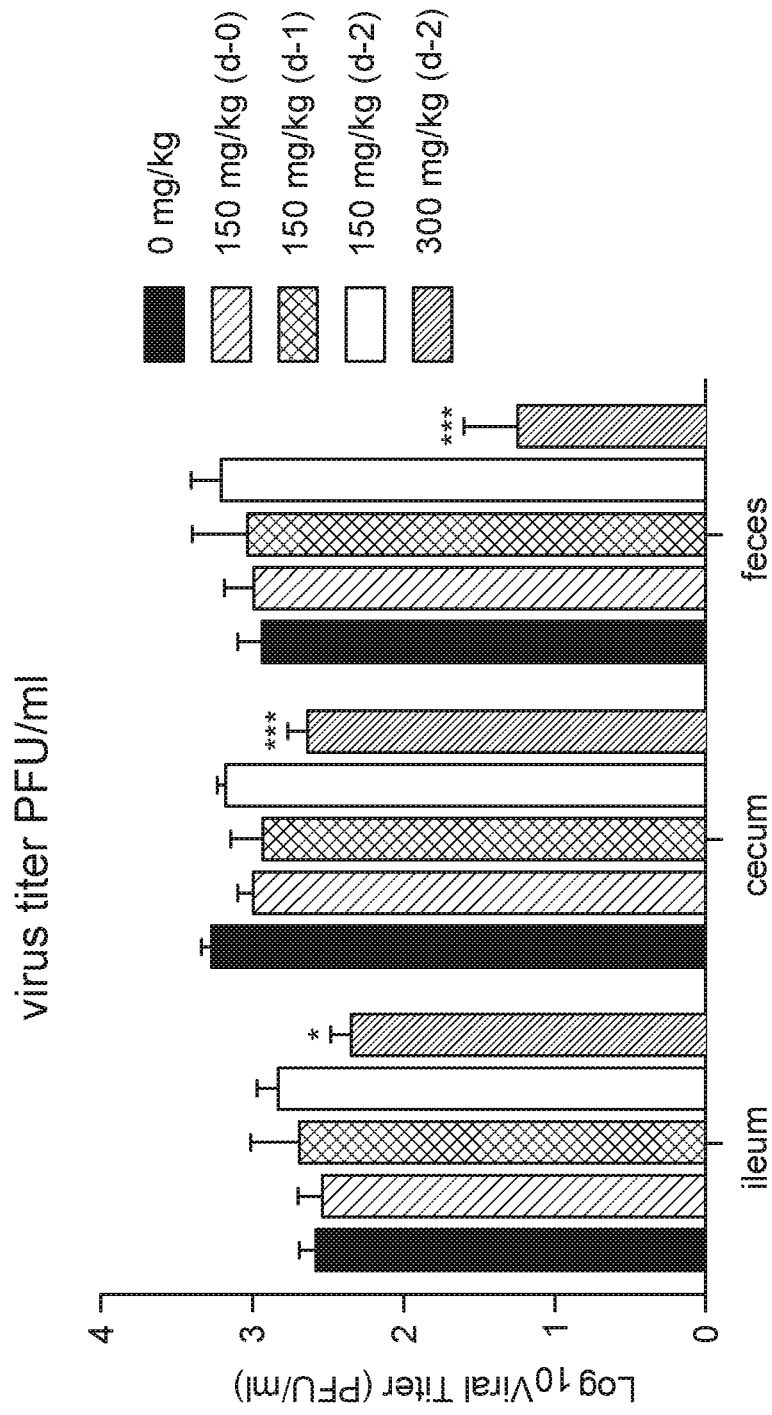
FIG. 2A shows murine norovirus titer (plaque forming units per mL) in tissue and feces harvested 3 days post-infection as part of Study No. 2.
Figure 2B:
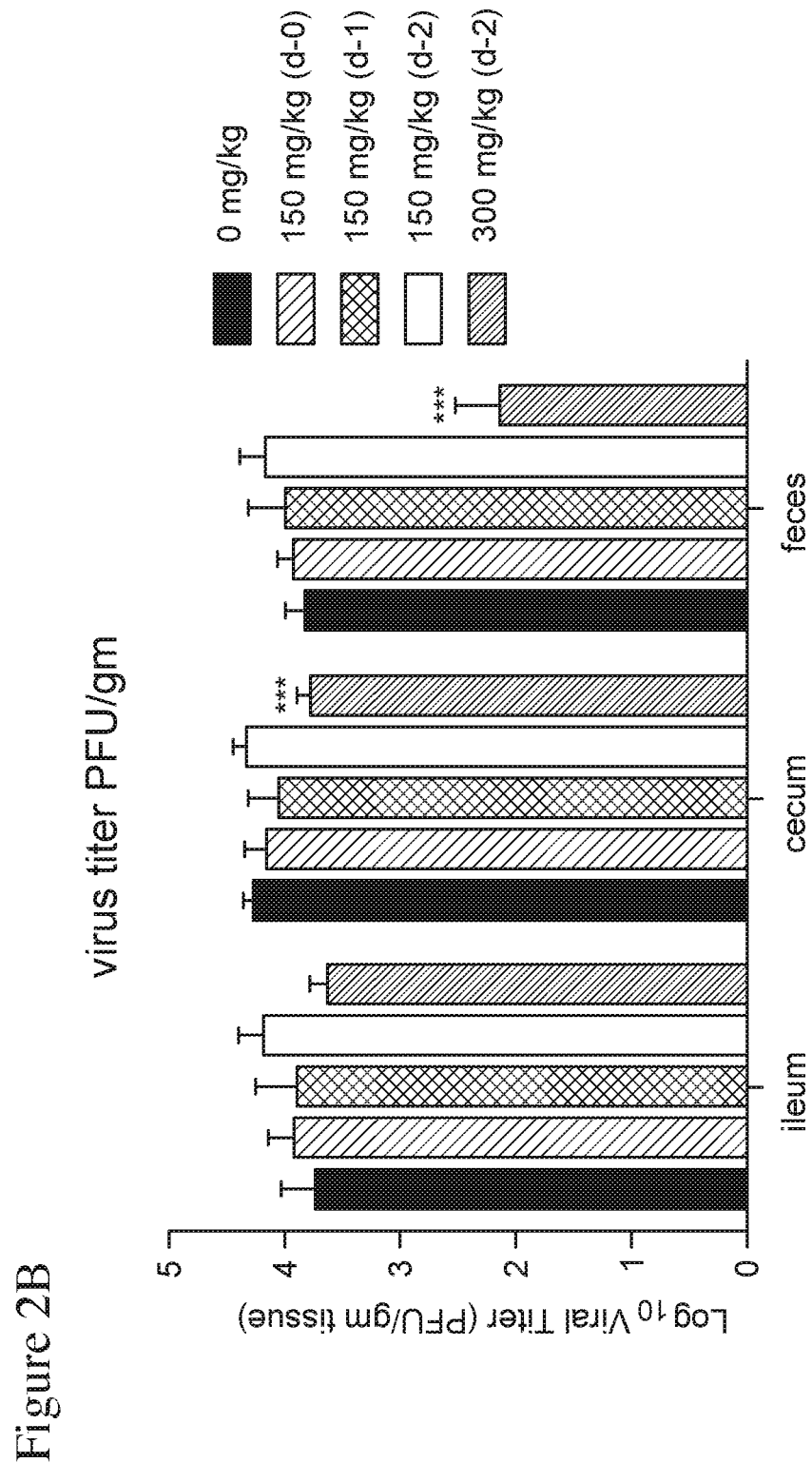
FIG. 2B shows murine norovirus titer (plaque forming units per mg of tissue) in tissue and feces harvested 3 days post-infection as part of Study No. 2.
Figure 3A:
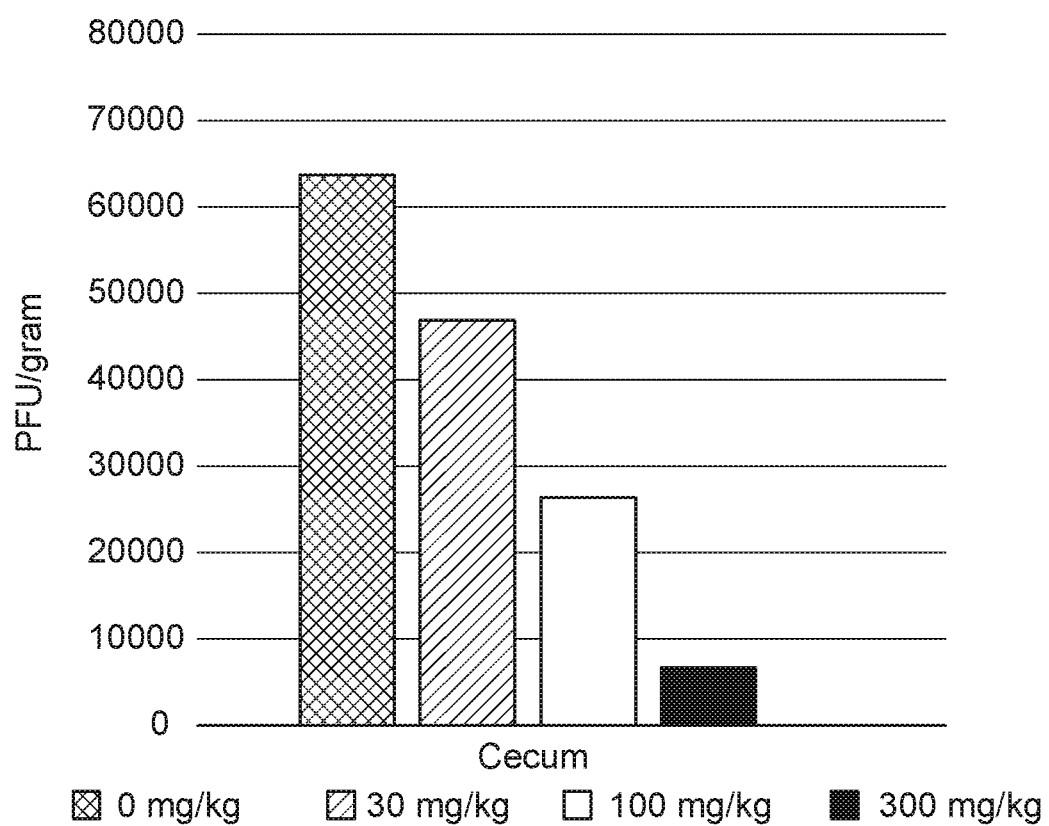
FIG. 3A shows the number of plaque forming units per gram of cecum from Study 1 on a linear scale.
Figure 3B:
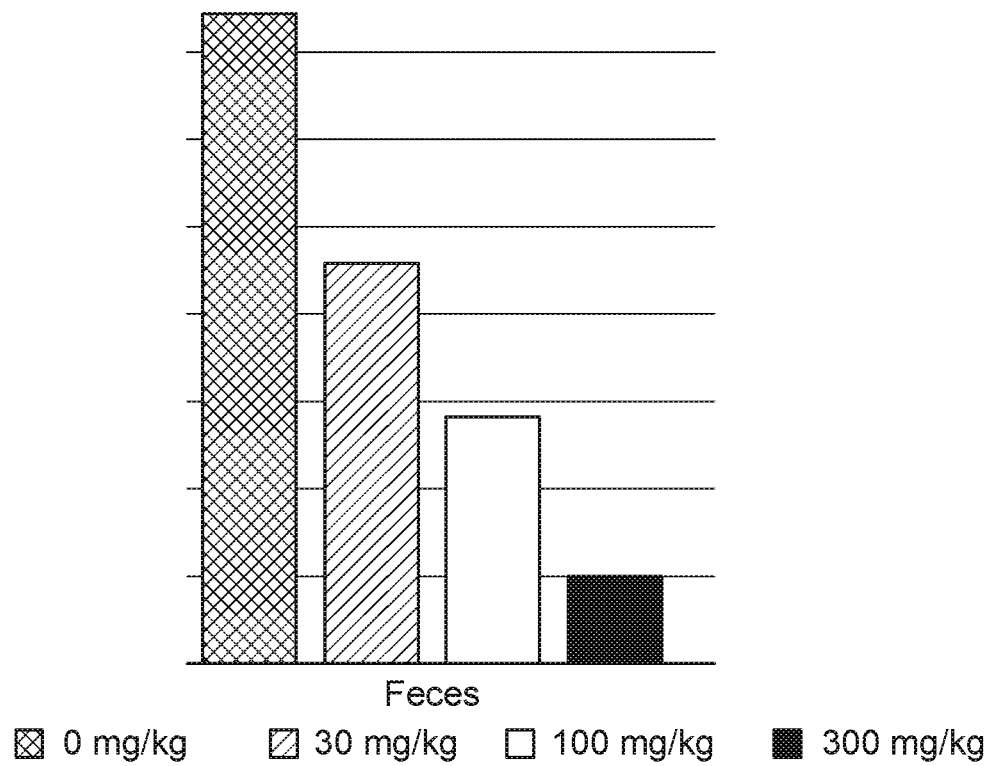
FIG. 3B shows the number of plaque forming units per gram of feces from Study 1 on a linear scale.

As set forth in Example 2, below, compound 1 has activity against mouse norovirus in vivo. As set forth in Example 2, compound 1 was able to reduce the viral load in mice infected with murine norovirus in a dose-dependent manner. The results are given in FIG. 1A and FIG. 1B, which show the reduction of viral titer in the feces and the tissue, respectively, of mice in Study 1. Additionally, FIGS. 2A and 2B show the reduction of viral titer in the feces and tissue, respectively, of mice in Study 2. FIGS. 3A and 3B show the reduction in the viral titer in the tissue and feces, respectively, of the mice in Study 1. The results are shown on a linear scale. Mice were treated with 30/mg/kg/day, or 100 mg/kg/day, or 300 mg/kg/day of compound 1 in Study 1. Mice were treated with 150/mg/kg/day, or 300 mg/kg/day of compound 1 in Study 2.

Example 3 demonstrates that compound 1 is capable of inhibiting norovirus polymerase in vitro. Without wishing to be bound by theory, it is proposed that compound 1 can protect against and treat norovirus by inhibiting norovirus polymerase.

As set forth in Example 4, compound 1 is converted to a triphosphate in vitro. As shown, when cells were incubated with compound 1, the corresponding triphosphate (i.e., compound 1-TP) was produced. The level of Compound 1-TP was 12 to 23-fold higher than compound 1 after the incubation period.

Figure 4:
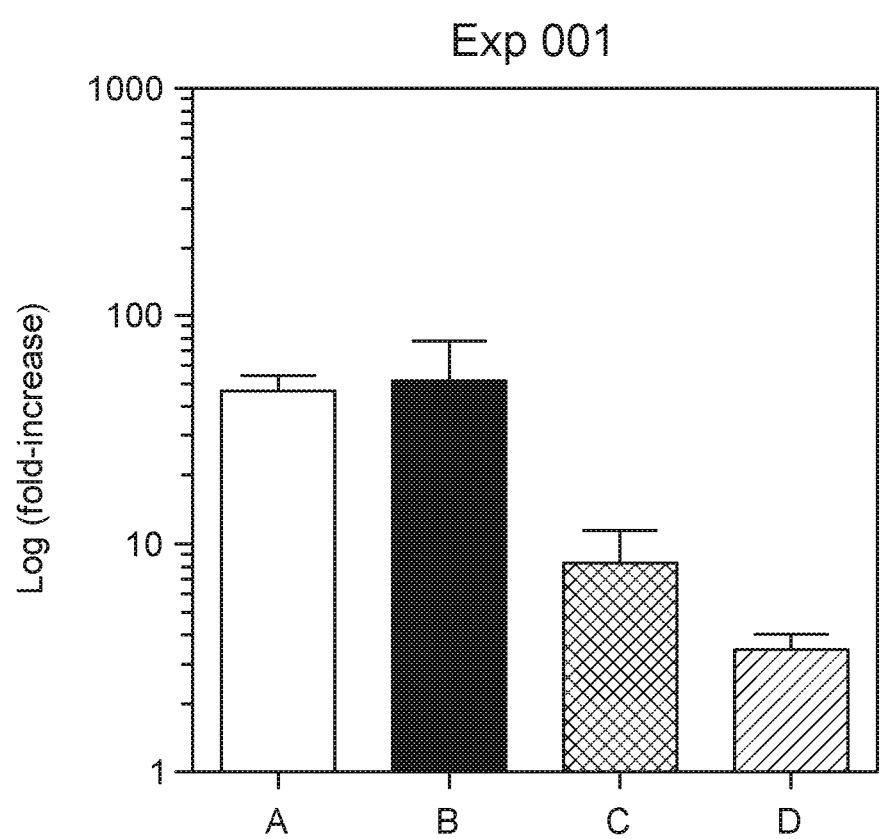
FIG. 4 shows the first duplicate of the results demonstrating the in vitro efficacy of compound 1 for inhibiting human norovirus compared to 2'-C-methylcytidine triphosphate and compound 2.
Figure 5:
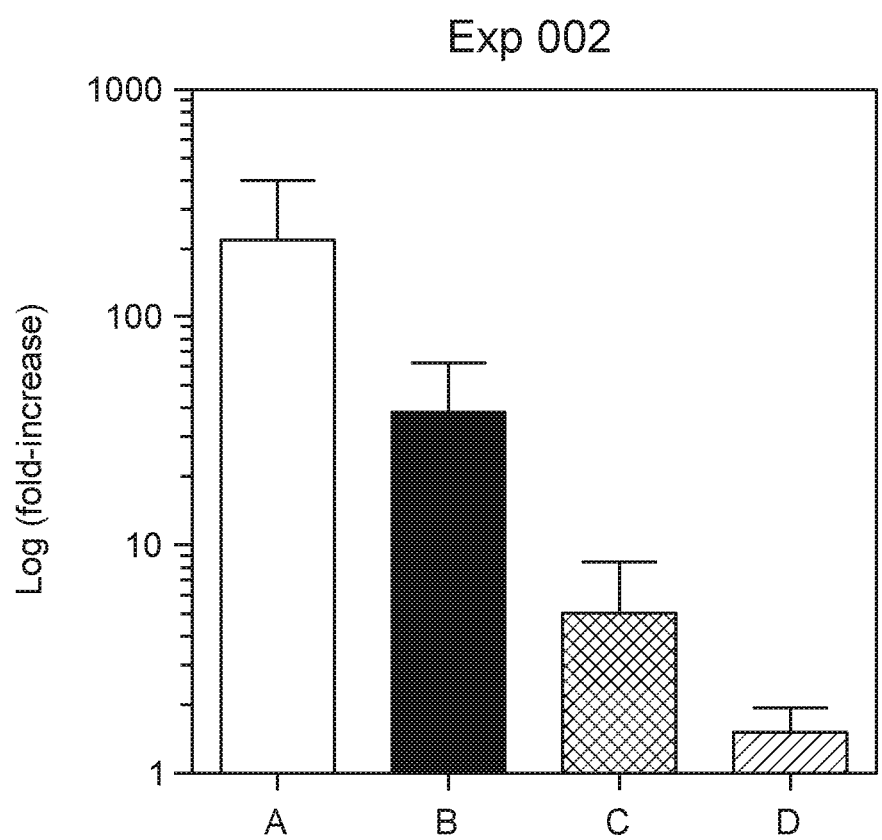
FIG. 5 shows the second duplicate of the results demonstrating the in vitro efficacy of compound 1 for inhibiting human norovirus compared to 2'-C-methylcytidine triphosphate and compound 2.
Figure 6:
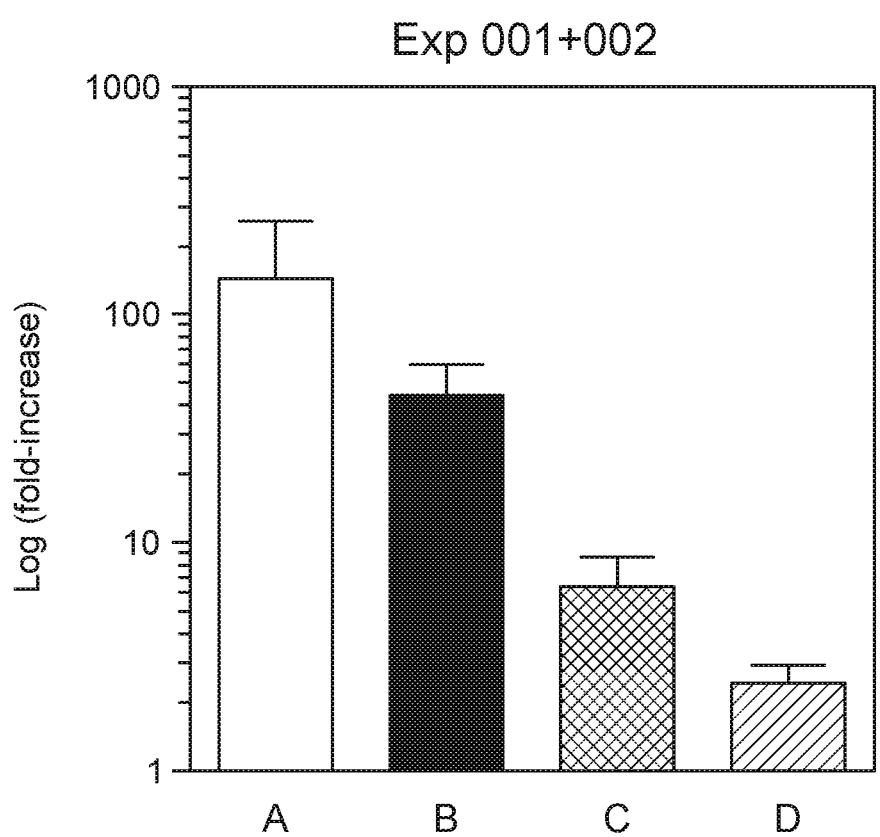
FIG. 6 shows an overlay of the results of the first and second duplicate of the results demonstrating the in vitro efficacy of compound 1 for inhibiting human norovirus compared to 2'-C-methylcytidine triphosphate and compound 2.

Example 5, below, demonstrates that compound 1 is more effective at inhibiting mouse norovirus than compound 2, or than 2'-C-methylcytidine triphosphate. A comparison with DMSO as a control is given for reference. The experiment was conducted in duplicate and the results are shown in FIG. 4 (first duplicate) and FIG. 5 (second duplicate). FIG. 6 shows an overlay of the results of the first and second duplicate of the experiment. As shown in FIGS. 4, 5 and 6, "A" is DMSO, "B" is Compound 2, "C" is 2'-C-methylcytidine triphosphate (2'CmeC TP) and "D" is Compound 1. FIGS. 4-6 demonstrate that the viral titer increased almost two orders of magnitude when treated with only DMSO or 2'CmeC TP. However, the viral titer increased less than one order of magnitude in the presence of compound 1.

Example 6 shows a comparison with compound 1 and other compounds of Formula II (Table 7) and analogs thereof. Without wishing to be bound by theory, compounds that are even slightly different from the structure of Formula I can have substantially reduced activity in vitro. For example, compound 7 has a hydroxy group in place of the aryl amine and has an has an $EC_{50}$ value >38 μM; compound 35 shows an analog of compound 1 lacking the aryl amine group, and has an $EC_{50}$ value >100 μM. Additionally, compound 11 has a cyano group in place of the aryl amide and has an $EC_{50}$ value >121 μM. Similarly, compounds 36 and 37 show methyl-substituted amines and have $EC_{50}$ values >100 μM. Additional comparisons will be understood by one of skill in the art.

Figure 7A:
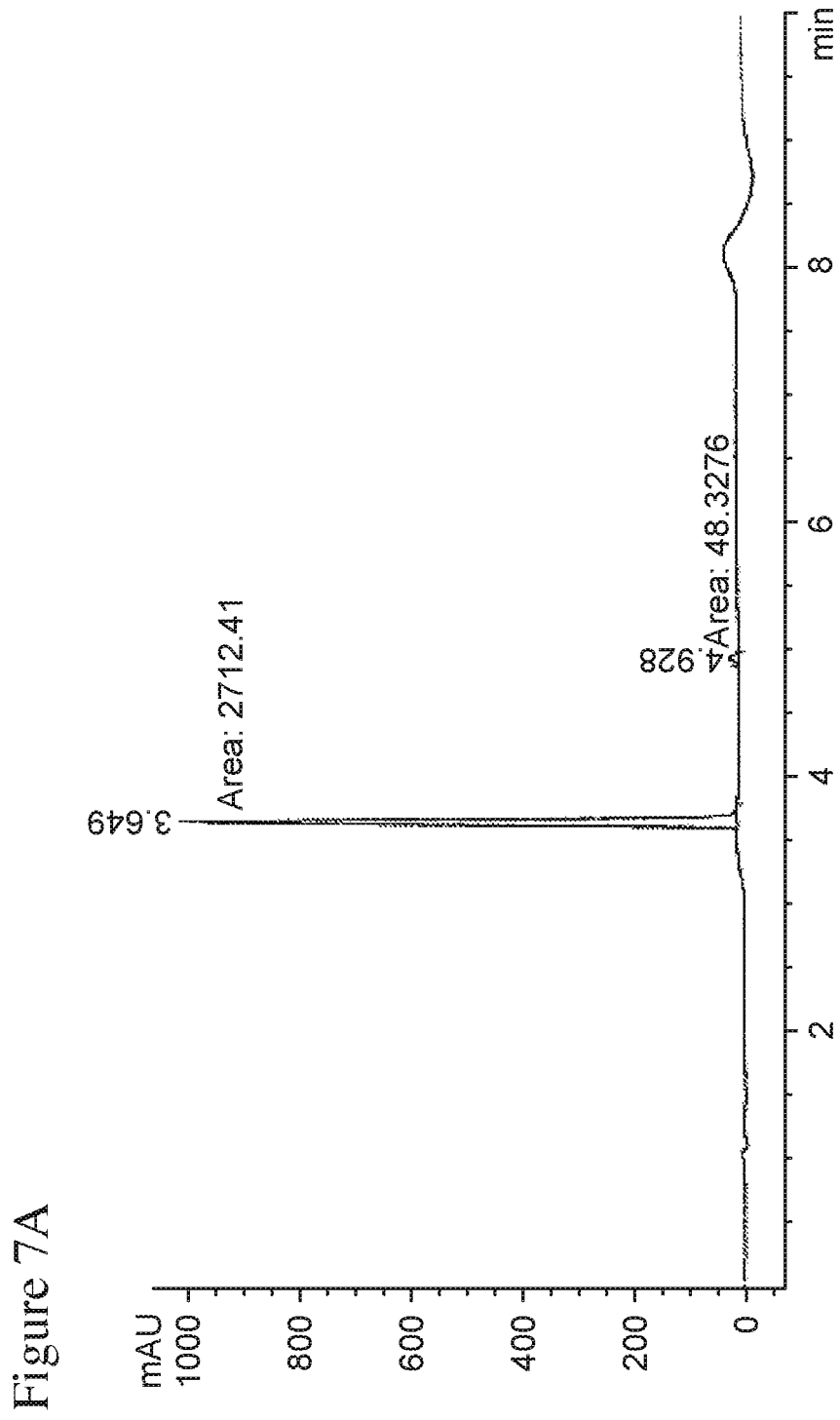
FIG. 7*a* shows an HPLC plot of compound 1.

FIG. 7a shows an HPLC plot of compound 1.

| Peak No. | Ret. Time | Type | Width (min) | Area (mAu*s) | Height (mAU) | Area % |
|---|---|---|---|---|---|---|
| 1 | 3.649 | MM | 0.0449 | 2712.41235 | 1007.2742 | 98.2495 |
| 2 | 4.928 | MM | 0.0511 | 48.32755 | 15.75879 | 1.7505 |

Without wishing to be bound by theory, peak no. 2 was identified as benzoic acid.

Figure 7B:
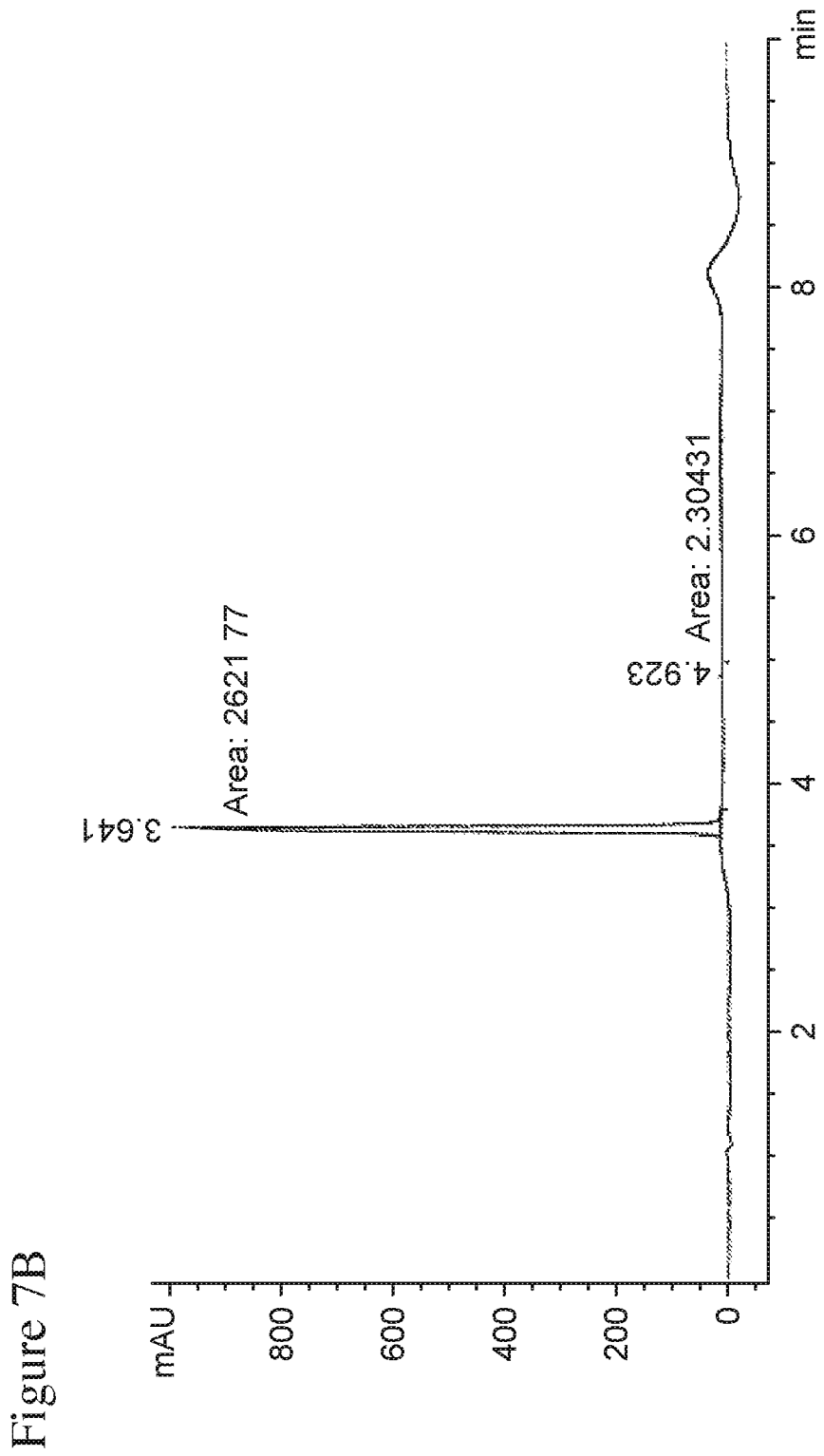
FIG. 7*b* shows an HPLC plot of compound 1 after slurrying 3 hours at room temperature.

FIG. 7b shows an HPLC plot of compound 1 after slurrying 3 hours at room temperature.

| Peak No. | Ret. Time | Type | Width (min) | Area (mAu*s) | Height (mAU) | Area % |
|---|---|---|---|---|---|---|
| 1 | 3.641 | MM | 0.0448 | 2621.76538 | 975.76003 | 99.9122 |
| 2 | 4.923 | MM | 0.0519 | 2.30431 | 0.739979 | 0.0878 |

Figure 7C:
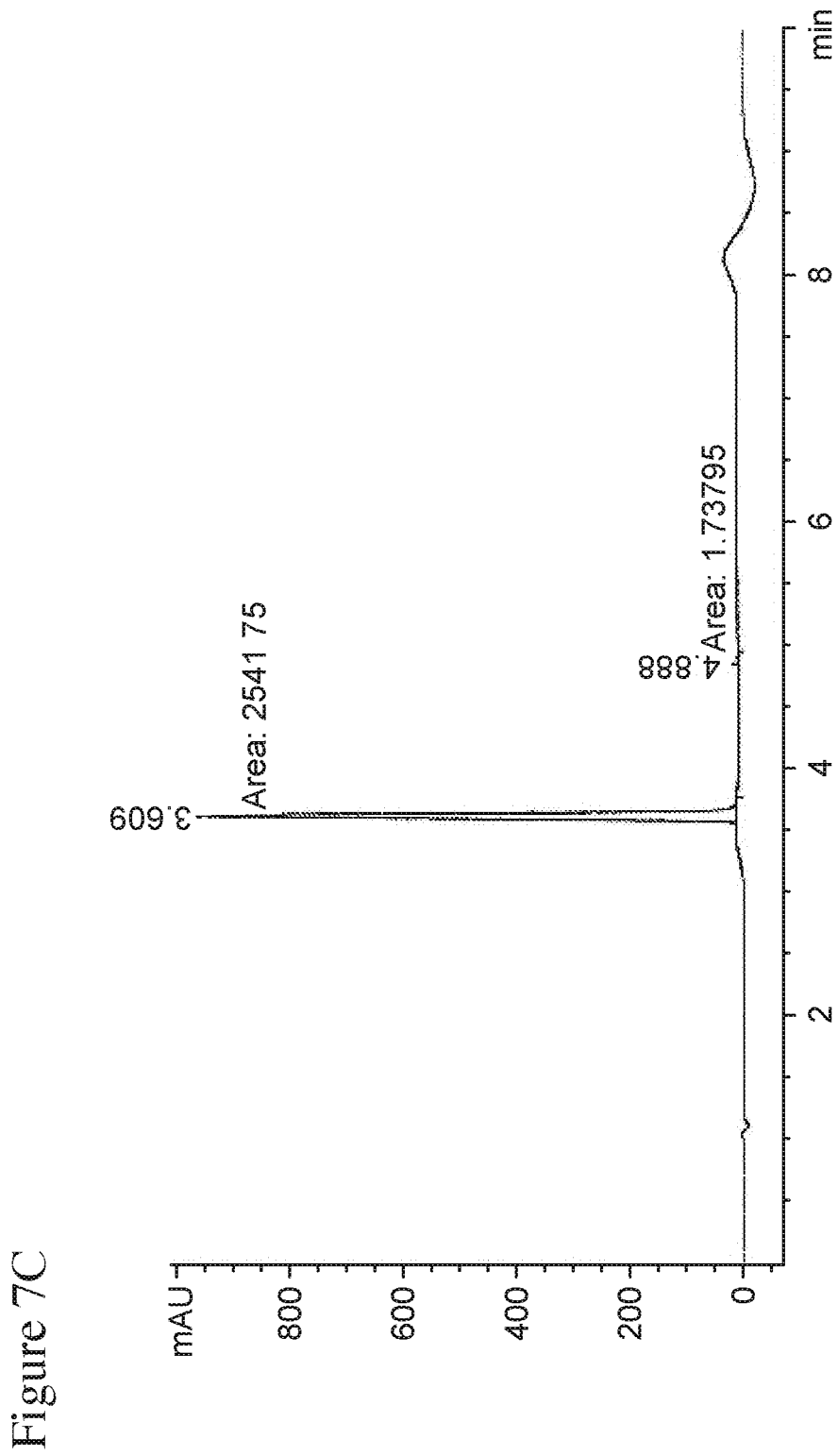
FIG. 7*c* shows an HPLC plot of compound 1 after slurrying 3 hours at 50° C.

FIG. 7c shows an HPLC plot of compound 1 after slurrying 3 hours at 50° C.

| Peak No. | Ret. Time | Type | Width (min) | Area (mAu*s) | Height (mAU) | Area % |
|---|---|---|---|---|---|---|
| 1 | 3.609 | MM | 0.0446 | 2541.75464 | 949.26025 | 99.9317 |
| 2 | 4.888 | MM | 0.473 | 1.737595 | 0.0612609 | 0.683 |

Figure 7D:
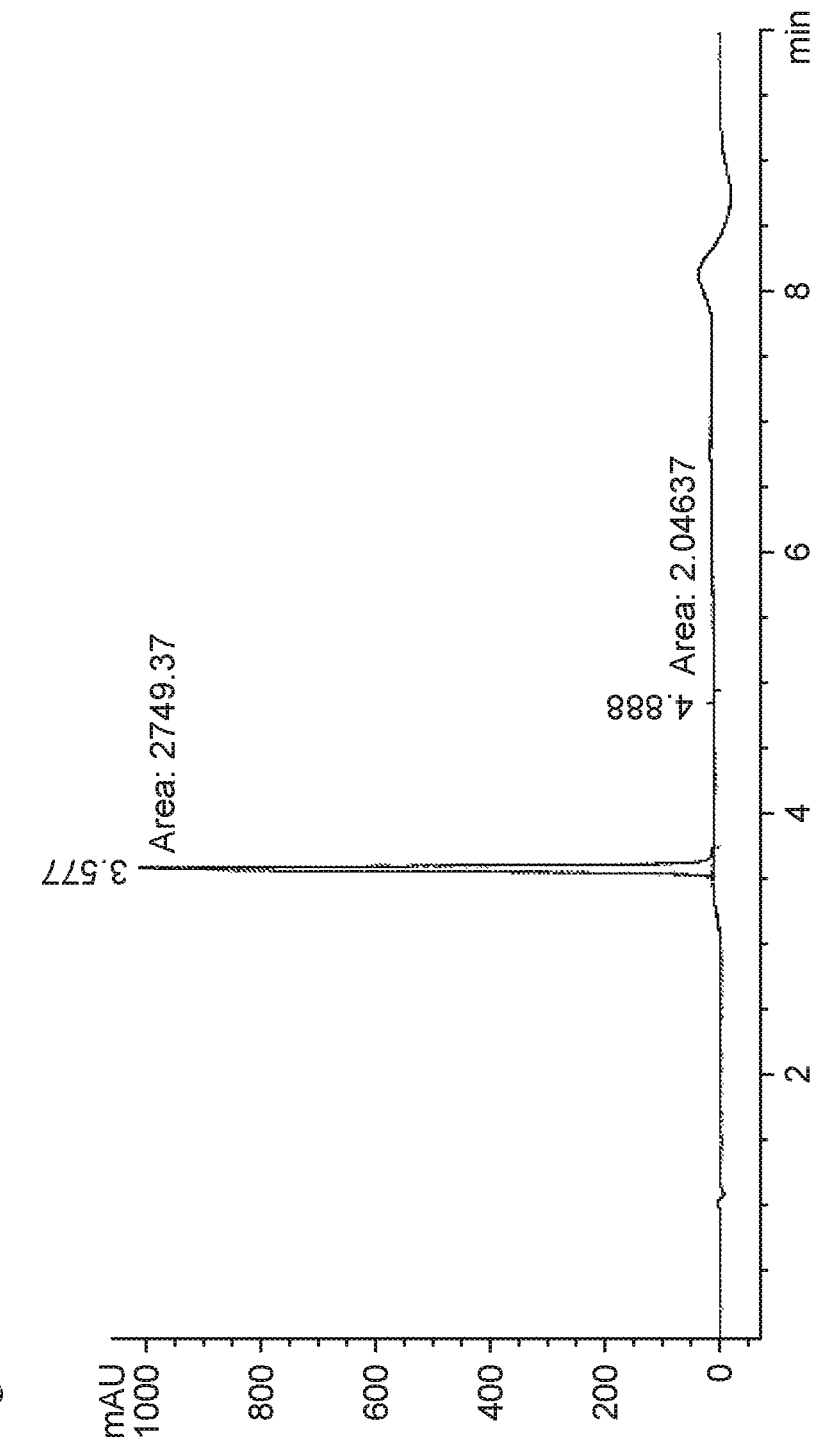
FIG. 7*d* shows an HPLC plot of compound 1 after slurrying 24 hours at about room temperature.

FIG. 7d shows an HPLC plot of compound 1 after slurrying 24 hours at about room temperature.

| Peak No. | Ret. Time | Type | Width (min) | Area (mAu*s) | Height (mAU) | Area % |
|---|---|---|---|---|---|---|
| 1 | 3.577 | MM | 0.0452 | 2749.37183 | 1013.14984 | 99.9256 |
| 2 | 4.888 | MM | 0.0500 | 2.04637 | 0.0682284 | 0.0744 |

Figure 8A:
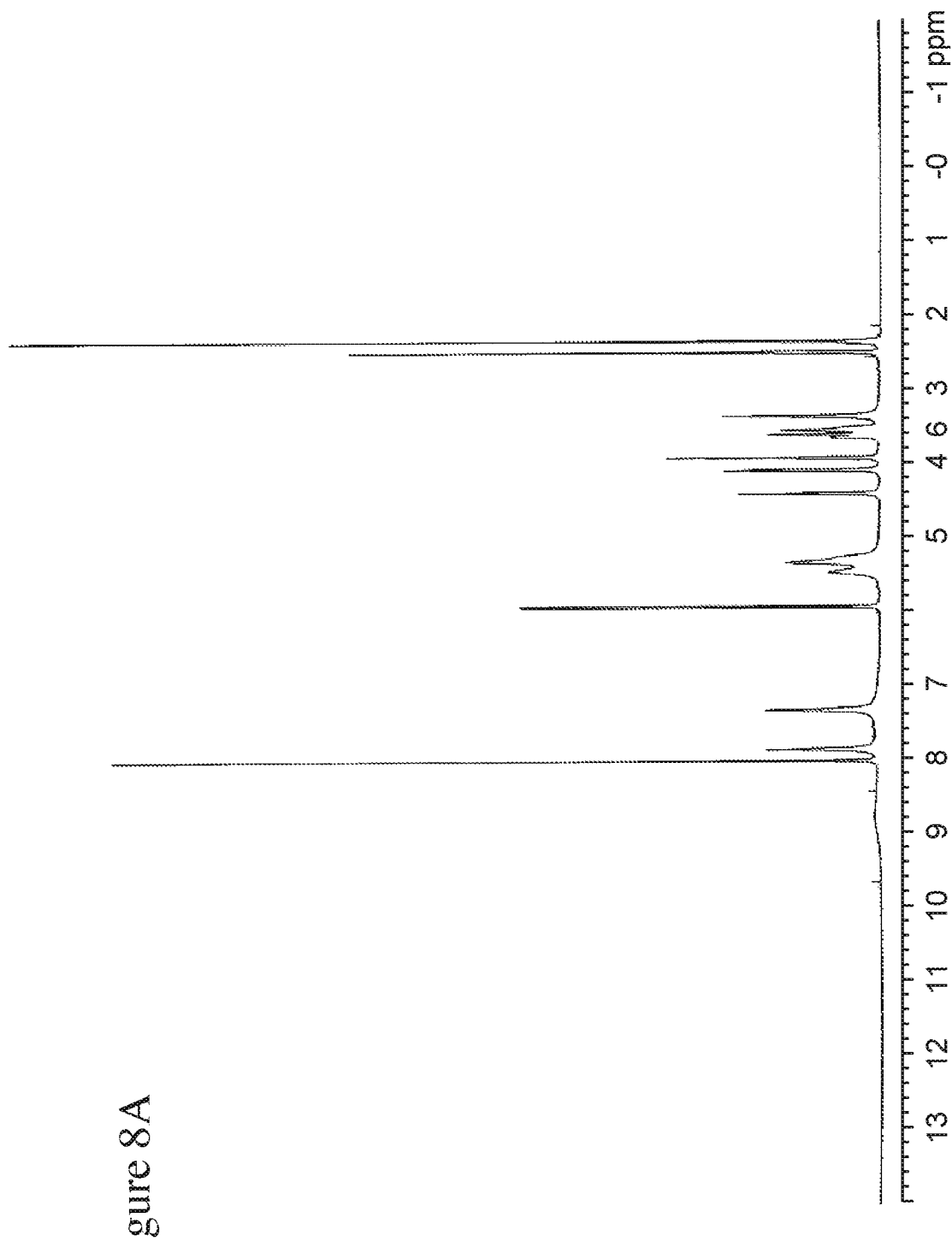
FIG. 8*a* shows a $^1$HNMR spectrum of compound 1 from about -2 to about 14 ppm.

FIG. 8a shows a $^{1}$HNMR spectrum of compound 1 from about −2 to about 14 ppm.

Figure 8B:
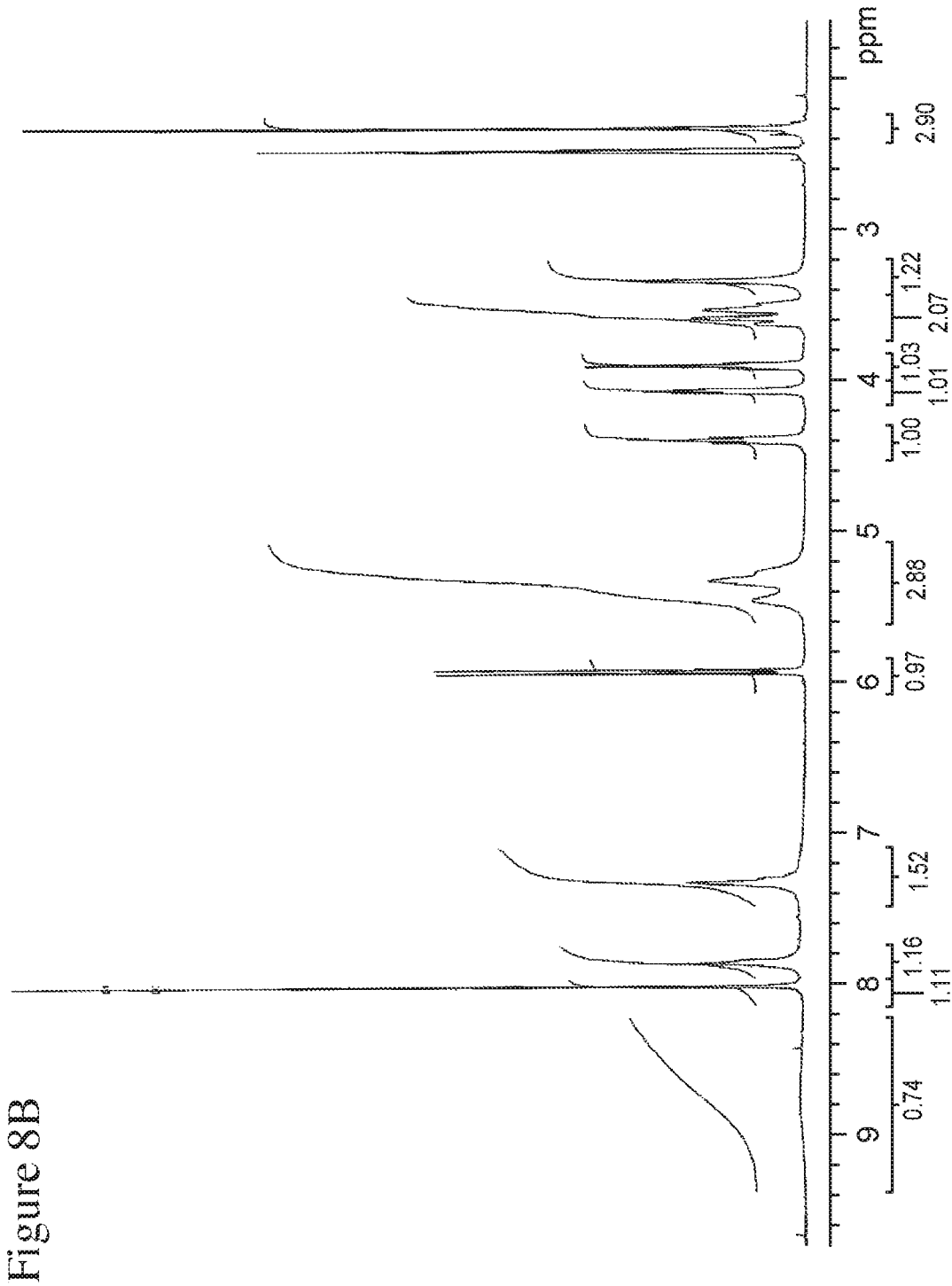
FIG. 8*b* shows a $^1$HNMR spectrum of compound 1 from about 2 to about 9 ppm.

FIG. 8b shows a $^{1}$HNMR spectrum of compound 1 from about 2 to about 9 ppm.

Figure 8C:
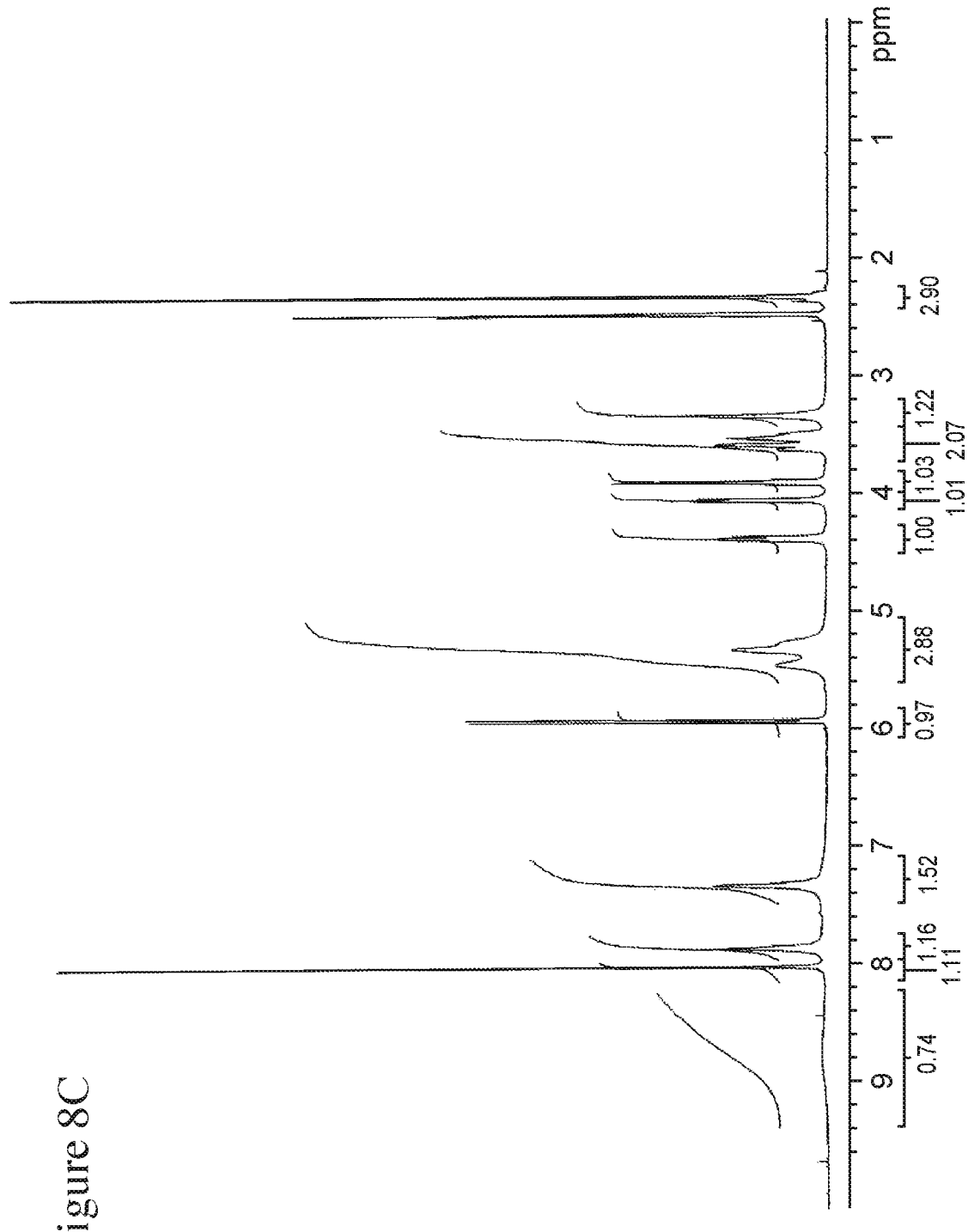
FIG. 8c shows a ¹HNMR spectrum of compound 1 from about 0 to about 9 ppm.

FIG. 8c shows a 1HNMR spectrum of compound 1 from about 0 to about 9 ppm.

EXAMPLES

General Procedures

The HPLC plots were recorded on a Zorbax Eclipse Plus C18 column (4.6×50 mm×1.8 μm). The first mobile phase was 97.5% water: 2.5% acetonitrile: 0.05% trifluoroacetic acid. The second mobile phase was 97.5% acetonitrile: 2.5% water: 0.05% trifluoroacetic acid.

$^{1}$HNMR were recorded at 500 MHz unless otherwise specified.

Example 1—Antiviral and Cytotoxicity Assays

Cells Culture and Virus Strains: Human foreskin fibroblast (HFF) cells were prepared from human foreskin tissue obtained from the University of Alabama at Birmingham tissue procurement facility with approval from its IRB. The tissue was incubated at 4° C. for 4 h in cell culture media consisting of minimum essential media (MEM) with Earle's salts supplemented with 10% fetal bovine serum (FBS) (Hyclone, Inc. Logan Utah), and standard concentrations of L-glutamine, fungizone, and vancomycin. Tissue was then placed in phosphate buffered saline (PBS), minced, rinsed to remove the red blood cells, and resuspended in trypsin/EDTA solution. The tissue suspension was incubated at 37° C. and gently agitated to disperse the cells, which were then collected by centrifugation. Cells were resuspended in 4 mL media and placed in a 25 cm$^2$ tissue culture flask and incubated at 37° C. in a humidified $CO_2$ incubator for 24 h. The media was then replaced with fresh media and the cell growth was monitored daily until a confluent cell monolayer was formed. The HFF cells were then expanded through serial passages in standard growth medium of MEM with Earl's salts supplemented with 10% FBS, L-glutamine, penicillin, and gentamycin. The cells were passaged routinely and used for assays at or below passage 10.

Akata cells latently infected with EBV were obtained from John Sixbey (Louisiana State University, Baton Rouge, La.). The GS strain of HHV-6A was obtained through the NIH AIDS Research and Reference Reagent Program. HSB-2 cells and BCBL-1 cells were obtained through the NIH AIDS Research and Reference Reagent Program, Division of AIDS, NIAID, NIH. Molt-3 cells were obtained from Scott Schmid at the Centers for Disease Control and Prevention, Atlanta, Ga. All lymphocyte cultures were maintained routinely in RPMI 1640 (Mediatech, Inc., Herndon, Va.) with 10% FBS, L-glutamine and antibiotics and passaged twice a week. Vero cells were obtained from American Type Culture Collection (ATCC, Manassas, Va.), and were maintained in standard growth medium of MEM with Earl's salts supplemented with 10% FBS, L-glutamine, penicillin, and streptomycin.

Influenza Virus:

Influenza A/New Caledonia/20/99 (H1N1) and A/Sydney/05/97 (H3N2) virus were provided by the Centers for Disease Control and Prevention (Atlanta, Ga.). The viruses were passaged in Madin-Darby canine kidney (MDCK) cells (American Type Culture Collection, Manassas, Va.) to create working stocks, which were used for the antiviral assays.

The E-377 and DM2.1 strains of HSV-1 as well as the MS and 13078 strains of HSV-2 were used. HSV-1 strain F was obtained from ATCC. The HCMV strains, AD169 and Merlin were obtained from the American Type Culture Collection (ATCC, Manassas, Va.) and C8805/37-1-1 and 759RD100 were a gift of Karen Biron. VZV, strain Ellen was obtained from the ATCC. The Z29 strain of HHV-6B was a gift of Scott Schmid at the Centers for Disease Control and Prevention, Atlanta Ga. HHV-8 was obtained as latently infected BCBL-1 cells through the NIH AIDS Research and Reference Reagent Program.

Antiviral Assays:

Each experiment that evaluated the antiviral activity of the compounds included both positive and negative control compounds to ensure the performance of each assay. Concurrent assessment of cytotoxicity was performed when possible at equivalent levels of compound exposure. Methods are presented following the tabulated data on effective concentrations giving 50% reductions in viral replication in vitro (EC50), concentrations producing 50% reduction in cell viability (CC50) and selectivity index (SI, calculated as CC50 divided by EC50). When sufficient material was available, multiple assays were performed for each compound evaluation to obtain statistical data.

Cytotoxicity Assays:

Every antiviral assay included a parallel cytotoxicity assay with the same cells used for each virus, the same cell number, the same drug concentrations, and the same incubation times to provide the same drug exposure. To ensure that the cytotoxicity of all compounds could be compared directly, a standard neutral red uptake cytotoxicity assay for all compounds in confluent HFF cells with a 7 d incubation period was performed.

Neutral Red-Uptake Cytotoxicity Assays:

Each compound was evaluated in a standard cytotoxicity assay by standard methods. Briefly, HFF cells were seeded into 96-well tissue culture plates at a $2.5 \times 10^4$ cells/well in standard tissue culture medium. After 24 h of incubation, medium was replaced with maintenance cell culture medium and compounds were added to the first row and then 5-fold serial dilutions were then used to generate a series of compound concentrations with a maximum of 300 µM. Assay plates were incubated for 7 d, and 100 µL of a 0.66 mg/mL neutral red solution in PBS was added to each well and the plates incubated for 1 h. The stain was then removed, the plates rinsed with PBS and the dye internalized by viable cells was solubilized in PBS supplemented with 50% ethanol and 1% glacial acetic acid. The optical density was then determined at 550 nm and CC50 values were interpolated from the experimental data.

For all plaque-reduction assays in HFF cells, neutral red cytotoxicity assays were performed on a parallel set of 6-well plates containing uninfected HFF cells that received the same compound concentrations as used for the antiviral assays. The cytotoxicity plates were removed from the incubator on the same day as each antiviral assay and the cell monolayer was stained for 6 h with 2 mL of a neutral red solution at a concentration of 0.165 mg/mL in PBS. The dye was then removed, residual dye rinsed from the cells with PBS, and cell monolayers were inspected visually for any signs of toxicity. Cytotoxicity assay with Vero cells was performed with drug concentrations ranging from 1 µM to 1 mM. The cell viability was determined using CellTiter 96® Aqueous One Solution Cell Proliferation Assay (Promega) according to manufacturer's instructions.

Cell Proliferation Assays:

The inhibition of HFF cell proliferation was used to refine estimates of cytotoxicity for some compounds and was performed according to a standard procedure used in the laboratory. Cells were seeded at a low density into six-well plates using $2.5 \times 10^4$ cells/well and standard culture medium. After 24 h, the medium was aspirated, and a range of compound solutions in the growth medium was prepared starting at 300 µM and added to duplicate wells. The plates were incubated for 72 h at 37° C., and the cells were then dislodged with trypsin and counted on a Beckman Coulter Counter. Compound concentrations that reduced cell proliferation by 50% were interpolated from experimental data.

Cytotoxicity in Lymphocyte Assays:

Cell viability in all assays with lymphocytes was assessed with the CellTiter-Glo Luminescent Cell Viability Assay (Promega). Briefly, assay plates were incubated at ambient temperature for 30 min then 50 µL of CellTiter-Glo reagent was added to each well and the plates were mixed for 2 min on an orbital shaker to lyse the cells. Plates were then incubated for an additional 10 min at ambient temperature and the luminescence was quantified on a luminometer. Standard methods were used to calculate drug concentrations that inhibited the proliferation of Akata, HSB-2, BCLB-1, or Molt-3 cells by 50% ($CC_{50}$).

TABLE 1

Activity of Compound 1 against mouse norovirus in RAW cells

| Compound | MNV Mean $EC_{50}$, µM | RAW Cells Mean $CC_{50}$, µM | SI |
|---|---|---|---|
| Compound 1 | 2.0 +/− 0.8 (n = 21) | 114.0 +/− 12.5 (n = 4) | 57.0 |
| Compound 1 | 2.1 (n = 33) | 114 | 54 |
| (2'-C-Methyl Cytidine) | 3.2 +/− 1.5 (n = 20) | 34.3 +/− 9.3 (n = 8) | 10.7 |

TABLE 2

Activity of Compound 1 against various DNA and RNA viruses

| Virus | $EC_{50}$ (µM) | $CC_{50}$ (µM) | SI | Cell line |
|---|---|---|---|---|
| DNA Viruses | | | | |
| AdV | >100 | >100 | ~1 | A549 |
| BKV | >60 | >60 | >1 | HFF |
| EBV | 7.15 | >60 | >8.4 | Akata |
| HCMV | >60 | >60 | ~01 | HFF |
| MCMV | >100 | >100 | ~1 | MEF |
| VZV | >60 | >60 | ~1 | HFF |
| HSV-2 | >60 | >60 | ~1 | HFF |
| HHV-6B | 39.66 | 44.71 | 1.13 | MOLT-3 |
| HHV-8 | >12.00 | 46.75 | <3.9 | BCBL-1 |
| VACV | 56.16 | >60 | ~1 | HFF |
| JCV | 0.46 | >60 | >130 | 293TT |
| MEV | >100 | >100 | ~1 | Vero76 |
| RNA Viruses | | | | |
| DENV-2 | >100 | >100 | ~1 | Vero76 |
| ENTV-71 | >100 | >100 | ~1 | Vero76 |
| HCV | 18.4 | >20 | >1.1 | Huh 7 |
| Flu (H1N1) | >100 | >100 | ~1 | MDCK |
| POV-3 | >100 | >100 | ~1 | Vero76 |
| RSV | 31 | 33 | 1.1 | MA-104 |
| SARS | 37 | >100 | >2.7 | Vero76 |
| RVFV | >100 | >100 | ~1 | Vero76 |
| VEEV | >100 | >100 | ~1 | Vero76 |
| YFV | >100 | >100 | ~1 | Vero |
| WNV | >100 | >100 | ~1 | Vero76 |

Mouse Norovirus (MNV) Assay:

RAW cells (Mouse Macrophage, ATCC TIV-71) were received from American Type Culture Collection (ATCC). The cells were incubated at 37° C. with 5% $CO_2$ in cell culture media consisting of Dulbecco's minimum essential media (DMEM) (ATCC) supplemented with 10% fetal bovine serum (FBS) (Hyclone, Inc., Logan Utah), 100 U/mL penicillin and 100 ug/mL streptomycin (Hyclone), 1% MEM NEAA (Gibco), 1% GlutaMAX (Gibco), and 1% HEPES (Hyclone). The mouse norovirus isolate used in this assay was isolated from a wild mouse, cell-culture adapted, plaque purified, and genetic sequence confirmed by Chimerix, Inc.

100 µL of serial dilutions of test compounds in DMEM were added to Costar 96-well tissue culture-treated plates. 100 µL of cell suspension containing 50,000 RAW cells/well and MNV (MOI=0.0005) were added to the compound dilutions in the 96-well plate, and incubated at 37° C. with 5% $CO_2$ for 2 days. Each assay plate included uninfected cell controls and untreated virus control wells. After 2 days of incubation, the untreated virus control wells showed 100% CPE. After 2 days of incubation, 40 µL of Cell Titer 96® Aqueous MTS Reagent (Promega, G111) was added as directed by manufacturer to the 200 µL media in each well and incubated at 37° C. until the untreated-cell controls developed a 490 nm absorbance between 1.1 and 1.8. The final absorbance readings were read using a BioTek Synergy 2, and Gen 5 software (BioTek Instruments, Inc.) was used to calculate the concentration that protected MNV-infected RAW cells by 50% compared to uninfected cell controls (EC50).

Human Norovirus Assays:

Antiviral activity against a human Norovirus (NoV) was assessed in a 3-day assay using the stably-expressing human Norovirus replicon cell line, HG23 (genogroup I, genomic length; parental cell line, HuH7) (Chang, et al., 2006, Virol. 353:463) maintained as sub-confluent cultures on 96-well plates. Typically, 4 doses (10-fold or 3-fold steps), in triplicate are used. Antiviral activity was determined by blot hybridization analysis of intracellular NoV RNA (normalized to the level of cellular β-actin RNA in each culture sample). Cytotoxicity was assessed by neutral red dye uptake in cultures maintained in parallel plates (Korba and Gerin, 1992, Antivir. Res. 19:55).

$EC_{50}$, and $CC_{50}$ values are calculated by linear regression analysis (MS EXCEL®, QuattroPro®) using data combined from all treated cultures (Korba & Gerin, 1992, Antivir. Res. 19:55; Okuse, et al., 2005, Antivir. Res. 65:23). Standard deviations for $EC_{50}$ and $EC_{90}$ values were calculated from the standard errors generated by the regression analyses. $EC_{50}$ and $EC_{90}$ are drug concentrations at which a 2-fold, or a 10-fold depression of intracellular NoV RNA (relative to the average levels in untreated cultures), respectively, was observed. $CC_{50}$ is the drug concentration at which a 2-fold lower level of neutral red dye uptake (relative to the average levels in untreated cultures) is observed. The Selectivity index (S.I.) was calculated as $CC_{50}/EC_{50}$. Recombinant human interferon 2b (PBL laboratories, Inc.) is used as an assay control.

BKV $EC_{50}$ in VERO Cells:

Costar 96-well tissue culture plates were seeded with 10,000 Vero cells/well in DMEM containing 2% Hyclone Standard Fetal Bovine Serum (FBS, Cat SH30088.03) and 1% Hyclone Penicillin and Streptomycin. Outer wells were not used to minimize the edge-effect produced by extended incubations. Cells were inoculated with 115 BKV DNA copies/cell (ATCC, Gardner strain). Serial dilutions of test compounds were added to the cells and plates were incubated for 10 days at 37° C. in 5% $CO_2$. After the 10-day incubation, 50 µL supernatant was mixed with 50 µL 2× lysis buffer that provided a final concentration 0.5 mg/mL protease K, 50 mM KCl, 10 mM Tris-Cl pH 8.0, 2.5 mM MgCl2, 0.45% IGEPAL, and 0.45% Tween-20 dissolved in DEPC-treated water. Each plate was incubated for 2 hours at 55° C. Supernatant BKV DNA was measured by quantitative polymerase chain reaction (qPCR) using forward and reverse BKV PCR primers, and a FAM-labeled probe. Absolute quantitation of viral copy number was performed using a standard curve with dilutions of a BKV DNA amplicon containing sequences homologous to the amplified fragment. The following qPCR amplification conditions were used: 1 cycle at 95° C. for 10 minutes, followed by 45 cycles of 95° C. for 15 seconds and 60° C. for 60 seconds. The qPCR reactions were performed using an Applied Biosystems 7500 real Time PCR System. Gen 5 software (BioTek Instruments, Inc.) was used to calculate the concentration which inhibited the viral DNA levels of BKV-infected Vero cells by 50% (EC50).

Plaque-Reduction Assays for HSV-1, HSV-2, VZV and HCMV:

Monolayers of HFF cells were prepared in six-well plates and incubated at 37° C. for 2 d to allow the cells to reach confluency. Media was then aspirated from the wells and 0.2 mL of virus was added to each of three wells to yield 20-30 plaques in each well. The virus was allowed to adsorb to the cells for 1 h and the plates were rocked gently every 15 min to redistribute the media. Compounds were diluted in maintenance cell culture media consisting of MEM with Earl's salts supplemented with 2% FBS, L-glutamine, penicillin, and gentamycin. Solutions ranging from 300 µM to 0.1 µM were added to duplicate wells and the plates were incubated for various times, depending on the virus used. The plaque-reduction assay with HSV-1 strain F was performed in a similar manner but with Vero cells infected one day after plating. Final FBS concentration in this assay was 5%. For HSV-1 and -2, the monolayers were stained with 1% crystal violet in 20% methanol and the unbound dye removed by washing with $dH_2O$. For assays with HCMV and VZV, the cell monolayer was stained with 1% Neutral Red solution for 4 h then the stain was aspirated and the cells were washed with PBS. For all assays, plaques were enumerated using a stereomicroscope and the concentration of compound that reduced plaque formation by 50% (EC50) was interpolated from the experimental data.

Plaque-Reduction Assays for MCMV:

Mouse embryo fibroblast cells were prepared from mouse embryos using a procedure similar to that outlined above for HFF cells and suspended in tissue culture media as described above and seeded into 12 well plates and incubated at 37° C. for 24 h. The medium was aspirated and the cell monolayers were infected with the Smith strain of MCMV in a final volume of 0.2 mL in each of triplicate wells. The infected cells were then incubated at 37° C. for 1 h and the plates were rocked occasionally to ensure that the media covered the entire monolayer. Compounds were serially diluted 1:5 in tissue maintenance cell culture media described above and the solutions were added to the infected monolayers. Infected monolayers were incubated for 7 d and then stained with 2 mL of a 1% Neutral Red solution as described above. Plaques were enumerated and $EC_{50}$ values were interpolated from the experimental data by standard methods.

DNA Quantitation Assays for EBV and HHV-6B:

Assays for EBV were performed in Akata cells that were induced to undergo a lytic infection with 50 µg/mL of a goat anti-human IgG antibody by standard methods. Experimental compounds were diluted in round bottom 96-well plates to yield concentrations ranging from 20 to 0.016 µM. Akata cells were added to the plates at a concentration of $4 \times 10^4$ cells per well and incubated for 72 h. For HHV-6, compounds were serially diluted in 96-well plates then $1 \times 10^4$ uninfected HSB-2 or Molt-3 cells were added to each well. Infection was initiated by adding HHV-6A infected HSB-2 cells, or HHV-6B infected Molt-3 cells, at a ratio of approximately 1 infected cell for every 10 uninfected HSB-2 cells or Molt-3 cells respectively and incubated for 7 d at 37° C.

For all assays, 100 μL of denaturation buffer (1.2M NaOH, 4.5M 80 NaCl) was added to each well to denature the DNA and a 50 μL aliquot was aspirated through an Immobilon nylon membrane (Millipore, Bedford, Mass.) using a Biodot apparatus (Bio-Rad, Hercules, Calif.). The membranes were then allowed to dry before equilibration in DIG Easy Hyb (Roche Diagnostics, Indianapolis, Ind.) at 56° C. for 30 min. Specific digoxigenin (DIG)-labeled probes were prepared for each virus according to the manufacturer's protocol (Roche Diagnostics). For EBV, primers 5'-CCC AGG AGT CCC AGT AGT CA-3' (SEQ ID No. 1) and 5'-CAG TTC CTC GCC TTA GGT TG-3' (SEQ ID No. 2) amplified a fragment corresponding to coordinates 96802-97234 in EBV genome (AJ507799). A specific HHV-6 DIG labeled probe was prepared using primers 5'-CCT TGA TCA TTC GAC CGT TT-3' (SEQ ID No. 3) and 5'-TGG GAT TGG GAT TAG AGC TG-3' (SEQ ID No. 4) to amplify a segment of ORF2 (coordinates 37820-38418 in X83413). Membranes with EBV DNA were hybridized overnight at 56° C. followed by sequential washes in 0.2×SSC with 0.1% SDS and 0.1×SSC with 0.1% SDS at the same temperature. For HHV-6A and HHV-6B blots, the probe was allowed to hybridize overnight at 42° C. and the blots were rinsed at the same temperature with 0.2×SSC with 0.1% SDS and 0.1× SSC with 0.1% SDS. Detection of specifically bound DIG probe was performed with anti-DIG antibody using the manufacturer's protocol (Roche Diagnostics). An image of the photographic film was captured and quantified with QuantityOne software (Bio-Rad) and compound concentrations sufficient to reduce the accumulation of viral DNA by 50% (EC50), were interpolated from the experimental data.

DNA Quantitation Assays for HHV-8:

Test compounds were diluted in duplicate wells of a 96-well plate with the highest final concentration of 20 μM. BCBL-1 cells were induced to undergo a lytic infection by the addition of phorbol 12-myristate 13-acetate (Promega, Madison Wis.) at a final concentration of 100 ng/mL and $2 \times 10^4$ cells were added to each well in the plate. Cells were incubated for 7 d at 37° C. in a humidified $CO_2$ incubator then total DNA was prepared with a Wizard SV 96 well purification kit (Promega). Viral DNA was quantified by real time PCR using forward primer 5'-TTC CCC AGA TAC ACG ACA GAA TC-3', (SEQ ID No. 5) reverse primer 5'-CGG AGC GCA GGC TAC CT-3', (SEQ ID No. 6) and probe 5'-(FAM) CCT ACG TGT TCG TCG AC (TAMRA)-3' (SEQ ID No. 7). Plasmid pMP218 containing a DNA sequences corresponding to nucleotides 14120-14182 (AF148805.2) was used to provide absolute quantification of viral DNA. Compound concentrations sufficient to reduce genome copy number by 50% were calculated from experimental data.

Cell-Based Assays for Flu:

For dose-response curves, individual drugs were added to MDCK cells in 96-well microplates ($8 \times 10^4$ cells/well) using three wells for each concentration used. The compounds were added at the following concentrations: oseltamivir carboxylate at 0, 0.000032, 0.0001, 0.00032, 0.001, 0.0032, 0.01, 0.032, 0.1, 1.0, 10.0 and 100 μg/mL; amantadine and ribavirin at 0, 0.001, 0.0032, 0.01, 0.032, 0.1, 0.32, 1, 3.2, 10, 32 and 100 μg/mL. Untreated wells of infected cells (virus controls) and uninfected cells (cell controls) were included on each test plate. At three days post-infection, the virus control wells exhibited 100% cytopathology. The extent of viral cytopathology in each well was determined microscopically by inspection and by staining with neutral red (NR). Briefly, the cells were stained with 0.011% NR diluted in MEM to determine cell viability. Two hours later the plates were processed for quantification of NR uptake into viable cells. The amount of NR taken up by cells was determined spectrophotometrically.

qPCR Assays for BKV and JCV:

Primary assays for BK virus were performed in 96-well plates containing monolayers of HFF cells. Compound dilutions were prepared in plates containing cells which were subsequently infected at with the Gardner strain of BK virus. After a 7 d incubation, total DNA was prepared with a Wizard SV 96 well purification kit and genome copy number was quantified by real time PCR using the primers 5'-AGT GGA TGG GCA GCC TAT GTA-3' (SEQ ID No. 8), 5'-TCA TAT CTG GGT CCC CTG GA-3' (SEQ ID No. 9) and probe 5'-6-FAM AGG TAG AAG AGG TTA GGG TGT TTG ATG GCA CAG TAMRA-3' (SEQ ID No. 10). Plasmid pMP526 served as the DNA standard for quantitation purposes. Compounds that were positive in this assay were confirmed in a similar assay in 96-well plates with the compounds added 1 h following infection to identify compounds that inhibit early stages of replication including adsorption and penetration. Genome copy number was determined by methods described above.

Primary evaluation of compounds against JC virus were also performed by methods similar to those for BK virus primary assays but were done in 293TT cells and utilized the 1-4 strain of JCV in 293TT cells. Viral DNA was quantified using primers 5'-CTG GTC ATG TGG ATG CTG TCA-3' (SEQ ID No. 11) and 5'-GCC AGC AGG CTG TTG ATA CTG-3' (SEQ ID No. 12) and probe 5'-6-FAM-CCC TTT GTT TGG CTG CT-TAMRA-3' (SEQ ID No. 13) together with the plasmid pMP508 to provide a standard curve for absolute quantification. Secondary assays against JCV were performed in COS7 cells by methods similar to those for BK virus to identify compounds that inhibited adsorption or penetration of the virus.

Hepatitis C Virus Assay:

Luciferase reporter (Replicon)/CytoTox-1 (Toxicity). Compounds were screened for anti-HCV activity using a luciferase (Luc) reporter gene endpoint in the HCV primary assay. The Luc reporter was used as an indirect measure of HCV replication as its activity was directly proportional to HCV RNA levels. Assessment of cytotoxicity is conducted in parallel. Drug stocks were prepared in DMSO unless otherwise specified and are diluted with tissue culture medium to the desired high-test concentration. For each assay, the compounds were then further diluted in tissue culture medium as required. After incubation, the cells were processed to derive, where applicable, EC50 and EC90 (compound concentration reducing replicon replication by 50% and 90% respectively). CC50 (concentration decreasing cell viability by 50%) and SI50 (CC50/EC50) values were determined and reported. Anti-HCV activity was assessed with the replicon (genotype 1b or 2a) or HCVcc virus-derived Luc activity as readout; whereas the cytotoxic concentrations of drug reducing cell numbers was assessed by the CytoTox-1 cell proliferation assay (Promega, Madison, Wis.) according to manufacturer's protocol. Recombinant interferon alpha was used as the positive control drug to validate assay performance.

Assays for Influenza, Respiratory Syncytial Virus (RSV), and SARS CoV:

Principal Viruses and Cells used were Influenza Strain A/California/7/2009 (H1N1) in MDCK cells, Respiratory syncytial virus Strain A-2 in Hep2 cells and SARS CoV Strain Toronto-2 in VeroE6 cells.

Assays for Influenza virus, RSV, and SARS CoV were Cytopathic effect/Toxicity-based assay using CellTiter-Glo. The antiviral cytoprotection assays examined the effects of compounds at designated dose-response concentrations in specific cell types to test the efficacy of the compounds in preventing the virus-induced cytopathic effect. Ribavirin was included as a positive control drug for influenza and RSV, while calpain IV inhibitor was used for SARS antiviral assays. Subconfluent cultures of cells were plated into 96-well plates for the analysis of cell viability (cytotoxicity) and antiviral activity (CPE). For the standard assay, drugs were added to the cells 24 hours later. The CPE wells also received 100 tissue culture infectious doses (100 TCID50s) of titered virus. 72 hours later the cell viability was determined.

Measurement of viral-induced CPE was based on quantitation of ATP, an indicator of metabolically active cells. The CPE assay employed a commercially available CellTiter-Glo™ Luminescent Cell Viability Kit (Promega, Madison, Wis.), and was a reliable method for determining cytotoxicity and cell proliferation in culture. The procedure involved adding the single reagent (CellTiter-Glo™ Reagent) directly to previously cultured, subconfluent cells in media. This induced cell lysis and the production of a bioluminescent signal (half-life greater than 5 hours, depending on the cell type) that was proportional to the amount of ATP present (which is a biomarker for viability).

Assays for Dengue (DENV), West Nile Virus (WNV), Yellow Fever Virus (YFV), Rift Valley Fever Virus (RVFV), Venezuelan Equine Encephalitis Virus (VEEV):

Primary cytopathic effect (CPE) reduction assay. Four-concentration CPE inhibition assays were performed. Confluent or near-confluent cell culture monolayers in 96-well disposable microplates were prepared. Cells were maintained in MEM or DMEM supplemented with FBS as required for each cell line. For antiviral assays the same medium was used but with FBS reduced to 2% or less and supplemented with 50 µg/mL gentamicin. The test compound was prepared at four log 10 final concentrations, usually 0.1, 1.0, 10, and 100 µg/mL or M. The virus control and cell control wells were on every microplate. In parallel, a known active drug is tested as a positive control drug using the same method as was applied for test compounds. The positive control was tested with each test run. The assay was set up by first removing growth media from the 96-well plates of cells. Then the test compound was applied in 0.1 mL volume to wells at 2× concentration. Virus, normally at <100 50% cell culture infectious doses (CCID50) in 0.1 mL volume, was placed in those wells designated for virus infection. Medium devoid of virus was placed in toxicity control wells and cell control wells. Virus control wells were treated similarly with virus. Plates were incubated at 37° C. with 5% $CO_2$ until maximum CPE is observed in virus control wells. The plates were then stained with 0.011% neutral red for approximately two hours at 37° C. in a 5% $CO_2$ incubator. The neutral red medium was removed by complete aspiration, and the cells may be rinsed 1× with phosphate buffered solution (PBS) to remove residual dye. The PBS was completely removed and the incorporated neutral red is eluted with 50% Sorensen's citrate buffer/50% ethanol (pH 4.2) for at least 30 minutes. Neutral red dye penetrates into living cells, thus, the more intense the red color, the larger the number of viable cells present in the wells. The dye content in each well was quantified using a 96-well spectrophotometer at 540-nm wavelength. The dye content in each set of wells was converted to a percentage of dye present in untreated control wells using a Microsoft Excel computer-based spreadsheet. The 50% effective (EC50) concentrations and 50% cytotoxic (CC50) concentrations were then calculated by linear regression analysis. The quotient of CC50 divided by EC50 gives the selectivity index (SI) value.

Assays for Adenovirus (AdV), Measles (MEV), Poliovirus (POV) and Enterovirus (ENTV):

The primary screen was a cytopathic effect (CPE) reduction assay. Briefly, 96-well cultures of cells were infected with virus in the presence of test compounds and incubated for 4-7 days (depending on the specific virus/cells). Each virus was pre-titered such that control wells exhibited approximately 95% loss of cell viability due to virus replication. Therefore, antiviral effect, or cytoprotection, was observed when compounds prevent virus replication. Each assay plate contained cell control wells (cells only), virus control wells (cells plus virus), compound toxicity control wells (cells plus compound only), compound colorimetric control wells (compound only, no cells or virus), as well as experimental wells (compound plus cells plus virus). Cytoprotection and compound cytotoxicity were assessed by MTS (CellTiter®96 Reagent, Promega, Madison Wis.) dye reduction. The percent reduction in viral CPE (antiviral activity) and percent cell viability (cytotoxicity) were determined and reported.

Assays for Vaccinia Virus (VACV):

The primary assay was a cytopathic effect (CPE) reduction assay. Low passage (3-10) HFF cells were trypsinized, counted, and seeded into 96 well tissue culture plates in 0.1 mL of MEM supplemented with 10% FBS. The cells were then incubated for 24 h at 37° C. The media was then removed and 100 µL of MEM containing 2% FBS was added to all but the first row. In the first row, 125 µL of media containing the experimental drug (i.e., Compound 1) was added in triplicate wells. Media alone was added to both cell and virus control wells. The drug in the first row of wells was then diluted serially 1:5 throughout the remaining wells. The plates were then incubated for 60 minutes and 100 µL of a virus suspension was added to each well, excluding cell control wells which received 100 µL of MEM. The plates were then incubated at 37° C. in a $CO_2$ incubator for three days for VACV. After the incubation period, media was aspirated and the cells stained with crystal violet in formalin for 4 h. The stain was then removed and the plates were rinsed until all excess stain was removed. The plates were allowed to dry for 24 h and the amount of CPE in each row determined using a BioTek Multiplate Autoreader. $EC_{50}$ and $CC_{50}$ values were determined by comparing drug treated and untreated cells using a computer program.

Example 2—Determination of Efficacy of Compound 1 Against Murine Norovirus in Mice Methodology Two studies (Study No. 1 and Study No. 2) examined the ability of Compound 1 to protect mice from or to reduce murine norovirus infection:

Study No. 1 evaluated the efficacy of twice-daily dosing of Compound 1 over a range of 30 mg/kg to 300 mg/kg, initiated prior to infection of mice with $10^6$ plaque-forming units (PFU) of murine norovirus (MNV) CR3. A control group of mice treated with vehicle was also included. All doses were started 2 days (39 hours) prior to infection. Study groups are shown in Table 3.

Compound was delivered twice daily at indicated doses via oral gavage. A control group of mice treated with vehicle only was also included. Mice were infected with murine norovirus by pipetting virus into mouth 2 days after the first dose. The mice used were ~20 gram, 8-12 week old female BALB/c mice in groups of 5 (the study groups are shown in Table 3). Mice were housed on metal grates and combined fecal output was collected every 24 hours. Tissues (distal ileum and cecum) and individual fecal pellets were harvested on day 3 post inoculation. All samples were titered by plaque assay.

For both studies, compound was delivered via oral gavage at the indicated doses and times prior to infection. Mice were infected with murine norovirus $CR_3$ by pipetting virus into mouth 3 hours after the first day 0 dose of Compound 1 was given. Following infection, compound was administered twice daily through day 3 post-infection.

The mice used were ~20 gram, 8-12 week old female BALB/c mice in groups of 5. Mice were housed on metal grates and combined fecal output was collected every 24 hours, starting at day −1. Tissues (~1 cm of distal ileum and cecum) and individual fecal pellets were harvested on day 3 post-infection and weighed. All samples were titered by plaque assay (qRT-PCR as back-up when titers are too low); titers were normalized to gram of tissue or feces. On day 3, duplicate samples of tissue (~1 cm of distal ileum and cecum) were collected, rinsed in PBS, and snap frozen; serum and a duplicate feces sample were also collected on day 3 and snap frozen; this set of sample was submitted for MS analysis to assess drug bioavailability.

Results

Results of Study No. 1 show that twice-daily Compound 1 treatment, administered starting 2 days prior to infection, was effective in reducing the titer of murine norovirus in both tissue and feces, with a greater reduction in virus titer observed with increasing drug concentration as shown in

TABLE 3

Study No. 1: Study Design for Proof-of-Concept Efficacy Evaluation of Compound 1 against Murine Norovirus Infection in Mice

| Group[1] (n = 25) | Test Article | Dosage and Delivery | Readouts after norovirus challenge |
|---|---|---|---|
| 1 | Compound 1 | 30 mg/kg/day (BID) orally starting on day −2[2] | Pooled fecal samples shed over 24 hour period, analyzed for viral content via plaque assay |
| 2 | Compound 1 | 100 mg/kg/day (BID) orally starting on day −2 | Tissue titers and individual fecal titers determined 3 days post inoculation via plaque assay |
| 3 | Compound 1 | 300 mg/kg/day (BID) orally starting day −2 | |
| 4 | Oral vehicle | N/A | |

[1]5 mice per group
[2]Compound was administered 51, 39, 27, 15 and 3 hours before infection, and then every 12 hours thereafter
Note:
30 mg/kg/day(15 mg/kg/dose, bid); 100 mg/kg/day (50 mg/kg/dose, bid); 300 mg/kg/dose, (150 mg/kg/dose, bid). Start oral gave of drug 2 days before injection; BID oral gavage drug.

Study No. 2 evaluated the efficacy of twice-daily dosing of Compound 1 at 150 mg/kg or 300 mg/kg, initiated prior to infection of mice with $10^4$ pfu of MNV CR3. A control group of mice treated with vehicle was also included. The 150 mg/kg dose was started either 2 days (39 hours) prior to inoculation, 1 day (15 hours) prior to inoculation, or on the day of (3 hours prior to) inoculation; the 300 mg/kg dose was started 2 days (39 hours) prior to infection. Study groups are shown in Table 4.

This study tested the ability of Compound 1 to protect mice from or reduce murine norovirus infection. Compound was delivered twice daily at indicated doses via oral gavage starting 2 days prior to inoculation, 1 day prior to inoculation or at time of inoculation. A control group of mice treated with vehicle only was also included. Mice were infected with $10^4$ PFU of murine norovirus by pipetting virus into mouth 3 hours after the Day 0 dose. The mice used were ~20 gram, 8-12 week old female BALB/c mice in groups of 5 (the study groups are shown in Table 4). All samples were titered by plaque assay.

TABLE 4

Study No. 2: Study Design for Efficacy Evaluation of Compound 1 against Murine Norovirus Infection in Mice

| Group[1] (n = 25) | Test Article | Dosage and Delivery | Readouts after norovirus challenge |
|---|---|---|---|
| 1 | Compound 1 | 150 mg/kg twice daily orally starting on day −2[2] | Pooled fecal samples shed over 24 hour period, analyzed for viral content via plaque assay |
| 2 | Compound 1 | 150 mg/kg twice daily orally starting on day −1[3] | Tissue titers and individual fecal titers determined 3 days post inoculation via plaque assay |
| 3 | Compound 1 | 150 mg/kg twice daily orally starting day 0[4] | |
| 4 | Compound 1 | 300 mg/kg twice daily orally starting day −2[2] | |
| 5 | Oral vehicle | N/A | |

[1]5 mice per group
[2]Compound was administered 51, 39, 27, 15 and 3 hours before infection, and then every 12 hours thereafter
[3]Compound was administered 27, 15, and 3 hours prior to infection, and then every 12 hours thereafter
[4]Compound was administered 3 hours prior to infection, and then every 12 hours thereafter
Note:
150 mg/kg twice daily = 300 mg/kg total daily dose; 300 mg/kg twice daily = 600 mg/kg daily dose. Oragl gave drug for 2 days or 1 day or day 0 before infection. Infect mice with $10^4$ PFU MNV via oral gavage on day 0. Twice daily oral gavage every 12 hours.

Figure 1B:
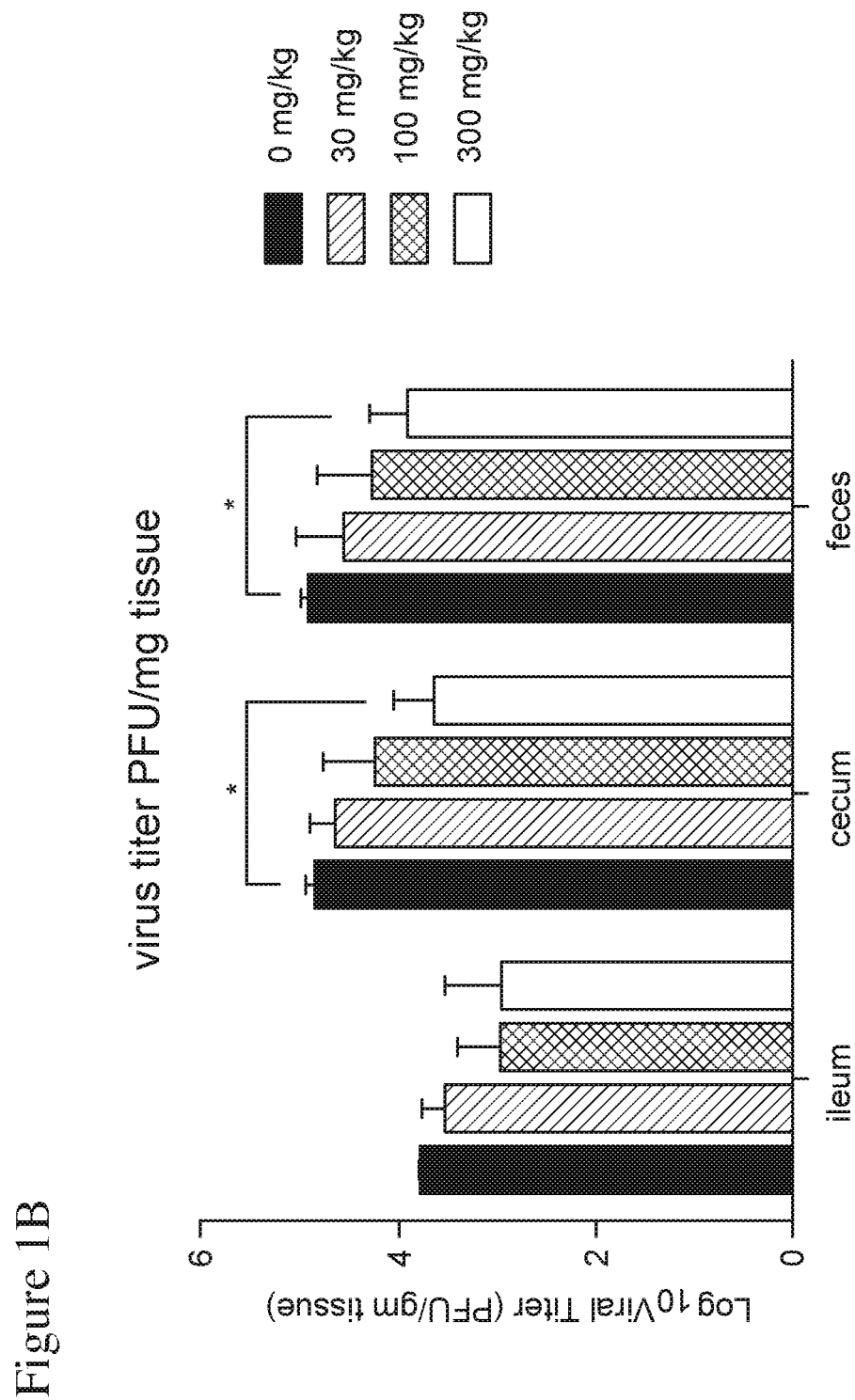
FIG. 1B shows murine norovirus titer (plaque forming units per mg of tissue) in tissue and feces harvested 3 days post-infection as part of Study No. 1.

FIG. 1A and FIG. 1B. The data also demonstrate a significant reduction in virus titer for animals treated twice-daily with 300 mg/kg Compound 1 in both tissue and feces compared with vehicle.

As shown in FIGS. 1A and 1B, mice were treated via oral gavage with the indicated doses of Compound 1 given twice daily, starting 2 days prior to infection with $10^6$ pfu of murine norovirus as set forth in "Study No. 1."

Results of Study No. 2 demonstrate that treatment of mice twice daily with 300 mg/kg of Compound 1, starting 2 days prior to infection, significantly reduces murine norovirus titer both in tissue and feces as shown in FIG. 2A and FIG. 2B. These data confirm the findings of Study #1 and demonstrate that Compound 1 is efficacious in reducing murine norovirus infection.

As shown in FIGS. 2A and 2B, mice were treated via oral gavage with the indicated doses of Compound 1 administered twice daily, starting at the indicated days prior to infection with $10^4$ PFU of murine norovirus as set forth in "Study No. 1.".

FIGS. 3A and 3B show the number of plaque forming units per gram from Study 1 on a linear scale instead of a logarithmic scale. As shown in FIG. 3A, compound 1 dosed orally BID (twice per day) starting on day −2 before infection (n=5/group) showed a reduction in PFU/gram with increasing dose. As shown in FIGS. 3A and 3B, compound 1 reduces mouse norovirus in tissues and stool.

Example 3—Norovirus Polymerase Inhibition Assay

Polymerase reactions (10 μL) were conducted for 60 minutes at 37° C. Nucleoside triphosphates (NTPs) were present at 100 μM each, with 0.05 μCi α32P-UTP (800 Ci/mmol). Compounds were incubated with the polymerase (Pol) or pro-polymerase (ProPol), with or without viral protein genome-linked (VPg) in reaction buffer in the absence of NTPs for 10 minutes on ice. Reactions were initiated by the addition of NTPs, and terminated by the addition of an equal volume of 2×Tris/Borate/EDTA (TBE) loading dye/buffer (Invitrogen, Inc.). RNA products (100 nt) were resolved by electrophoresis in 6% TBE-urea gels (Invitrogen, Inc.). Semi-quantitative analysis of RNA products was conducted by exposure of dried gels to GE Healthcare Phosphor screens, followed by measurement of relative band intensities using GelQuant.NET software (Biochem-Lab Solutions, Inc.). $IC_{50}$ and $IC_{90}$ calculations were obtained using linear regression. The results are given below in Table 5. A comparison with 2'-C-methylcytidine triphosphate (2'CmeC TP) is given for reference.

TABLE 5

| Norovirus Polymerase Assays | | | |
|---|---|---|---|
| Compound | Polymerase | $IC_{50}$ | $IC_{90}$ |
| 2'CmeC TP | Pol | 1.71 ± 0.05 | 4.45 ± 0.28 |
| 2'CmeC TP | Pol + VPg | 1.70 ± 0.04 | 4.07 ± 0.17 |
| 2'CmeC TP | ProPol | 1.77 ± 0.04 | 4.71 ± 0.18 |
| 2'CmeC TP | ProPol + VPg | 1.71 ± 0.06 | 4.23 ± 0.35 |
| Compound 1 TP | Pol | 3.41 ± 0.14 | 9.63 ± 0.78 |
| Compound 1 TP | Pol + VPg | 3.37 ± 0.10 | 9.33 ± 0.72 |
| Compound 1 TP | ProPol | 3.35 ± 0.12 | 9.78 ± 0.60 |
| Compound 1 TP | ProPol + VPg | 3.01 ± 0.14 | 9.64 ± 0.85 |

Example 4—Conversion of Compound 1 to Triphosphate in RAW Cells

RAW cells were incubated with Compound 1 at the concentrations shown in Table 6a (ng/cell) and in Table 6b (pmol/cell).

TABLE 6a

| Conversion of Compound 1 to Triphosphate in ng/cell | | | |
|---|---|---|---|
| Compound | Concentration (ng/1 × $10^6$ cells) | | (Compound 1- |
| 1 Conc. | Compound 1 | Compound 1-TP | TP)/(Compound 1) (ng) |
| 0.5 μM | 0.17 | 3.74 | 21.8 |
| 1 μM | 0.13 | 5.13 | 39.4 |
| 5 μM | 0.65 | 26.77 | 41.3 |
| 10 μM | 1.02 | 41.78 | 41.1 |

TABLE 6b

| Conversion of Compound 1 to Triphosphate in pmol/cell. | | | |
|---|---|---|---|
| Compound | Concentration (pmol/1 × $10^6$ cells) | | (Compound 1- |
| 1 Conc. | Compound 1 | Compound 1-TP | TP)/(Compound 1) (pmol) |
| 0.5 μM | 0.53 | 6.37 | 12.0 |
| 1 μM | 0.40 | 8.74 | 21.7 |
| 5 μM | 2.01 | 45.61 | 22.7 |
| 10 μM | 3.15 | 71.18 | 22.6 |

RAW cells were incubated with four different concentrations of Compound 1 for 48 hours in T75 flasks at a density of 1.2×$10^7$ cells/flask. After the incubation period, the cells were rinsed twice with cold PBS and counted. The cell pellet was suspended in 1000 μL of cold methanol:distilled water (70:30), vortexed, and frozen at −80° C. until time of analysis. As shown in Tables 6a and 6b, Compound 1 and Compound 1-TP could be detected in RAW cells treated with Compound 1 at concentrations from 0.5 μM to 10 μM. The concentration of Compound 1-TP was 12 to 23-fold higher than Compound 1.

Example 5—Efficacy of Compound 1 Against Human Norovirus

The efficacy of compound 1 for inhibiting norovirus was compared to DMSO (as a control), compound 2, and 2'-C-methylcytidine triphosphate (2'CmeC TP). Cells were pre-treated with 25 μM of experimental compound for two hours. Virus inoculum was added for two hours, and unbound virus washed off and fresh media and fresh experimental compound was added.

The experiment was conducted in duplicate and the results are shown in FIG. 4 (first duplicate) and FIG. 5 (second duplicate). FIG. 6 shows an overlay of the results of the first and second duplicate of the experiment. As shown in FIGS. 4, 5 and 6, "A" is DMSO, "B" is Compound 2, "C" is 2'-C-methylcytidine triphosphate (2'CmeC TP) and "D" is Compound 1. FIGS. 4-6 demonstrate that the viral titer increased almost two orders of magnitude when treated with only DMSO or 2'CmeC TP. However, the viral titer increased less than one order of magnitude in the presence of compound 1.

Example 6—Effective Concentration of Compounds of the Disclosure and Analogs Thereof Table 7 below shows the $EC_{50}$ and $CC_{50}$ values of some compounds of the disclosure as well as analogs thereof for murine norovirus. In cases where the compounds were assayed but no $EC_{50}$ value could be measured, the $EC_{50}$ value is given as N/A.

TABLE 7

$EC_{50}$ values for Compounds of Formula II

| Compound No. | $EC_{50}$ (μM) |
|---|---|
| 1 | 1.7-3.6 |
| 2 | 1.9-4.15 |
| 3 | 2.0 |
| 4 | 3.5 |
| 5 | 2.2 |
| 6 | 3.08 |
| 71 | 3.15 |
| 77 | 4.4 |
| 76 | 16.4 |
| 107 | 18.1 |
| 111 | 21 |
| 126 | 33.6 |
|  | 38.9 |
| 133 | 25.7 |
| 137 | 20 |
| 139 | 2.3 |
| 141 | 3.2 |
| 143 | 26.3 |
| 145 | 7.4 |

TABLE 8

$EC_{50}$ values for of Compounds of the Disclosure and Analogs thereof

| Compound No. | $EC_{50}$ (μM) | $CC_{50}$ |
|---|---|---|
| 7 | 53.8/38.4 | |
| 8 | 23.6 | |
| 10 | 61.5 | |
| 11 | >121 | >121 |
| 12 | N/A | |
| 14 | >100 | |
| 16 | >100 | |
| 17 | >100 | |
| 18 | >100 | |
| 19 | >100 | |
| 20 | >20 | >20 |
| 21 | >100 | |
| 22 | >100 | |
| 27 | >100 | |
| 28 | >100 | |
| 29 | >100 | |
| 30 | >100 | |
| 31 | >100 | |
| 32 | >100 | |
| 33 | >100 | |
| 34 | >100 | |
| 35 | >100 | |
| 36 | >100 | |
| 37 | >100 | |
| 38 | >100 | |
| 39 | >100 | |
| 41 | >100 | |
| 42 | >100 | |
| 43 | >100 | |
| 44 | >100 | |
| 45 | >100 | |
| 46 | >100 | |
| 47 | >100 | |
| 48 | >100 | |
| 49 | >100 | |
| 50 | >100 | |
| 51 | >100 | |
| 54 | >100 | |
| 61 | >100 | |
| 63 | >100 | |
| 65 | >100 | |
| 66 | 20.2 | 71.8 |
| 68 | >100 | |
| 69 | >100 | |
| 72 | >100 | |
| 73 | >100 | |
| 78 | >100 | |
| 81 | >100 | |
| 82 | >100 | |
| 83 | >100 | |
| 84 | >100 | |
| 85 | >100 | |
| 86 | >100 | |
| 88 | >100 | |
| 91 | >100 | |
| 93 | >100 | |
| 94 | >100 | |
| 95 | >100 | |
| 96 | NA | |
| 98 | >100 | |
| 100 | >100 | |
| 103 | >100 | |
| 104 | >100 | |
| 106 | >100 | |
| 108 | >100 | |
| 110 | >100 | |
| 114 | >100 | |
| 115 | >100 | |
| 116 | >100 | |
| 117 | >100 | |
| 120 | >100 | |
| 121 | >100 | |
| 122 | >100 | |
| 123 | >100 | |
| 124 | >100 | |
| 125 | >100 | |
| 128 | >100 | |
| 129 | 88.7 | |
| 130 | 42.7 | |
| 131 | >100 | |
| 132 | >100 | |
| 134 | 68.4 | |
| 136 | 64.5 | |
| 138 | >100 | |
| 140 | >100 | |
| 142 | >100 | |
| 144 | >100 | |
| 9 | 50 | |
| 13 | >200 | >200 |
| 15 | >100 | >100 |
| 23 | >100 | |
| 24 | >20 | >20 |
| 25 | >100 | |
| 26 | >100 | |
| 40 | >100 | |
| 52 | >100 | |
| 53 | >100 | |
| 55 | N/A | |
| 56 | 75.3 | |
| 57 | >100 | |
| 58 | >100 | |
| 59 | >100 | |
| 60 | N/A | |
| 62 | >100 | |
| 64 | >100 | |
| 67 | >100 | |

TABLE 8-continued

EC$_{50}$ values for of Compounds of the Disclosure and Analogs thereof

| Compound No. | EC$_{50}$ (μM) | CC$_{50}$ |
|---|---|---|
| 70 | >100 | |
| 74 | >100 | |
| 75 | >100 | |
| 79 | >100 | |
| 80 | >100 | |
| 87 | >100 | |
| 89 | >100 | |
| 90 | >100 | |
| 92 | >100 | |
| 97 | >100 | |
| 99 | >100 | |
| 101 | >100 | |
| 102 | >100 | |
| 105 | >100 | |
| 109 | >100 | |
| 112 | >100 | |
| 113 | >100 | |
| 118 | >100 | |
| 119 | >100 | |
| 135 | >100 | |
| 127 | 5.5 | |

Example 7—Synthesis of Compound 1

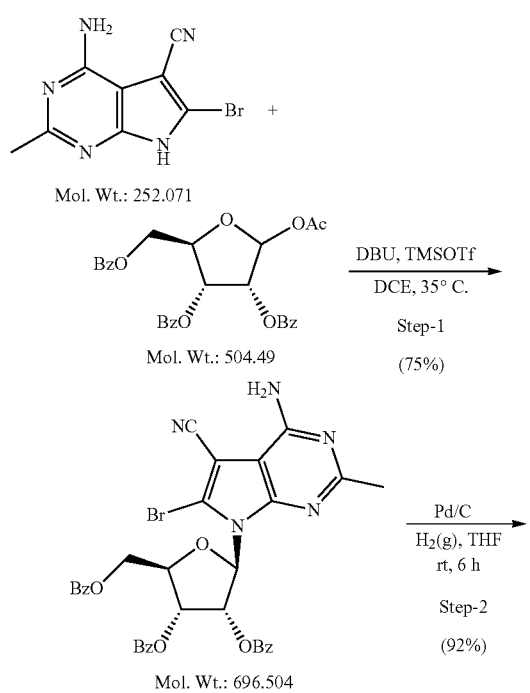

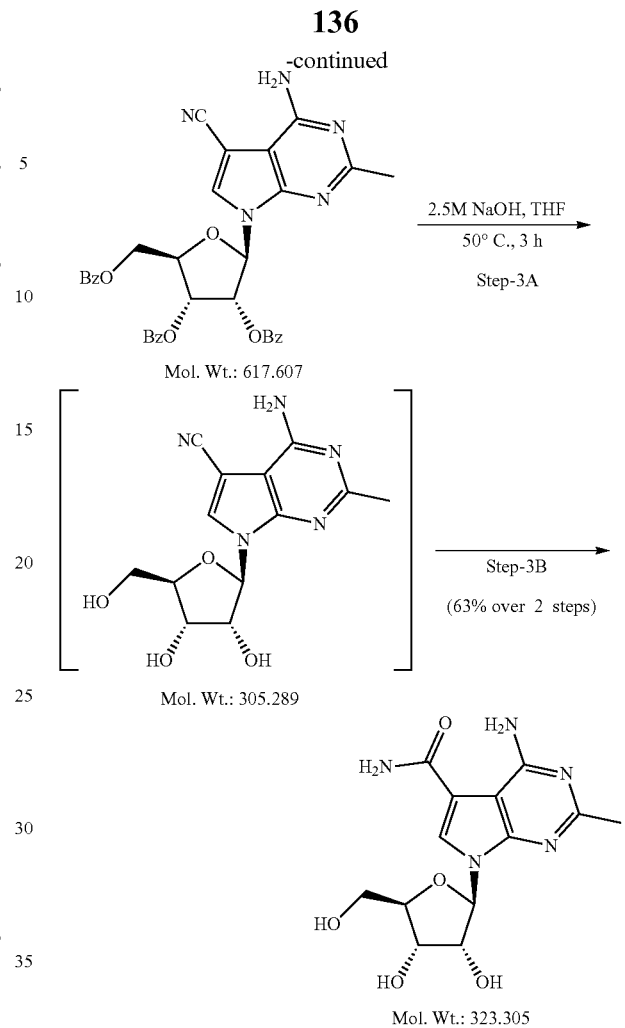

Step 1 (Protocol #1):

To a 100-L jacketed reactor were charged 4-amino-6-bromo-2-methyl-7H-pyrrolo[2,3-d]pyrimidine-5-carbonitrile (3.00 kg), (3R,4R,5R)-2-acetoxy-5-((benzoyloxy)methyl)tetrahydrofuran-3,4-diyl dibenzoate (6.60 kg) and DCE (18.89 kg). Stirring was started and DBU (3.61) kg was added. Over a period of 03 h and 14 min, TMSOTf (8.01 kg) was added between 30.6° C. and 37.3° C. IPC after 01 h and 30 min at approx. 32° C. showed 4% of 4-amino-6-bromo-2-methyl-7H-pyrrolo[2,3-d]pyrimidine-5-carbonitrile (3.00 kg), (3R,4R,5R)-2-acetoxy-5-((benzoyloxy)methyl)tetrahydrofuran-3,4-diyl dibenzoate remaining. IPC after 03 h and 16 min at approx. 32° C. showed 2% 4-amino-6-bromo-2-methyl-7H-pyrrolo[2,3-d]pyrimidine-5-carbonitrile (3.00 kg), (3R,4R,5R)-2-acetoxy-5-((benzoyloxy)methyl)tetrahydrofuran-3,4-diyl dibenzoate remaining (spec: <3%). The reaction mixture was diluted with DCM (39.81 kg) and quenched with potable water (15.02 kg) over an 11 min period between 9.5° C. and 15.6° C. The extractive work-up (at approx. 22° C.) was completed by a back extraction of the aqueous phase with DCM (19.90 kg), a wash with sat NaHCO$_3$ (1.3 kg NaHCO$_3$ in 14.9 kg potable water), a back extraction of the bicarbonate phase with DCM (19.71 kg) and a wash with brine (4.5 kg NaCl in 14.9 kg potable water). Note: the reactor was cleaned with potable water, acetone and DCM after each wash/back extraction.

The drummed organic phase containing the product was charged to the 100-L jacketed reactor through an in-line filter followed by a DCM rinse of the drum and filter with DCM (2.48 kg). The contents of the reactor were distilled to 31 L with the aid of vacuum over a period of 06 h and 04 min with a maximum temperature of 50.1° C. At this point a thick suspension had formed. Next, over a period of 39 min, IPAc (41.88 kg) was added between 44.5° C. and 49.5° C. and the contents of the reactor were heated to 76.9° C. over a period of 01 h and 25 min. Next, the contents of the reactor were cooled to 9.9° C. over a period of 04 h and 21 min and stirred for 12 h and 26 min with a minimum temperature of 1.6° C.

Step 1 (Protocol #2):

To a 100-L jacketed reactor were charged 4-amino-6-bromo-2-methyl-7H-pyrrolo[2,3-d]pyrimidine-5-carbonitrile (3.00 kg), (3R,4R,5R)-2-acetoxy-5-((benzoyloxy) methyl)tetrahydrofuran-3,4-diyl dibenzoate (6.60 kg) and DCE (18.80 kg). Stirring was started and DBU (3.59) kg was added. Over a period of 01 h and 46 min, TMSOTf (7.90 kg) was added between 30.4° C. and 34.2° C. IPC after 02 h and 49 min at approx. 34° C. showed 1% of 4-amino-6-bromo-2-methyl-7H-pyrrolo[2,3-d]pyrimidine-5-carbonitrile remaining (spec: <3%). The reaction mixture was diluted with DCM (40/70 kg) and quenched with potable water (14.97 kg) over an 04 min period between 9.9° C. and 18.0° C. The extractive work-up (at approx. 22° C.) was completed by a back extraction of the aqueous phase with DCM (20.34 kg), a wash with sat NaHCO$_3$ (1.30 kg NaHCO$_3$ in 14.90 kg potable water), a back extraction of the bicarbonate phase with DCM (20.65 kg) and a wash with brine (4.50 kg NaCl in 14.96 kg potable water). Note: the reactor was cleaned with potable water, acetone and DCM after each wash/back extraction.

The drummed organic phase containing the product was charged to the 100-L jacketed reactor through an in-line filter followed by a DCM rinse of the drum and filter with DCM (1.49 kg). The contents of the reactor were distilled to with the aid of vacuum over a period of 04 h and 49 min with a maximum temperature of 45.6° C. At this point a thick suspension had formed. Next, over a period of 27 min, IPAc (41.70 kg) was added between 45.6° C. and 48.2° C. and the contents of the reactor were heated to 75.7° C. over a period of 01 h and 20 min. Next, the contents of the reactor were cooled to 9.4° C. over a period of 04 h and 15 min and stirred overnight with a minimum temperature of 2.3° C.

Step 2:

To the reactor were charged (2R,3R,4R,5R)-2-(4-amino-6-bromo-5-cyano-2-methyl-7H-pyrrolo[2,3-d]pyrimidin-7-yl)-5-((benzoyloxy)methyl)tetrahydrofuran-3,4-diyl dibenzoate (10.0 kg), 10% Pd on C (Degussa, Type E101NE/W), trimethylamine (7.3 kg) and THF (44.5 kg). Hydrogen was submitted to the reactor and the mixture was stirred for 03 h and 54 min between 24.7° C. and 19.6° C. at approx. 30.8 psig. IPC (HPLC) showed that (2R,3R,4R,5R)-2-(4-amino-6-bromo-5-cyano-2-methyl-7H-pyrrolo[2,3-d]pyrimidin-7-yl)-5-((benzoyloxy)methyl)tetrahydrofuran-3,4-diyl dibenzoate could no longer be detected.

The reaction mixture was filtered over Celite (7.2 kg) and a polish filter and the filter residue was washed with THF (5.2 kg). The combined filtrate and wash was transferred to a 100-L jacketed reactor with the aid of a THF wash (2.12 kg). The contents of the reactor were vacuum distilled with a maximum batch temperature of 30.0° C. over a period of 05 h and 38 min to a final volume of 27 L. IPA (31.48 kg) was charged over a 40 min period to the reactor between 39.7° C. and 53.2° C. The contents of the reactor were vacuum distilled with a maximum batch temperature of 53.2° C. over a period of 03 h and 02 min to a final volume of 33 L. IPA (48.99 kg) was charged over a 43 min period to the reactor between 53.1° C. and 57.1° C. The contents of the reactor were heated to 60.2° C., agitated for 12 min and cooled over a period of 04 and 28 min to 5.4° C. Cold stirring was continued for a period of 08 h and 55 min with a minimum temperature of 1.1° C. The slurry was filtered and washed with IPA (9.41 kg, at approx. 4.5° C.). The residue was dried under vacuum with a nitrogen bleed for a period of 11 h and 44 min at a maximum temperature of 44.0° C. to provide an LOD of 0.36%. Yield: 6.58 kg (73.9%). $^1$H NMR confirms structure. Purity: 97.78% (HPLC, AUC).

Step 3:

| Materials | MW | Eqs/vol | Amount | mmoles | Lot # |
|---|---|---|---|---|---|
| (2R,3R,4R,5R)-2-(4-amino-5-cyano-2-methyl-7H-pyrrolo[2,3-d]pyrimidin-7-yl)-5-((benzoyloxy)methyl) tetrahydrofuran-3,4-diyl dibenzoate | 617.607 | 1 | 366.9 | 594.1 | |
| 2.5M NaOH[1] | | 2.5 | 910 mL | | Sigma Aldrich/ 221465/ ACS/ MKBT1665V |
| Water | | As needed | | | Potable |
| THF | | 2.5 | 910 mL | | Sigma Aldrich/ 360589/ ACS/ SHBG3052V |
| 3M HCl[2] | | As needed | | | Sigma Aldrich/ 258148/ ACS, 37%/ SHBG3175V |

[1]100 g NaOH dissolved in potable water to a total volume of 1 L;
[2]Diluted 500 mL conc. HCl in 2 L total with potable water A solution of (2R,3R,4R,5R)-2-(4-amino-5-cyano-2-methyl-7H-pyrrolo[2,3-d]pyrimidin-7-yl)-5-((benzoyloxy) methyl)tetrahydrofuran-3,4-diyl dibenzoate and THF was heated to 54° C. and the addition of 2.5 M NaOH was started. The initial addition gave a biphasic mixture and endothermic response (the temperature dropped to 50° C.) but as the addition continued a single phased, clear solution formed which was accompanied by a fast exotherm to 61° C.; the reaction temperature was maintained at 60° C. to 61° C. during the rest of the addition and for an additional 2½ h. IPC showed that no (2R,3R,4R,5R)-2-(4-amino-5-cyano-2-methyl-7H-pyrrolo[2,3-d]pyrimidin-7-yl)-5-((benzoyloxy)methyl)tetrahydrofuran-3,4-diyl dibenzoate was left.

The reaction mixture was cooled to 21° C. and neutralized with 3 N HCl with external cooling to pH=7.06 (Denver Instrument UB-10 pH meter equipped with a Sartorius P-P11 pH electrode, the electrode was checked with buffer solutions of pH=4.00 and pH=7.00); the mixture continued to cool to 8° C. The resulting neutralized mixture was distilled under vacuum with a pot temperature of 45° C. to 50° C. until the emergence of solids were observed in the pot. The suspension was cooled and stirred for 2 h at 2° C. The beige suspension was filtered to afford a dark filtrate; the off-white residue was washed once with cold water (500 mL, 5° C.). A first LOD after 16 h gave a value of 18.73%. HPLC) of the drying material showed the presence of 1.6% benzoate.

A brief rework study for compound 1, (containing 1.6% benzoic acid per AUC, HPLC) was executed in 10 vol of water (1 g in 10 mL):

3 h slurry at ambient
3 h slurry at 50° C.
24 h slurry at ambient

All three experiments gave compound 1 with less than 0.1% benzoic acid (UAC, HPLC). The slurries were fluid, were easily stirred and filtration was fast. Short term drying on the filter gave a powder-like solid indicating that a displacement wash with an organic solvent is not needed. Without wishing to be bound by theory, a loss of NMT than 1% is expected (solubility 1 mg/mL). HPLC data for compound 1 were obtained with a method suitable for polar compounds using a Zorbax Eclipse Plus $C_{18}$ column (water/ACN/TFA, 97.5/2.5/0.05). This is the same column used for steps 1 and 2.

The cold product suspension was filtered and the reactor and residue were washed with cold IPAc (approx. 7.5° C., 13.16 kg and 13.62 kg) until a colorless filtrate had been obtained. The residue was dried under vacuum and a nitrogen bleed <45° C. for a period of 65 h and 19 min to an LOD of 0%. Yield: 5.87 kg (70.7%), $^1$H NMR confirmed identity; HPLC purity 98.84% (AUC).

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A compound of the formula:

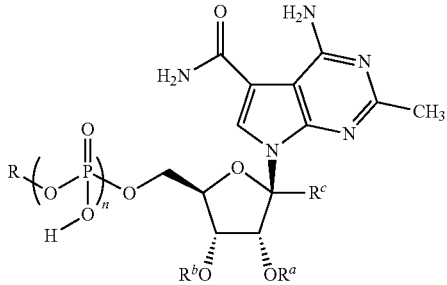

or a pharmaceutically acceptable salt, solvate, enantiomer, diastereomer, racemate or mixture thereof, wherein:

each R is independently —H, —$C_1$-$C_{20}$alkyl, —$C_2$-$C_{20}$alkenyl, —$C_2$-$C_{20}$alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, $R^1$, —OR, —$NR^1R^2$, —$SR^1$, —OC(O)$R^1$, —C(O)O$R^1$, —NHC(O)O$R^1$, or —NHC(O)$R^1$;

$R^a$ and $R^b$ are each independently, at each occurrence, —H, —$C_1$-$C_{20}$alkyl, —$C_2$-$C_{20}$alkenyl, —$C_2$-$C_{20}$ alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —O$R^1$, —$NR^1R^2$, —$SR^1$, —OC(O)R, —C(O)O$R^1$—NHC(O)OR, or —NHC(O)$R^1$;

$R^1$ and $R^2$ are each independently, at each occurrence, —H, —$C_1$-$C_{20}$alkyl, —$C_2$-$C_{20}$alkenyl, —$C_2$-$C_{20}$alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —$R^3$, —$R^4$, —O$R^3$, —$NR^3R^4$, —$SR^3$, —OC(O)$R^3$, —C(O)O$R^3$, —NHC(O)O$R^3$, or —NHC(O)$R^3$;

$R^3$ and $R^4$ are each independently, at each occurrence, —H, —$C_1$-$C_{20}$alkyl, —$C_2$-$C_{20}$alkenyl, —$C_2$-$C_{20}$alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —$NH_2$, —SH, —OC(O)H, —C(O)OH, —NHC(O)OH, or —NHC(O)H;

$R^c$ is independently —H or -D; and n is independently 0, 1, 2 or 3.

2. The compound claim 1, wherein the compound is of the formula:

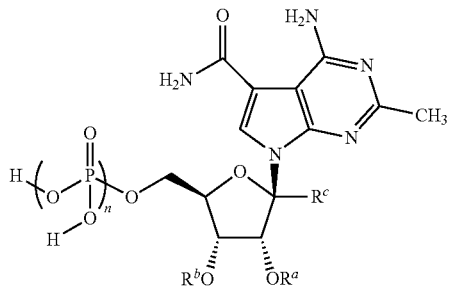

or a pharmaceutically acceptable salt, solvate, enantiomer, diastereomer, racemate or mixture thereof, wherein:

$R^a$ and $R^b$ are each independently, at each occurrence, —H, —$C_1$-$C_{20}$alkyl, —$C_2$-$C_{20}$alkenyl, —$C_2$-$C_{20}$ alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —O$R^1$, —$NR^1R^2$, —$SR^1$, —OC(O)$R^1$,—C(O)O$R^1$ —NHC(O)O$R^1$, or —NHC(O)$R^1$;

$R^1$ and $R^2$ are each independently, at each occurrence, —H, —$C_1$-$C_{20}$alkyl, —$C_2$-$C_{20}$alkenyl, —$C_2$-$C_{20}$alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —$R^3$, —$R^4$, —O$R^3$, —$NR^3R^4$, —$SR^3$, —OC(O)$R^3$,—C(O)O$R^3$, —NHC(O)O$R^3$, or —NHC(O)$R^3$;

$R^3$ and $R^4$ are each independently, at each occurrence, —H, —$C_1$-$C_{20}$alkyl, —$C_2$-$C_{20}$alkenyl, —$C_2$-$C_{20}$alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —$NH_2$, —SH, —OC(O)H,—C(O)OH, —NHC(O)OH, or —NHC(O)H;

$R^c$ is independently —H or -D; and n is independently 0, 1, 2 or 3.

3. The compound claim 1, wherein the compound is of the formula:

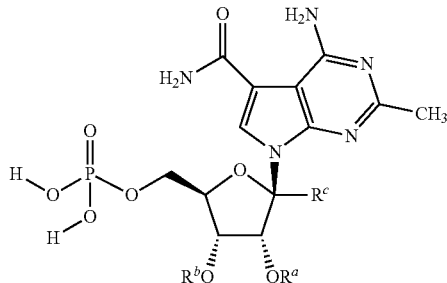

or a pharmaceutically acceptable salt, solvate, enantiomer, diastereomer, racemate or mixture thereof, wherein:

$R^a$ and $R^b$ are each independently, at each occurrence, —H, —$C_1$-$C_{20}$alkyl, —$C_2$-$C_{20}$alkenyl, —$C_2$-$C_{20}$ alkynyl, —$C_3$-$C_8$ cycloalkyl, —$C_4$-$C_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —OR$^1$, —NR$^1$R$^2$, —SR$^1$, —OC(O)R$^1$,—C(O)OR$^1$ —NHC(O)OR$^1$, or —NHC(O)R$^1$;

R$^1$ and R$^2$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —R$^3$, —R$^4$, —OR$^3$, —NR$^3$R$^4$, —SR$^3$, —OC(O)R$^3$,—C(O)OR$^3$, —NHC(O)OR$^3$, or —NHC(O)R$^3$;

R$^3$ and R$^4$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —NH$_2$, —SH, —OC(O)H,—C(O)OH, —NHC(O)OH, or —NHC(O)H; and R$^c$ is independently —H or -D.

4. The compound claim 1, wherein the compound is of the formula:

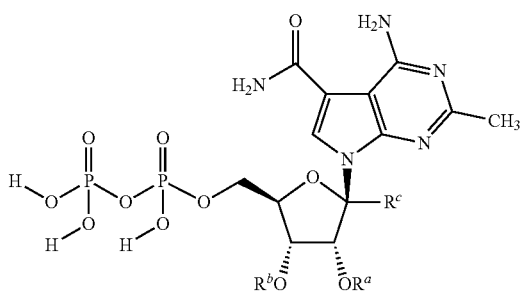

or a pharmaceutically acceptable salt, solvate, enantiomer, diastereomer, racemate or mixture thereof, wherein:

R$^a$ and R$^b$ are each independently, at each occurrence, —H, —C$_1$-C$_{20}$alkyl, —C$_2$-C$_{20}$alkenyl, —C$_2$-C$_{20}$ alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —OR$^1$, —NR$^1$R$^2$, —SR$^1$, —OC(O)R$^1$,—C(O)OR$^1$ —NHC(O)OR$^1$, or —NHC(O)R$^1$;

R$^1$ and R$^2$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —R$^3$, —R$^4$, —OR$^3$, —NR$^3$R$^4$, —SR$^3$, —OC(O)R$^3$,—C(O)OR$^3$, —NHC(O)OR$^3$, or —NHC(O)R$^3$;

R$^3$ and R$^4$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —NH$_2$, —SH, —OC(O)H,—C(O)OH, —NHC(O)OH, or —NHC(O)H; and R$^c$ is independently —H or -D.

5. The compound claim 1, wherein the compound is of the formula:

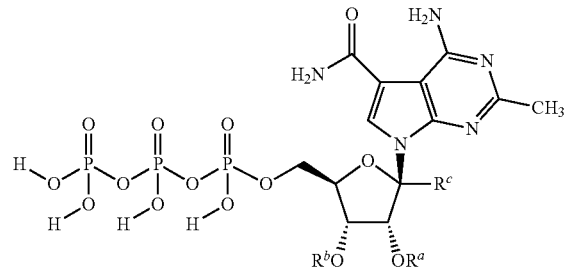

or a pharmaceutically acceptable salt, solvate, enantiomer, diastereomer, racemate or mixture thereof, wherein:

R$^a$ and R$^b$ are each independently, at each occurrence, —H, —C$_1$-C$_{20}$alkyl, —C$_2$-C$_{20}$alkenyl, —C$_2$-C$_{20}$ alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo —OR$^1$, —NR$^1$R$^2$, —SR$^1$, —OC(O)R$^1$,—C(O)OR$^1$ —NHC(O)OR$^1$, or —NHC(O)R$^1$;

R$^1$ and R$^2$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, —R$^3$, —R$^4$, —OR$^3$, —NR$^3$R$^4$, —SR$^3$, —OC(O)R$^3$,—C(O)OR$^3$, —NHC(O)OR$^3$, or —NHC(O)R$^3$;

R$^3$ and R$^4$ are each independently, at each occurrence, —H, —C$_1$-C$_{20}$alkyl, —C$_2$-C$_{20}$alkenyl, —C$_2$-C$_{20}$alkynyl, —C$_3$-C$_8$ cycloalkyl, —C$_4$-C$_8$ cycloalkenyl, aryl, heteroaryl, or heterocyclyl, wherein each alkyl, alkenyl, alkynyl, cycloalkyl, cycloalkenyl, aryl, heteroaryl, or heterocyclyl is optionally substituted with one or more halogen, oxo, aryl, heteroaryl, —OH, —NH$_2$, —SH, —OC(O)H,—C(O)OH, —NHC(O)OH, or —NHC(O)H; and R$^c$ is independently —H or -D.

6. The compound claim 1, wherein the compound is of the formula:

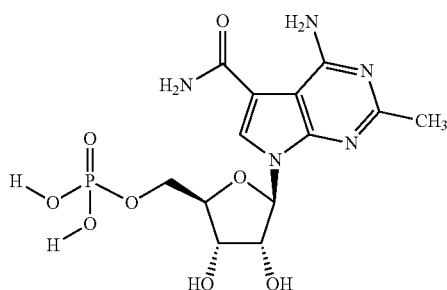 [SMILES: Cc1nc(N)c2c(C(N)=O)cn([C@@H]3O[C@H](COP(=O)(O)O)[C@@H](O)[C@H]3O)c2n1]

or a pharmaceutically acceptable salt, solvate, enantiomer, diastereomer, racemate or mixture thereof.

7. The compound claim 1, wherein the compound is of the formula:

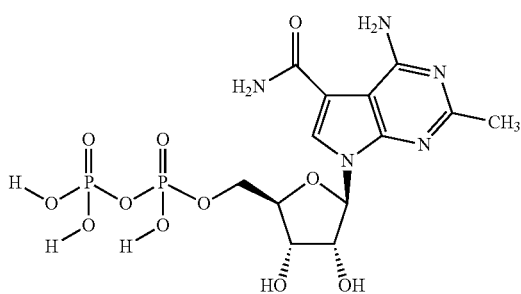 [SMILES: Cc1nc(N)c2c(C(N)=O)cn([C@@H]3O[C@H](COP(=O)(O)OP(=O)(O)O)[C@@H](O)[C@H]3O)c2n1]

or a pharmaceutically acceptable salt, solvate, enantiomer, diastereomer, racemate or mixture thereof.

8. The compound claim 1, wherein the compound is of the formula:

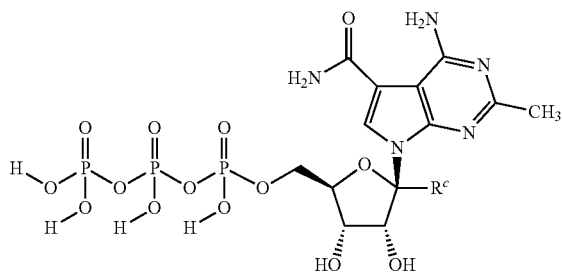

or a pharmaceutically acceptable salt, solvate, enantiomer, diastereomer, racemate or mixture thereof.

9. The compound of claim 1, wherein the compound exists in vivo.

10. The compound of claim 1, wherein the compound is produced in vivo.

11. A method of treating or preventing a viral infection comprising administering to a subject in need thereof an effective amount of a compound of claim 1 a pharmaceutically acceptable salt, solvate, enantiomer, diastereomer, racemate or mixture thereof.

12. A method of treating or preventing a viral infection comprising administering to a subject in need thereof an effective amount of a compound that is converted to a compound of claim 1 a pharmaceutically acceptable salt, solvate, enantiomer, diastereomer, racemate or mixture thereof in vivo.

13. The method of claim 11 wherein the viral infection is norovirus infection.

14. The method of claim 12 wherein the viral infection is norovirus infection.

15. The compound of claim 8, wherein the compound exists in vivo.

16. The compound of claim 8, wherein the compound is produced in vivo.

* * * * *

UNITED STATES PATENT AND TRADEMARK OFFICE
CERTIFICATE OF CORRECTION

PATENT NO. : 10,941,175 B2  
APPLICATION NO. : 16/533194  
DATED : March 9, 2021  
INVENTOR(S) : John Henry Bougher, III et al.

Page 1 of 1

It is certified that error appears in the above-identified patent and that said Letters Patent is hereby corrected as shown below:

In the Claims

At Column 143, Claim number 1, Line number 28, replace:  
"–OR, –NR$^1$R$^2$, –SR$^1$, –OC(O)R$^1$, –C(O)OR$^1$,"  
With:  
-- –OR$^1$, –NR$^1$R$^2$, –SR$^1$, –OC(O)R$^1$, –C(O)OR$^1$,--

At Column 143, Claim number 1, Line number 39, replace:  
"–OC(O)R, –C(O)OR$^1$ –NHC(O)OR, or –NHC(O)"  
With:  
-- –OC(O)R$^1$, –C(O)OR$^1$ –NHC(O)OR$^1$, or –NHC(O)--

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*